(12) United States Patent
Rublee et al.

(10) Patent No.: US 7,214,492 B1
(45) Date of Patent: May 8, 2007

(54) NUCLEIC ACID ARRAYS TO MONITOR WATER AND OTHER ECOSYSTEMS

(75) Inventors: Parke A. Rublee, Greensboro, NC (US); Vincent C. Henrich, III, Greensboro, NC (US)

(73) Assignee: The University of North Carolina at Greensboro, Greensboro, NC (US)

( * ) Notice: Subject to any disclaimer, the term of this patent is extended or adjusted under 35 U.S.C. 154(b) by 0 days.

(21) Appl. No.: 11/071,849

(22) Filed: Mar. 3, 2005

Related U.S. Application Data

(63) Continuation-in-part of application No. 10/131,618, filed on Apr. 24, 2002, now abandoned.

(51) Int. Cl.
*C12Q 1/68* (2006.01)
*C07H 21/02* (2006.01)

(52) U.S. Cl. .............. 435/6; 435/283.1; 435/287.2; 536/23.1; 536/24.3

(58) Field of Classification Search .............. None
See application file for complete search history.

(56) References Cited

U.S. PATENT DOCUMENTS

| 5,429,807 A | 7/1995 | Matson et al. |
|---|---|---|
| 5,667,667 A | 9/1997 | Southern |
| 5,770,367 A | 6/1998 | Southern et al. |
| 5,837,832 A | 11/1998 | Chee et al. |
| 6,054,270 A | 4/2000 | Southern |
| 6,080,585 A | 6/2000 | Southern et al. |
| 6,150,095 A | 11/2000 | Southern et al. |
| 6,225,067 B1 | 5/2001 | Rogers |
| 6,228,575 B1 | 5/2001 | Gingeras et al. |
| 6,307,039 B1 | 10/2001 | Southern et al. |
| 6,309,822 B1 | 10/2001 | Fodor et al. |
| 6,355,420 B1 | 3/2002 | Chan |
| 6,537,801 B1 | 3/2003 | Ida et al. |
| 6,808,879 B1 | 10/2004 | Guillot et al. |

FOREIGN PATENT DOCUMENTS

| CN | 1396270 | 2/2003 |
|---|---|---|
| EP | 0 950 720 A1 | 10/1999 |

(Continued)

OTHER PUBLICATIONS

Campbell, Biology, 1993, Benjamin/Cummings, Redwood City, CA, 3rd ed., p. 1053.*

(Continued)

*Primary Examiner*—Juliet C. Switzer
*Assistant Examiner*—Robert T. Crow
(74) *Attorney, Agent, or Firm*—Kilpatrick Stockton LLP

(57) ABSTRACT

Disclosed are arrays for monitoring ecosystems, such as bodies of water, and methods and systems for making such arrays. In one embodiment, the array may include a plurality of oligonucleotides immobilized at known locations on a substrate, such that each location on the array is an oligonucleotide having a sequence derived from a single, predetermined operational taxonomic unit (OTU). The sequences immobilized on the array may be from known, or unknown organisms. Also disclosed are methods for identifying and isolating bioindicators diagnostic of specific ecosystems. The arrays and bioindicators of the invention may be used for rapid, and continual monitoring of ecosystems.

24 Claims, 21 Drawing Sheets
(4 of 21 Drawing Sheet(s) Filed in Color)

FOREIGN PATENT DOCUMENTS

| FR | 2844522 | 3/2004 |
|---|---|---|
| WO | WO 96/41893 | 12/1996 |
| WO | WO 97/22720 | 6/1997 |
| WO | WO 01/61038 A2 | 8/2001 |
| WO | WO 02/101094 A1 | 12/2002 |
| WO | WO 04/104211 A2 | 12/2004 |

OTHER PUBLICATIONS

Castiglioni, B. et al., "Development of a Universal Microarray Based on the Ligation Detection Reaction and 16SrRNA Gene Polymorphism to Target Diversity of Cyanobacteria," Applied and Environment Microbiology, vol. 70, No. 12, pp. 7161-7172, 2004.
Adleman, L. M., "Molecular Computation of Solutions to Combinatorial Problems," Science, vol. 266, pp. 1021-1024, 1994.
Anantharaman, V. et al., "TRAM, A Predicted RNA-Binding Domain, Common to tRNA Uracil Methylation and Adenine Thiolation Enzymes," FEMS Microbiology Letters, vol. 197, pp. 215-221, 2001.
Anantharaman, V. et al., "Regulatory Potential, Phyletic Distribution and Evolution of Ancient, Intracellular Small-Molecule-binding Domains," J. Mol. Biol., vol. 307, pp. 1271-1292, 2001.
Aravind, L. et al., "The $\alpha/\beta$ Fold Uracil DNA Glycosylases: A Common Origin with Diverse Fates," Genome Biology, vol. 1, No. 4, pp. research0007.1-0007.8, 2000.
Bej, A. K. et al., "Multiplex PCR Amplification and Immobilized Capture Probes for Detection of Bacterial Pathogens and Indicators in Water," Molecular and Cellular Probes, vol. 4, pp. 353-365, 1990.
Bassett Jr., D. E. et al., "Gene Expression Informatics—It's All in your Mine," Nature Genetics Supplement, vol. 21, pp. 51-55, 1999.
Bowtell, D. D. L., "Options Available—From Start to Finish—for Obtaining Expression Data by Microarray," Nature Genetics Supplement, vol. 21, pp. 25-32, 1999.
Cheung, V. G. et al., "Making and Reading Microarrays," Nature Genetics Supplement, vol. 21, pp. 15-19, 1999.
Geourjon, C. et al., "Identification of Related Proteins with Weak Sequence Identity using Secondary Structure Information," Protein Science, vol. 10, pp. 788-797, 2001.
Grech, A. et al., "Complete Structural Characterisation of the Mammalian and Drosophila TRAF Genes: Implications for TRAF Evolution and the Role of RING Finger Splice Variants," Molecular Immunology, vol. 37, pp. 721-734, 2000.
Guschin, D. Y. et al., "Oligonucleotide Microchips as Genosensors for Determinative and Environmental Studies in Microbiology," Applied and Environmental Microbiology, vol. 63, No. 6, pp. 2397-2402, 1997.
Hacia, J. G. et al., "Strategies for Mutational Analysis of the Large Multiexon ATM Gene Using High-Density Oligonucleotide Arrays," Genome Research, vol. 8, pp. 1245-1258, 1998.
Kitazoe, Y. et al., "A New Theory of Phylogeny Inference through Construction of Multidimensional Vector Space," Mol. Biol. Evol., vol. 18, No. 5, pp. 812-828, 2001.
Liberles, D. A. et al., "The Adaptive Evolution Database (TAED)," Genome Biology, vol. 2, No. 4, pp. preprint0003.1-0003.18, 2001.
Liu, Q. et al., "DNA Computing on Surfaces," Nature, vol. 403, pp. 175-179, 2000.
Muller, S. et al., "Defining the Ancestral Karyotype of All Primates by Multidimensional Chromosome Painting between Tree Shrews, Lemurs and Humans," Chromosoma, vol. 108, pp. 393-400, 1999.
Natale, D. A. et al., "Towards Understanding the First Genome Sequence of a Crenarchaeon by Genome Annotation using Clusters of Orthologous Groups of Proteins (COGs)," Genome Biology, vol. 1, No. 5, pp. research0009.1-0009.19, 2000.
Ramsay, G. et al., "DNA Chips: State-of-the-Art," Nature Biotechnology, vol. 16, pp. 40-44, 1998.
Sayada, C. et al., "Genomic Fingerprinting of Yersinia enterocolitica Species by Degenerate Oligonucleotide-Primed Polymerase Chain Reaction," Electrophoresis, vol. 15, pp. 562-565, 1994.
Southern, E. et al., "Molecular Interactions on Microarrays," Nature Genetics Supplement, vol. 21, pp. 5-9, 1999.

Woese, C. R., "Interpreting the Universal Phylogenetic Tree," PNAS, vol. 97, No. 15, pp. 8392-8396, 2000.
Antolin, M. et al., "Genes, Description of," Encyclopedia of Biodiversity, vol. 3, 2001.
Bavykin, S. et al., "Portable System for Microbial Sample Preparation and Oligonucleotide Microarray Analysis," Applied and Environmental Microbiology, vol. 67, p. 922-928, 2001.
Call, D. et al., "Detecting and Genotyping Escherichia coli O157:H7 using Multiplexed PCR and Nucleic Acid Microarrays," International Journal of Food Microbiology, vol. 67, p. 71-80, 2001.
Chizhikov, V. et al., "Microarray Analysis of Microbial Virulence Factors," Applied and Environmental Microbiology, vol. 67, No. 7, p. 3258-3263, 2001.
Friend, S. et al., "The Magic of Microarrays," Scientific American, vol. 286, No. 2, p. 44-53, 2002.
Gibson, G. et al., "Microarrays in Ecology and Evolution: A Preview," Molecular Ecology, vol. 11, p. 17-24, 2002.
Greer, C. et al., "Genomics Technologies for Environmental Science," Environmental Science and Technology, vol. 35, Issue 17, p. 360A-366A, 2001.
Lucchini, S. et al., "Microarrays for Microbiologists," Microbiology, vol. 147, p. 1403-1414, 2001.
Schonfelder, I. et al., "Relationships between Littoral Diatoms and their Chemical Environment in Northeastern German Lakes and Rivers," J. Phycol., vol. 38, p. 66-82, 2002.
Small, J. et al., "Direct Detection of 16S rRNA in Soil Extracts by Using Oligonucleotide Microarrays," Applied and Environmental Microbiology, vol. 67, No. 10, p. 4708-4716, 2001.
Tatusov, R. et al., "A Genomic Perspective on Protein Families," Science, vol. 278, p. 631-637, 1997.
Tatusov, R. et al., "The COG Database: A Tool for Genome-Scale Analysis of Protein Functions and Evolution," Nucleic Acid Research, vol. 28, No. 1, p. 33-36, 2000.
Tatusov, R. et al., "The COG Database: New Developments in Phylogenetic Classification of Proteins from Complete Genomes," Nucleic Acids Research, vol. 29, No. 1, p. 22-28, 2001.
Ye, R. et al., "Applications of DNA Microarrays in Microbial Systems," Journal of Microbiological Methods, vol. 47, p. 257-272, 2001.
Yen-Lieberman, B. et al., "Nucleic Acid Amplification Techniques and Evaluation of RNA Quantitation Assays in HIV 1 Subtype B Virus," 1998 Conference on the Laboratory Science of HIV.
Hiorns, W. et al., "Bacterial Diversity in Adirondack Mountain Lakes as Revealed by 16S rRNA Gene Sequence," Applied and Enviromental Microbiology, vol. 63, No. 7, p. 2957-2960, 1997.
Lemke, M. et al., "The Reponse of Three Bacterial Populations to Pollution in a Stream," Microb. Ecol., vol. 34, p. 224-231, 1997.
Rudi, K. et al., "Application of Sequence-Specific Labeled 16S rRNA Gene Oligonucleotide Probes for Genetic Profiling of Cyanobacterial Abundance and Diversity by Array Hybridization," Applied and Environmental Microbiology, vol. 66, No. 9, p. 4004-4011, 2000.
Wu, L. et al., "Development and Evaluation of Functional Gene Arrays for Detection of Selected Genes in the Environment," Applied and Environmental Microbiology, p. 5780-5790, 2001.
Altschul, S.F. et al., "Basic Local Alignment Search Tool," J. Mol. Biol., 1990, vol. 215, 403-410.
Amos, R. N., "Aquatic Microorganisms: Exploring Prokaryotic Diversity and its Relationship to Water Quality using 16S rDNA Sequences." Masters Thesis, Directed by Drs. Parke A. Rublee and Vincent C. Henrich, University of North Carolina at Greensboro, 2002, 55pgs.
Ausubel, F. M. et al., Short Protocols in Molecular Biology, 4th Ed., Chapter 2, John Wiley and Sons, N.Y. 1999.
Bernhard, A.E. et al., "Identification of Nonpoint Sources of Fecal Pollution in Coastal Waters by Using Host-Specific 16S Ribosomal DNA Genetic Markers from Fecal Anaerobes," Applied and Environmental Microbiology, 2000, vol. 66, No. 4, 1587-1594.
Bernhard, A.E. et al., "A PCR Assay to Discriminate Human and Ruminant Feces on the Basis of Host Differences in Bacteroides-Prevotella Genes Encoding 16S rRNA," Applied and Environmental Microbiology, 2000, vol. 65, No. 10, 4571-4574.

Blattner, F.R. et al., "The Complete Genome Sequence of *Escherichia coli* K-12," Science, 1997, vol. 277, 1453-1468.

Bowman, L., "Waterborne Illnesses on the Rise," Scripps-Howard News Service, Nov. 21, 2002, web site at http://www.shns.com/shns/g_index2.cfm?action=detail&pk=WATERDISEASE-11-21-02, as available via the Internet.

Brosius, J. et al., "Gene Organization and Primary Structure of a Ribosomal RNA Operon from *Escherichia coli*," J. Mol. Biol., 1981, vol. 148, 107-127.

Bruce, K.D. et al., "Amplification of DNA from Native Populations of Soil Bacteria by Using the Polymerase Chain Reaction," Appl. Environ. Microbiol., 1992, vol. 58, No. 10, 3413-3416.

Delorenzo, M. E. et al., "Effects of the Agricultural Pesticides Atrazine, Deethylatrazine, Endosulfan, and Chlorpyrifos on an Estuarine Microbial Food Web," Environmental Toxicology and Chemistry, 1999, vol. 18, No. 12, 2824-2835.

Diez, B. et al., "Application of Denaturing Gradient Gel Electrophoresis (DGGE) to Study the Diversity of Marine Picoeukaryotic Assemblages and Comparison of DGGE with other Molecular Techniques," Appl. Environ. Microbiol., 2001, vol. 67, No. 7, 2942-2951.

Edwards, U. et al., "Isolation and Direct Complete Nucleotide Determination of Entire Genes. Characterization of a Gene Coding for 16S Ribosomal RNA," Nucleic Acids Res., 1989, vol. 17, No. 19, 7843-7853.

Farrelly, V. et al., "Effect of Genome Size and rrn Gene Copy Number on PCR Amplification of 16S rRNA Genes from a Mixture of Bacterial Species," Appl. Environ. Microbiol., 1995, vol. 61, No. 7, 2798-2801.

Finlay, B. J., "Global Dispersal of Free-Living Microbiol Eukaryote Species," Science, 2002, vol. 296, 1061-1063.

Giovannoni, S. J. et al., "Genetic Diversity in Sargasso Sea Bacterioplankton," Nature, 1990, vol. 345, 60-63.

Grimes, D.J., "Ecology of Estuarine Bacteria Capable of Causing Human Disease: A Review," Estuaries, 1991, vol. 14, No. 4, 345-360.

Haldeman, D. L. et al., "Changes in Bacteria Recoverable from Subsurface Volcanic Rock Samples during Storage at 4 C," Appl. Environ. Microbiol., 1994, vol. 60, No. 8, 2697-2703.

Hiorns, W.D. et al., "Bacterial Diversity in Adirondack Mountain Lakes as Revealed by 16S rRNA Gene Sequences," Appl. Environ. Microbiol., 1997, vol. 63, No. 7, 2957-2960.

Hurlbert, S. H., "The Nonconcept of Species Diversity: A Critique and Alternative Parameters," Ecology, 1971, vol. 52, No. 4, 577-586.

Kaeberlein, T. et al., "Isolating "Uncultivable" Microorganisms in Pure Culture in a Simulated Natural Environment," Science, 2002, vol. 296, 1127-1129.

Kane, A. S. et al., "Fish Lesions in the Chesapeake Bay: Pfiesteria-like Dinoflagellates and other Etiologies," Maryland Medical Journal, 1998, vol. 47, No. 3, 106-112.

Kilham, P. et al., "Hypothesized Resource Relationships among African Planktonic Diatoms," Limnol. & Oceanogr., 1986, vol. 31, No. 6, 1169-1181.

Kopczysnski, E.D. et al., "Recognition of Chimeric Small-Subunit Ribosomal DNAs Composed of Genes from Uncultivated Microorganisms," Appl. Environ. Microbiol., 1994, vol. 60, No. 2, 746-748.

Leff, L.G. et al., "Identification of Aquatic Burkholderia (Pseudomonas) cepacia by Hybridization with Species-Specific rRNA Gene Probes," Appl. Environ. Microbiol., 1995, vol. 61, No. 4, 1634-1636.

Lemke, M. J. et al., "The Reponse of Three Bacterial Populations to Pollution in a Stream," Microb. Ecol., 1997, vol. 34, 224-231.

Lipp, E.K. et al., "Assessment and Impact of Microbial Fecal Pollution and Human Enteric Pathogens in a Coastal Community," Marine Pollution Bull., 2001, vol. 42, No. 4, 286-293.

Lopez-Garcia, P. et al., "Unexpected Diversity of Small Euraryotes in Deep-Sea Antartic Plankton," Nature, 2001, vol. 409, 603-607.

Mallin, M. A. et al., "North and South Carolina Coasts," Marine Pollution Bulletin, 2000, vol. 41, Nos. 1-6, 56-75.

Mallin, M. A., "Impacts of Industrial Animal Production on Rivers and Estuaries," American Scientist, 2000, vol. 88, Issue 1, 26-37, printed Jun. 9, 2005.

Mallin, M. A. et al., "Effect of Human Development on Bacteriological Water Quality in Coastal Watersheds," Ecological Applications, 2000, vol. 10, No. 4, 1047-1056.

Maniatis, T. et al., *Molecular Cloning: A Laboratory Manual*, Cold Spring Harbor Laboratory, 1982.

Maniatis, T. et al., *DNA Cloning 3: A Practical Approach*, (D. M. Glover ed.), 1995 (Table of Contents and Index only).

Marshall, M. "A Biological Approach to Water Quality Analysis Using 18S rDNA to Assess Aquatic Microbial Diversity across Spatial and Temporal Scales." Masters Thesis, Directed by Drs. Parke A. Rublee and Vincent C. Henrich, University of North Carolina at Greensboro, 2002, 52 pgs.

McCaig, A. E. et al., "Molecular Analysis of Bacterial Community Structure and Diversity in Unimproved and Improved Upland Grass Pastures," Appl. Environ. Microbiol., 1999, vol. 65, No. 4, 1721-1730.

Medlin, et al., "The Characterization of Enzymatically Amplified Eukaryotic 16S-like rRNA-Coding Regions," Gene, 1988, vol. 71, 491-499.

Methe, B. A. et al., "Diversity of Bacterial Communities in Adirondack Lakes: Do Species Assemblages Reflect Lake Water Chemistry?" Hydrobiologia, 1999, vol. 401, 77-95.

Moon-Van Der Staay, S. Y. et al., "Oceanic 18S rDNA Sequences from Picoplankton Reveal Unsuspected Eukaryotic Diversity," Nature, 2001, vol. 409, 607-610.

Needleman, S.B. et al., "A General Method Applicable to the Search for Similarities in the Amino Acid Sequence of Two Proteins," J. Mol. Biol., 1970, vol. 48, 443-453.

Nubel, U. et al., "Quantifying Microbial Diversity: Morphotypes, 16S rRNA Genes, and Carotenoids of Oxygenic Phototrophs in Microbial Mats," Appl. Environ. Microbiol., 1999, vol. 65, No. 2, 422-430.

Oldach, D. W. et al., "Heteroduplex Mobility Assay-Guided Sequence Discovery: Elucidation of the Small Subunit (18S) rDNA Sequences of Pfiesteria Piscicida and Related Dinoflagellates from Complex Algal Culture and Enviromental Sample DNA Pools," Proc. Natl. Acad. Sci. USA, 2000, vol. 97, No. 8, 4303-4308.

Oremland, R.S.et al., "The Ecology of Arsenic" Science, 2003, vol. 300, 939-943.

Pace, N. R. et al., "The Analysis of Natural Microbial Populations by Ribosomal RNA Sequences," Advances in Microbial Ecology, 1986, vol. 9, 1-55.

Paerl, H. W. et al., "Microbial Indicators of Aquatic Ecosystem Change: Current Applications to Eutrophication Studies," FEMS Microbiology Ecology, 2003, vol. 46, 233-246.

Pearson, W.R. et al., "Improved Tools for Biological Sequence Comparison," Proc. Natl. Acad. Sci. USA, 1988, vol. 85, 2444-2448.

Perez-Lopez, M. et al., "Assessment of Heavy Metal Contamination of Seawater and Marine Limpet, Patella Vulgata L., from Northwest Spain," Journal of Environmental Science and Health, Part A-Toxic/Hazardous Substances and Environmental Engineering, 2003, vol. A38, No. 12, 2845-2856.

Perna, et al., "Genome Sequence of Enterohaemorrhagic *Escherichia coli*0157:H7," Nature, 2001, vol. 409, 529-533.

Reysenbach, A. L. et al., "Differential Amplification of rRNA Genes by Polymerase Chain Reaction," Appl. Environ. Microbiol. 1992, vol. 58, No. 10, 3417-3418.

Rublee, P. A. et al., "PCR and FISH Detection Extends the Range of Pfiesteria piscicida in Estuarine Waters," Va. J. Sci., 1999, vol. 50, No. 4, 325-335.

Rublee, P. A. et al., "Use of Molecular Probes to Access Geographic Distribution of Pfiesteria Species," Environ. Health Perspectives, 2001, vol. 109 (Supplement 5), 765-767.

Rubtsov, P.M. et al., "The Structure of the Yeast Ribosomal RNA Genes. The Complete Nucleotide Sequence of the 18S Ribosomal RNA Gene from *Saccharomyces cereviciae*," Nucleic Acids Research, 1980, vol. 8, No. 23, 5779-5794.

Rudi, K. et al., "Application of Sequence-Specific Labeled 16S rRNA Gene Oligonucleotide Probes for Genetic Profiling of Cyanobacterial Abundance and Diversity by Array Hybridization," Appl. Environ. Microbiol., 2000, vol. 66, No. 9, 4004-4011.

Schonhuber, W. et al., "In Situ Identification of Cyanobacteria with Horseradish Peroxidase-Labeled, rRNA-Targeted Oligonucleotide Probes," Appl. Environ. Microbiol., 1999, vol. 65, No. 3, 1259-1267.

Shubert, L.E. (ed), *Algae as Ecological Indicators*. 1984, Academic Press, N.Y., Chapters 4,5,8,& 9.

Shi, W. et al., "Association of Microbial Community Composition and Activity with Lead, Chromium, and Hydrocarbon Contamination," Appl. Environ. Microbiol., 2002, vol. 68, No. 8, 3859-3866.

Siver, P.A. et al., "Century Changes in Connecticut, U.S.A., Lakes as Inferred from Siliceous Algal Remains and Their Relationships to Land-Use Change," Limnol. Oceanograph, 1999, vol. 44, No. 8, 1928-1935.

Smith, T.F. et al., "Comparison of Biosequences," Adv. Appl. Math., 1981, vol. 2, 482-489.

Sogin, M.L. et al., "Structural Diversity of Eukaryotic Small Subunit Ribosomal RNAs," Annals. NY Acad. Sci., 1987, vol. 503, 125-139.

Stoermer, et al., *The Diatoms: Applications for the Environmental and Earth Sciences*. 1999, Cambridge University Press, Cambridge, UK, Chapters 1-11, and 13-17.

Thompson, J.D. et al., "CLUSTAL W: Improving the Sensitivity of Progressive Multiple Sequence Alignment through Sequence Weighting, Position-Specific Gap Penalties and Weight Matrix Choice," Nucleic Acids Res., 1994, vol. 22, No. 22, 4673-4680.

Troesch, A. et al., "Mycobacterium Species Identification and Rifampin Resistance Testing with High-Density DNA Probe Arrays," J. Clin. Microbiol., 1999, vol. 37, No. 1, 49-55.

Venter, J. C. et al., "Environmental Genome Shotgun Sequencing of the Sargasso Sea," Science, 2004, vol. 304, 66-74.

Wang, G. et al., "Frequency of Formation of Chimeric Molecules as a Consequence of PCR Coamplification of 16S rRNA Genes from Mixed Bacterial Genomes," Appl. Environ. Microbiol., 1997, vol. 63, No. 12, 4645-4650.

Williams, R. B. et al., "Phytoplankton Production and Chlorophyll Concentration in the Beaufort Channel, North Carolina," Limnology and Oceanography, 1966, vol. 11, No. 1, 73-82.

Wu, L. et al., "Development and Evaluation of Functional Gene Arrays for Detection of Selected Genes in the Environment," Appl. Environ. Microbiol., 2001, vol. 67, No. 12, 5780-5790.

Xiao, L. et al., "Genetic Diversity within *Cryptosporidium parvum* and Related Cryptosporidum Species," Appl. Environ. Microbiol., 1999, vol. 65, No. 8, 3386-3391.

Entrez Nucleotide, NCBI Sequence, Accession No. V00348, (Definition)—*E. coli* ribosomal operon rrnB encoding the 16S ribosomal RNA. Also transfer RNA specific for Glu, 23S ribosomal RNA and two unidentified open reading frames. This sequence was obtained from the transducing phage lambda-rif-d 18 (BAMHI fragment). *J. Mol. Biol.* 148 (2), 107-127 1981. NCBI web page at http://www.ncbi.nlm.nih.gov/entrez/viewer.fcgi?db=nucleotide &val=2073407, as available via the Internet and printed Mar. 10, 2005.

Entrez Nucleotide, NCBI Sequence, Accession No. AY351647, (Definition)—Acanthamoeba mauritaniensis 18S ribosomal RNA gene, complete sequence. *Submitted (Jul. 25, 2003) by Department of Parasitology, Kyungpook National University School of Medicine*, 101 Dongin-dong, Chung-gu, Taegu 700-422, Korea (unpublished). NCBI web page at http://www.ncbi.nlm.nih.gov/entrez/viewer.fcgi?db=nucleotide&val=34305120, as available via the Internet and printed Mar. 10, 2005.

Entrez Nucleotide, NCBI Sequence, Accession No. V01335, (Definition)—Yeast 18S ribosomal RNA. *Nucleic Acids Res.*, 8(23), 5779-5794, 1980. NCBI web page at http://www.ncbi.nlm.nih.gov/entrez/viewer.fcgi?db=nucleotide&val=4347, as available via the Internet and printed Mar. 10, 2005.

Entrez Nucleotide, NCBI Sequence, Accession No. AF222998, (Definition)—*Cryptosporidium parvum* 18S ribosomal RNA gene and internal transcribed spacer 1, complete sequence; and 5.8S ribosomal RNA gene, partial sequence. *Submitted (Jan. 11, 2000) by Biomedical Sciences, Tufts University School of Veterinary Medicine*, 200 Westboro Road, North Grafton, MA 01536, USA (unpublished). NCBI web page at http://www.ncbi.nlm.nih.gov/entrez/viewer.fcgi?db=nucleotide&val=7530439, as available via the Internet and printed Mar. 10, 2005.

Entrez Nucleotide, NCBI Sequence, Accession No. AF111183, (Definition)—Cyclospora cayetanensis 18S ribosomal RNA gene, complete sequence. *Emerging Infect. Dis.* 5(5), 651-658, 1999. NCBI web page at http://www.ncbi.nlm.nih.gov/entrez/viewer. fcgi?db=nucleotide&val=4406385, as available via the Internet and printed Mar. 10, 2005.

Entrez Nucleotide, NCBI Sequence, Accession No. X65163, (Definition)—E. histolytica rRNA. *Nucleic Acids Res.* 21(8), 2011, 1993. NCBI web page at http://www.ncbi.nlm.nih.gov/entrez/viewer.fcgi?db=nucleotide&val=415339, as available via the Internet and printed Mar. 10, 2005.

Entrez Nucleotide, NCBI Sequence, Accession No. AF199449, (Definition)—*Giardia intestinalis* isolate Dog19 small subunit ribosomal RNA gene, partial sequence. *Parasitol. Today (Regul. Ed.)* 16(5), 210-213, 2000. NCBI web page at http://www.ncbi.nlm. nih.gov/entrez/viewer.fcgi?db=nucleotide&val=7008148, as available via the Internet and printed Mar. 10, 2005.

Entrez Nucleotide, NCBI Sequence, Accession No. AF106935,(Definition)—*Isospora belli* small subunit ribosomal RNA gene, complete sequence. *Parasitol. Res.* 86(8), 669-676, 2000. NCBI web page at http://www.ncbi.nlm.nih.gov/entrez/viewer.fcgi?db=nucleotide&val=4028606, as available via the Internet and printed Mar. 10, 2005.

Entrez Nucleotide, NCBI Sequence, Accession No. AY140647, (Definition)—*Microsporidium* sp. STF small subunit ribosomal RNA gene, partial sequence; internal transcribed spacer, complete sequence; and large subunit ribosomal RNA gene, partial sequence. *Submitted (Aug. 14, 2000) by Departement de Biologie, Universite de Fribourg*, chemin du Musee 10, Fribourg 1700, Switzerland (unpublished). NCBI web page at http://www.ncbi.nlm.nih.gov/entrez/viewer.fcgi?db=nucleotide&val=34391477, as available via the Internet and printed Mar. 10, 2005.

Entrez Nucleotide, NCBI Sequence, Accession No. AF338423, (Definition)—*Naegleria fowleri* 18S ribosomal RNA gene, partial sequence. *Dis. Aquat. Org.* 46(2), 115-121, 2001. NCBI web page at http://www.ncbi.nlm.nih.gov/entrez/viewer.fcgi?db=nucleotide &val=13398505, as available via the Internet and printed Mar. 10, 2005.

Entrez Nucleotide, NCBI Sequence, Accession No. AB116124, (Definition)—*Bacillus anthracis* gene for 16S ribosomal RNA, partial sequence, strain:S51. *Submitted (Jul. 31, 2003) by Akihiro Ohnishi, Tokyo University of Agriculture, Dept. of Fermentation Science*; Sakuragoaka 1-1-1, Setagaya-ku, Tokyo 156-8502, Japan, (direct submission). NCBI web page at http://www.ncbi.nlm.nih. gov/entrez/viewer.fcgi?db=nucleotide&val=33468788, as available via the Internet and printed Mar. 10, 2005.

Entrez Nucleotide, NCBI Sequence, Accession No. AF220149, (Definition)—*Brucella melitensis* ribosomal RNA operon C, complete sequence. *Gene* 255(1), 117-126, 2000. NCBI web page at http://www.ncbi.nlm.nih.gov/entrez/viewer.fcgi?db=nucleotide &val6979879, as available via the Internet and printed Mar. 10, 2005.

Entrez Nucleotide, NCBI Sequence, Accession No. AY305760, (Definition)—*Burkholderia mallei* strain 2000031063 16S ribosomal RNA gene, complete sequence. *J. Clin. Microbiol.*, 41(10), 4647-4654, 2003. NCBI web page at http://www.ncbi.nlm. nih.gov/entrez/viewer.fcgi?db=nucleotide&val=33286643, as available via the Internet and printed Mar. 10, 2005.

Entrez Nucleotide, NCBI Sequence, Accession No. AF550630, (Definition)—*Campylobacter jejuni* strain B99/206 16S ribosomal RNA gene, partial sequence. *J. Clin. Microbiol.*, 41(6), 2537-2549, 2003. NCBI web page at http://www.ncbi.nlm.nih.gov/entrez/viewer.fcgi?db=nucleotide&val=25229129, as available via the Internet and printed Mar. 10, 2005.

Entrez Nucleotide, NCBI Sequence, Accession No. AY334530, (Definition)—*Chlamydophila psittaci* clone cvCps2 16S ribosomal RNA gene, partial sequence. *Res. Microbiol.*, 153(9), 563-567, 2002. NCBI web page at http://www.ncbi.nlm.nih.gov/entrez/viewer/fcgi?db=nucleotide&val=33114016, as available via the Internet and printed Mar. 10. 2005.

Entrez Nucleotide, NCBI Sequence, Accession No. AY303799, (Definition)—*Clostridium botulinum* strain AIP 355.02 16S ribosomal RNA gene, partial sequence. *J. Clin. Microbiol.*, 42(1), 484-486, 2004. NCBI web page at http://www.ncbi.nlm.nih.gov/entrez/viewer.fcgi?db=nucleotide&val=31790293, as available via the Internet and printed Mar. 10, 2005.

Entrez Nucleotide, NCBI Sequence, Accession No. Y11502, (Definition)—*C. burnetti* ribosomal RNA, strain Nine Mile. *FEMS Immunol. Med. Microbiol.*, 20(2), 165-172, 1998. NCBI web page at http://www.ncbi.nlm.nih.gov/entrez/viewer.fcgi?db=nucleotide&val=1883009, as available via the Internet and printed Mar. 10, 2005.

Entrez Nucleotide, NCBI Sequence, Accession No. ABD35920, (Definition)—*Escherichia coli* 0157:H7 hemG, rrsA, ileT, alaT, rrlA, rrfA, mobB, mobA genes for protoporphyrin oxidase protein, 16S rRNA, isoleucine tRNA 1, alanine tRNA 1B, 23S rRNA, 5S rRNA, molybdopterin-guanine dinucleotide biosynthesis protein B, molybdopterin-guanine dinucleotide biosynthesis protein A, complete and partial cds. *Syst. Appl. Microbiol.*, 23(3), 315-324, 2000. NCBI web page at http://www.ncbi.nlm.nih.gov/entrez/viewer.fcgi?db=nucleotide&val=7415846, as available via the Internet and printed Mar. 10, 2005.

Entrez Nucleotide, NCBI Sequence, Accession No. X96964, (Definition)—*S. sonnei* 16S rRNA gene. *Mol. Cell. Probes*, 11(6), 427-432, 1997. NCBI web page at http:www.ncbi.nlm.nih.gov/entrez/viewer.fcgi?db=nucleotide&val=1255976, as available via the Internet and printed Mar. 10, 2005.

Entrez Nucleotide, NCBI Sequence, Accession No. AY243028, (Defintion)—*Francisella tularensis* strain 3523 16S ribosomal RNA gene, partial sequence. J. Med. Microbiol., 52(9), 839-842, 2003. NCBI web page at http://www.ncbi.nlm.nih.gov/entrez/viewer.fcgi?db=nucleotide&val=29570257, as available via the Internet and printed Mar. 10, 2005.

Entrez Nucleotide, NCBI Sequence, Accession No. AJ496383, (Definition)—*Legionella pneumophila* serogroup 6 partial 16S rRNA gene, avirulent mutant. *Submitted (Jul. 19, 2002) by Bacteriology and Medical Micology, National Institute of Health, Viale Regina Elena, 299, Rome 00161, Italy* (unpublished). NCBI web page at http://www.ncbi.nlm.nih.gov/entrez/viewer.fcgi?db=nucleotide&val=22080754, as available via the Internet and printed Mar. 10, 2005.

Entrez Nucleotide, NCBI Sequence, Accession No. Z12817, (Definition)—*L. interrogans* 16S ribosomal RNA. Submitted (Jun. 19, 1992) by Hookey J. V., Public Health Laboratory Service, Leptospira Reference Laboratory, Stonebow Road, Hereford, Herefordshire, United Kingdom, HR1 2ER. (direct submission). NCBI web page at http://www.ncbi.nlm.nih.gov/entrez/viewer.fcgi?db=nucleotide&val=44003, as available via the Internet and printed Mar. 10, 2005.

Entrez Nucleotide, NCBI Sequence, Accession No. AB117953, (Definition)—*Pseudomonas aeruginosa* gene for 16S rRNA, strain:WatG. *Submitted (Aug. 21, 2003) by Isao Yumoto, National Institute of Advanced Industrial Science and Technology, Institute for Biological Resources and Functions*; 2-17-2-1, Tsukisamu-Higashi, Toyohira-ku, Sapporo, Hokkaido 062-8517, Japan, (unpublished). NCBI web page at http://www.ncbi.nlm.nih.gov/entrez/viewer.fcgi?db=nucleotide&val=34146778, as available via the Internet and printed Mar. 10, 2005.

Entrez Nucleotide, NCBI Sequence, Accession No. M21789, (Definition)—*Rickettsia prowazekii* 16S ribosomal RNA. *J. Bacteriol.* 171(8), 4202-4206, 1989. NCBI web page at http://www.ncbi.nlm.nih.gov/entrez/viewer.fcgi?db=nucleotide&val=152479, as available via the Internet and printed Mar. 10, 2005.

Entrez Nucleotide, NCBI Sequence, Accession No. Z49264, (Definition)—*S. typhimurium* gene for 16S ribosomal RNA. *Int. J. Syst. Bacteriol.*, 47(4), 1253-1254, 1997. NCBI web page at http://www.ncbi.nlm.nih.gov/entrez/viewer.fcgi?db=nucleotide&val=2826774, as available via the Internet and printed Mar. 10, 2005.

Entrez Nucleotide, NCBI Sequence, Accession No. X76337, (Definition)—*V. cholerae* (CECT 514 T) 16S rRNA gene. *Int. J. Syst. Bacteriol.*, 44(2), 300-337, 1994. NCBI web page at http://www.ncbi.nlm.nih.gov/entrez/viewer.fcgi?db=nucleotide&val=531549, as available via the Internet and printed Mar. 10, 2005.

Entrez Nucleotide, NCBI Sequence, Accession No. AF366383, (Defintion)—*Yersinia pestis* 16S ribosomal RNA gene, partial sequence. *Antonie Van Leeuwenhoek*, 83(2), 125-133, 2003. NCBI web page at http://www.ncbi.nlm.nih.gov/entrez/viewer.fcgi?db=nucleotide&val=13991901, as available via the Internet and printed Mar. 10, 2005.

Entrez Nucleotide, NCBI Sequence, Accession No. AF406554, (Definition)—Arsenite-oxidizing bacterium MLHE-1 16S ribosomal RNA gene, partial sequence. *Appl. Environ. Microbiol.*, 68(10), 4795-4802, 2002. NCBI web page at http://www.ncbi.nlm.nih.gov/entrez/viewer.fcgi?db=nucleotide&val=23451034, as available via the Internet and printed Mar. 10, 2005.

Entrez Nucleotide, NCBI Sequence, Accession No. U46506, (Definition)—*Thiomicrospira* sp. CVO 16S ribosomal RNA gene, partial sequence. *Appl. Environ. Microbiol.*, 62(5), 1623-1629, 1996. NCBI web page at http://www.ncbi.nlm.nih.gov/entrez/viewer.fcgi?db=nucleotide&val=6995983, as available via the Internet and printed Mar. 10, 2005.

Entrez Nucleotide, NCBI Sequence, Accession No. Z24450, (Definition)—*D. longreachii* ribosomal RNA. *FEMS Microbiol. Lett.*, 113(1), 81-86, 1993. NCBI web page at http://www.ncbi.nlm.nih.gov/entrez/viewer.fcgi?db=nucleotide&val=415336, as available via the Internet and printed Mar. 10, 2005.

Entrez Nucleotide, NCBI Sequence, Accession No. AF064705, (Definition)—*Bacillus arsenicoselenatis* 16S ribosomal RNA gene, partial sequence. *Arch. Microbiol.*, 171(1), 19-30, 1998. NCBI web page at http://www.ncbi.nlm.nih.gov/entrez/viewer.fcgi?db=nucleotide&val=4038083, as available via the Internet and printed Mar. 10, 2005.

Entrez Nucleotide, NCBI Sequence, Accession No. AF233412, (Definition)—Uncultured human fecal bacterium HF74 16S ribosomal RNA gene, partial sequence. *Appl. Environ. Microbiol.*, 66(4), 1587-1594, 2000. NCBI web page at http://www.ncbi.nlm.nih.gov/entrez/viewer.fcgi?db=nucleotide&val=7385167, as available via the Internet and printed Mar. 10, 2005.

Entrez Nucleotide, NCBI Sequence, Accession No. AF233408, (Definition)—Uncultured human fecal bacterium HF8 16S ribosomal RNA gene, partial sequence. *Appl. Environ. Microbiol.*, 66(4), 1587-1594, 2000. NCBI web page at http://www.ncbi.nlm.nih.gov/entrez/viewer.fcgi?db=nucleotide&val=7385163, as available via the Internet and printed Mar. 10, 2005.

Entrez Nucleotide, NCBI Sequence, Accession No. AF233413, (Definition)—Uncultured human fecal bacterium HF10 16S ribosomal RNA gene, partial sequence. *Appl. Environ. Microbiol.*, 66(4), 1587-1594, 2000. NCBI web page at http://www.ncbi.nlm.nih.gov/entrez/viewer.fcgi?db=nucleotide&val=7385168, as available via the Internet and printed Mar. 10, 2005.

Entrez Nucleotide, NCBI Sequence, Accession No. AB091761, (Definition)—*Burkholderia capacia* gene for 16S rRNA, complete sequence. *Biosci. Biotechnol. Biochem.*, 67(9), 2026-2029, 2003. NCBI web page at http://www.ncbi.nlm.nih.gov/entrez/viewer.fcgi?db=nucleotide&val=23263363, as available via the Internet and printed Mar. 10, 2005.

Entrez Nucleotide, NCBI Sequence, Accession No. AF148556, (Definition)—*Burkholderia cepacia* genomovar III 16S ribosomal RNA gene, partial sequence, *Submitted (May 5, 1999) by Laboratorium voor Microbiologie, Universiteit Gent*, K.L. Ledeganckstraat 35, Gent 9000, Belgium, (unpublished). NCBI web page at http://www.ncbi.nlm.nih.gov/entrez/viewer.fcgi?db=nucleotide&val=8163584, as available via the Internet and printed Mar. 10, 2005.

Entrez Nucleotide, NCBI Sequence, Accession No. AE014075, (Definition)—*Eschierichia coli* CFT073 complete genome. *Proc. Natl. Acad. Sci. USA*, 99(26), 17020-17024, 2002. NCBI web page at http://www.ncbi.nlm.nih.gov/entrez/viewer.fcgi?db=nucleotide&val=26111730, as available via the Internet and printed Mar. 10, 2005.

Entrez Nucleotide, NCBI Sequence, Accession No. U00096, (Definition)—*Escherichia coli* K-12 MG1655 partial genome. *Science*, 277(5331), 1453-1474, 1997. NCBI web page at http://www.

ncbi.nlm.nih.gov/entrez/viewer.fcgi?db=nucleotide &val=48994873, as available via the Internet and printed Mar. 10, 2005.

Entrez Nucleotide, NCBI Sequence, Accession No. AJ301833, (Definition)—*Enterococcus gallinarm* 16S rRNA gene, strain LMG 13129. *Submitted (Nov. 22, 2000) by Ludwig W., TU Muenchen, Lehrstuhl fuer Mikrobiologie, Am Hochanger 4*, Germany (unpublished). NCBI web page at http://www.ncbi.nlm.nih.gov/entrez/viewer.fcgi?db=nucleotide&val=11342559, as available via the Internet and printed Mar. 10, 2005.

Entrez Nucleotide, NCBI Sequence, Accession No. AB091761, (Definition)—*Burkholderia cepacia* gene for 16S rRNA, complete sequence. *Biosci. Biotechnol. Biochem.*, 67(9), 2026-2029, 2003, NCBI web page at http://www.ncbi.nlm.nih.gov/entrez/viewer.fcgi?db=nucleotide&val=23263363, as available via the Internet and printed Mar. 10, 2005.

Entrez Nucleotide, NCBI Sequence, Accession No. AF222998, (Definition)—*Cryptosporidium parvum* 18S ribosomal RNA gene and internal transcribed spacer 1, complete sequence; and 5.8S ribosomal RNA gene, partial sequence. Submitted (Jan. 11, 2000) by Biomedical Sciences, Tufts University School of Veterinary Medicine, 200 Westboro Road, North Grafton, MA 01536, USA (Unpublished). NCBI web page at http://www.ncbi.nlm.nih.gov/entrez/viewer.fcgi?db=nucleotide&val=7530439, as available via the Internet and printed Aug. 9, 2005.

Entrez Nucleotide, NCBI Sequence, Accession No. AF351647, (Definition)—*Geochelone nigra* vicina isolate C8 NADH dehydrogenase subunit 4 (ND4) gene, partial cds; tRNA-His and tRNA-Ser genes, complete sequence; and tRNA-Leu gene, partial sequence; mitochondrial genes for mitochondrial products. Submitted (Feb. 21, 2001) by Center for Conservation and Research, Henry Doorly Zoo, 3701 South 10th Street, Omaha, NE 68107, USA. NCBI web page at http://www.ncbi.nlm.nih.gov/entrez/viewer.fcgi?db=nucleotide&val=22134763, as available via the Internet and printed Aug. 9, 2005.

Entrez Nucleotide, NCBI Sequence, Accession No. BA000007, (Definition)—*Escherichia coli* 0517:H7 DNA, complete genome (Could Not Print).

Entrez Nucleotide, NCBI Sequence, Accession No. NC_002695, (Definition)—*Escherichia coli* 0517:H7 DNA, complete genome (Could Not Print).

Henrich, V. C. et al., "Microarrays as Environmental Surveillance Tools in Aquatic Ecosystems: Microbial Community Detection from Lakewater Samples." 2004 ASLO Annual Meeting (Abstract and Slides).

Rublee, P. A. et al., "From Pfiesteria to Gene Arrays-Development Molecular Tools for Water Quality Assessment." EPA, Kansas City, MO. May 2002 (Abstract and Slides).

Rublee, P. A. et al., "Microarrays: New Tools for Water Surveillance." WRRI, Raleigh, NC, May 2003; Also presented at EPA, Research Triangle Park, NC, Mar. 2003 (Slides).

Rublee, P.A. et al., "Microarrays as Environmental Surveillance Tools in Aquatic Ecosystems: Will Nature Variation Preclude Practical Use?" 2004 ASLO Annual Meeting (Abstract and Slides).

Balser, L. M., "Determining Small-Scale Spatial, Temporal and Replicate Variability of Microbial Eukaryotic rDNA Libraries in an Aquatic Community," Masters Thesis, Directed by Dr. Parke A. Rublee, University of North Carolina at Greensboro, Dec. 2003.

"Characterization of Microbial Communities from Coastal Waters using Microarrays." Environmental Monitoring and Assessment, 2003, vol. 81, No. 1/3, 327-336 (Abstract).

O'Brien, W. J. et al. "The Limnology of Toolik Lake," Freshwaters of Alaska-Ecological Syntheses, A. M. Milner and M. W. Oswood (eds), Springer-Verlag Publishers, New York, NY, 1997.

Lemarchand, K. et al., "Molecular Biology and DNA Microarray Technology for Microbial Quality Monitoring of Water," Critical Reviews in Microbiology, 30:145-172, 2004.

Letowski, J. et al. "DNA Microarray Applications in Environmental Microbiology," Analytical Letters, vol. 36, No. 15, pp. 3165-3184, 2003.

Sebat, J. et al., "Metagenomic Profiling: Microarray Analysis of an Environmental Genomic Library," Applied and Environmental Microbiology, vol. 69, No. 8, pp. 4927-4934, 2003.

* cited by examiner

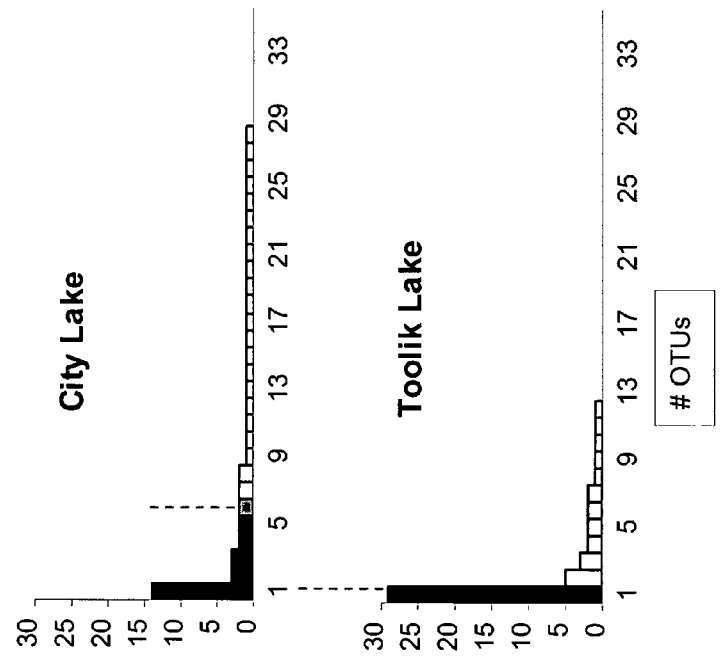
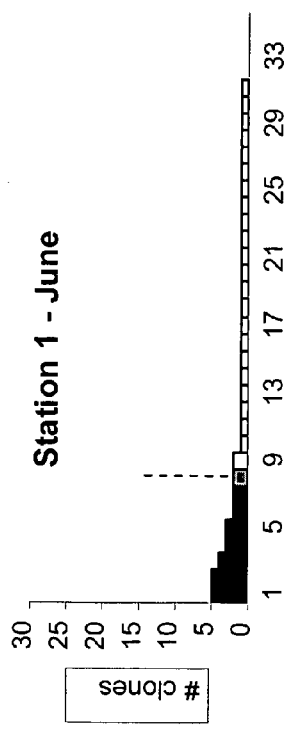
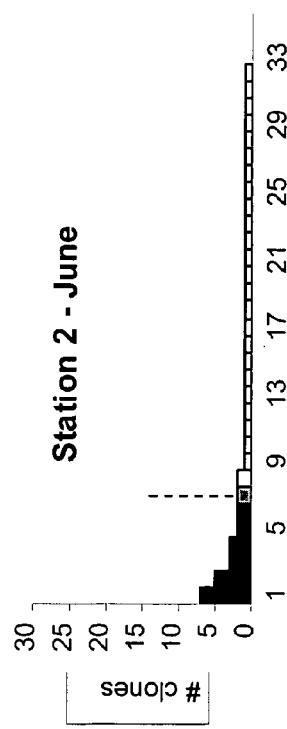
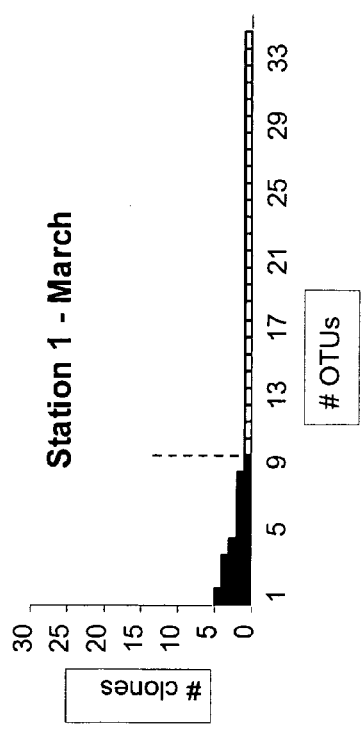
FIG. 3

FIG. 10 A-1

```
                 ....|....| ....|....| ....|....| ....|....| ....|....| ....|....|
                     5         15         25         35         45         55
E. coli          aaattgaaga gtttgatcat ggctcagatt gaacgctggc ggcaggccta acacatgcaa ....|....| ....|....| ....|....| ....|....| ....|....| ....|....|
                     65         75         85         95         105        115
E. coli          gtcgaacggt aacaggaaga agcttgcttc tttgctgacg agtggcggac gggtgagtaa ....|....| ....|....| ....|....| ....|....| ....|....| ....|....|
                     125        135        145        155        165        175
E. coli          tgtctgggaa actgcctgat ggagggggat aactactgga aacggtagct aataccgcat ....|....| ....|....| ....|....| ....|....| ....|....| ....|....|
                     185        195        205        215        225        235
E. coli          aacgtcgcaa gaccaaagag ggggaccttc gggcctcttg ccatcggatg tgcccagatg ....|....| ....|....| ....|....| ....|....| ....|....| ....|....|
                     245        255        265        275        285        295
E. coli          ggattagcta gtaggtgggg taacggctca cctaggcgac gatccctagc tggtctgaga ....|....| ....|....| ....|....| ....|....| ....|....| ....|....|
                     305        315        325        335        345        355
E. coli          ggatgaccag ccacactgga actgagacac ggtccagact cctacgggag gcagcagtgg ....|....| ....|....| ....|....| ....|....| ....|....| ....|....|
                     365        375        385        395        405        415
E. coli          ggaatattgc acaatgggcg caagcctgat gcagccatgc cgcgtgtatg aagaaggcct ....|....| ....|....| ....|....| ....|....| ....|....| ....|....|
                     425        435        445        455        465        475
E. coli          tcgggttgta aagtactttc agcggggagg aagggagtaa agttaatacc tttgctcatt ....|....| ....|....| ....|....| ....|....| ....|....| ....|....|
                     485        495        505        515        525        535
E. coli          gacgttaccc gcagaagaag caccggctaa ctccgtgcca gcagccgcgg taatacggag ....|....| ....|....| ....|....| ....|....| ....|....| ....|....|
                     545        555        565        575        585        595
E. coli          ggtgcaagcg ttaatcggaa ttactgggcg taaagcgcac gcaggcggtt tgttaagtca ....|....| ....|....| ....|....| ....|....| ....|....| ....|....|
                     605        615        625        635        645        655
E. coli          gatgtgaaat ccccgggctc aacctgggaa ctgcatctga tactggcaag cttgagtctc ....|....| ....|....| ....|....| ....|....| ....|....| ....|....|
                     665        675        685        695        705        715
E. coli          gtagaggggg gtagaattcc aggtgtagcg gtgaaatgcg tagagatctg gaggaatacc ....|....| ....|....| ....|....| ....|....| ....|....| ....|....|
                     725        735        745        755        765        775
E. coli          ggtggcgaag gcggccccct ggacgaagac tgacgctcag gtgcgaaagc gtggggagca ....|....| ....|....| ....|....| ....|....| ....|....| ....|....|
                     785        795        805        815        825        835
E. coli          aacaggatta gataccctgg tagtccacgc cgtaaacgat gtcgacttgg aggttgtgcc ....|....| ....|....| ....|....| ....|....| ....|....| ....|....|
                     845        855        865        875        885        895
E. coli          cttgaggcgt ggcttccgga gctaacgcgt taagtcgacc gcctggggag tacggccgca
```

FIG. 10A-2

```
            ....|....| ....|....| ....|....| ....|....| ....|....| ....|....|
               905        915        925        935        945        955
E. coli     aggttaaaac tcaaatgaat tgacgggggc ccgcacaagc ggtggagcat gtggtttaat ....|....| ....|....| ....|....| ....|....| ....|....| ....|....|
               965        975        985        995       1005       1015
E. coli     tcgatgcaac gcgaagaacc ttacctggtc ttgacatcca cggaagtttt cagagatgag ....|....| ....|....| ....|....| ....|....| ....|....| ....|....|
              1025       1035       1045       1055       1065       1075
E. coli     aatgtgcctt cgggaaccgt gagacaggtg ctgcatggct gtcgtcagct cgtgttgtga ....|....| ....|....| ....|....| ....|....| ....|....| ....|....|
              1085       1095       1105       1115       1125       1135
E. coli     aatgttgggt taagtcccgc aacgagcgca acccttatcc tttgttgcca gcggtccggc ....|....| ....|....| ....|....| ....|....| ....|....| ....|....|
              1145       1155       1165       1175       1185       1195
E. coli     cgggaactca aaggagactg ccagtgataa actggaggaa ggtggggatg acgtcaagtc ....|....| ....|....| ....|....| ....|....| ....|....| ....|....|
              1205       1215       1225       1235       1245       1255
E. coli     atcatggccc ttacgaccag ggctacacac gtgctacaat ggcgcataca agagaagcg ....|....| ....|....| ....|....| ....|....| ....|....| ....|....|
              1265       1275       1285       1295       1305       1315
E. coli     acctcgcgag agcaagcgga cctcataaag tgcgtcgtag tccggattgg agtctgcaac ....|....| ....|....| ....|....| ....|....| ....|....| ....|....|
              1325       1335       1345       1355       1365       1375
E. coli     tcgactccat gaagtcggaa tcgctagtaa tcgtggatca gaatgccacg gtgaatacgt ....|....| ....|....| ....|....| ....|....| ....|....| ....|....|
              1385       1395       1405       1415       1425       1435
E. coli     tcccgggcct tgtacacacc gcccgtcaca ccatgggagt gggttgcaaa agaagtaggt ..
E. coli     ag
```

*E. coli* 16S rRNA gene (SEQ ID NO: 317)

FIG. 10B-1

```
              ....|....|  ....|....|  ....|....|  ....|....|  ....|....|  ....|....|
                  5           15          25          35          45          55
S. cerevis    tatctggttg  atcctgccag  tagtcatatg  cttgtctcaa  agattaagcc  atgcatgtct ....|....|  ....|....|  ....|....|  ....|....|  ....|....|  ....|....|
                 65          75          85          95         105         115
S. cerevis    aagtataagc  aatttataca  gtgaaactgc  gaatggctca  ttaaatcagt  tatcgtttat ....|....|  ....|....|  ....|....|  ....|....|  ....|....|  ....|....|
                125         135         145         155         165         175
S. cerevis    ttgatagttc  ctttactaca  tggtataacc  gtggtaattc  tagagctaat  acatgcttaa ....|....|  ....|....|  ....|....|  ....|....|  ....|....|  ....|....|
                185         195         205         215         225         235
S. cerevis    aatctcgacc  ctttggaaga  gatgtattta  ttagataaaa  aatcaatgtc  ttcgcactct ....|....|  ....|....|  ....|....|  ....|....|  ....|....|  ....|....|
                245         255         265         275         285         295
S. cerevis    ttgatgattc  ataataactt  ttcgaatcgc  atggccttgt  gctggcgatg  gttcattcaa ....|....|  ....|....|  ....|....|  ....|....|  ....|....|  ....|....|
                305         315         325         335         345         355
S. cerevis    atttctgccc  tatcaacttt  cgatggtagg  atagtggcct  accatggttt  caacgggtaa ....|....|  ....|....|  ....|....|  ....|....|  ....|....|  ....|....|
                365         375         385         395         405         415
S. cerevis    cggggaataa  gggttcgatt  ccggagaggg  agcctgagaa  acggctacca  catccaagga ....|....|  ....|....|  ....|....|  ....|....|  ....|....|  ....|....|
                425         435         445         455         465         475
S. cerevis    aggcagcagg  cgcgcaaatt  acccaatcct  aattcaggga  ggtagtgaca  ataaataacg ....|....|  ....|....|  ....|....|  ....|....|  ....|....|  ....|....|
                485         495         505         515         525         535
S. cerevis    atacagggcc  cattcgggtc  ttgtaattgg  aatgagtaca  atgtaaatac  cttaacgagg ....|....|  ....|....|  ....|....|  ....|....|  ....|....|  ....|....|
                545         555         565         575         585         595
S. cerevis    aacaattgga  gggcaagtct  ggtgccagca  gccgcggtaa  ttccagctcc  aatagcgtat ....|....|  ....|....|  ....|....|  ....|....|  ....|....|  ....|....|
                605         615         625         635         645         655
S. cerevis    attaaagttg  ttgcagttaa  aaagctcgta  gttgaacttt  gggcccggtt  ggccggtccg ....|....|  ....|....|  ....|....|  ....|....|  ....|....|  ....|....|
                665         675         685         695         705         715
S. cerevis    atttttttcgt  gtactggatt  tccaacgggg  cctttccttc  tggctaacct  tgagtccttg ....|....|  ....|....|  ....|....|  ....|....|  ....|....|  ....|....|
                725         735         745         755         765         775
S. cerevis    tggctcttgg  cgaaccagga  cttttacttt  gaaaaaatta  gagtgttcaa  agcaggcgta ....|....|  ....|....|  ....|....|  ....|....|  ....|....|  ....|....|
                785         795         805         815         825         835
S. cerevis    ttgctcgaat  atattagcat  ggaataatag  aataggacgt  ttggttctat  tttgttggtt ....|....|  ....|....|  ....|....|  ....|....|  ....|....|  ....|....|
                845         855         865         875         885         895
S. cerevis    tctaggacca  tcgtaatgat  taatagggac  ggtcggggc  atcggtattc  aattgtcgag
```

FIG. 10B-2

```
              ....|....|  ....|....|  ....|....|  ....|....|  ....|....|  ....|....|
                  905         915         925         935         945         955
S. cerevis    gtgaaattct  tggatttatt  gaagactaac  tactgcgaaa  gcatttgcca  aggacgtttt ....|....|  ....|....|  ....|....|  ....|....|  ....|....|  ....|....|
                  965         975         985         995        1005        1015
S. cerevis    cattaatcaa  gaacgaaagt  taggggatcg  aagatgatct  ggtaccgtcg  tagtcttaac ....|....|  ....|....|  ....|....|  ....|....|  ....|....|  ....|....|
                 1025        1035        1045        1055        1065        1075
S. cerevis    cataaactat  gccgactaga  tcgggtggtg  ttttttttaat gacccactcg  gtaccttacg ....|....|  ....|....|  ....|....|  ....|....|  ....|....|  ....|....|
                 1085        1095        1105        1115        1125        1135
S. cerevis    agaaatcaaa  gtctttgggt  tctgggggga  gtatggtcgc  aaggctgaaa  cttaaaggaa ....|....|  ....|....|  ....|....|  ....|....|  ....|....|  ....|....|
                 1145        1155        1165        1175        1185        1195
S. cerevis    ttgacggaag  ggcaccacta  ggagtggagc  ctgcggctaa  tttgactcaa  cacgggaaa ....|....|  ....|....|  ....|....|  ....|....|  ....|....|  ....|....|
                 1205        1215        1225        1235        1245        1255
S. cerevis    ctcaccaggt  ccagacacaa  taaggattga  cagattgaga  gctctttctt  gatttgtgg ....|....|  ....|....|  ....|....|  ....|....|  ....|....|  ....|....|
                 1265        1275        1285        1295        1305        1315
S. cerevis    gtggtggtgc  atggccgttt  ctcagttggt  ggagtgattt  gtctgcttaa  ttgcgataac ....|....|  ....|....|  ....|....|  ....|....|  ....|....|  ....|....|
                 1325        1335        1345        1355        1365        1375
S. cerevis    gaacgagacc  ttaacctact  aaatagtggt  gctagcattt  gctggttatc  cacttcttag ....|....|  ....|....|  ....|....|  ....|....|  ....|....|  ....|....|
                 1385        1395        1405        1415        1425        1435
S. cerevis    agggactatc  ggtttcaagc  cgatggaagt  ttgaggcaat  aacaggtctg  tgatgcccctt ....|....|  ....|....|  ....|....|  ....|....|  ....|....|  ....|....|
                 1445        1455        1465        1475        1485        1495
S. cerevis    agaacgttct  gggccgcacg  cgcgctacac  tgacggagcc  agcgagtcta  accttggccg ....|....|  ....|....|  ....|....|  ....|....|  ....|....|  ....|....|
                 1505        1515        1525        1535        1545        1555
S. cerevis    agaggtcttg  gtaatcttgt  gaaactccgt  cgtgctgggg  atagagcatt  gtaattattg ....|....|  ....|....|  ....|....|  ....|....|  ....|....|  ....|....|
                 1565        1575        1585        1595        1605        1615
S. cerevis    ctcttcaacg  aggaattcct  agtaagcgca  agtcatcagc  ttgcgttgat  tacgtccctg ....|....|  ....|....|  ....|....|  ....|....|  ....|....|  ....|....|
                 1625        1635        1645        1655        1665        1675
S. cerevis    ccctttgtac  acaccgcccg  tcgctagtac  cgattgaatg  gcttagtgag  gcctcaggat ....|....|  ....|....|  ....|....|  ....|....|  ....|....|  ....|....|
                 1685        1695        1705        1715        1725        1735
S. cerevis    ctgcttagag  aaggggggcaa ctccatctca  gagcggagaa  tttggacaaa  cttggtcatt ....|....|  ....|....|  ....|....|  ....|....|  ....|....|  ....|...
                 1745        1755        1765        1775        1785        1795
S. cerevis    tagaggaact  aaaagtcgta  acaaggtttc  cgtaggtgaa  cctgcggaag  gatcatta
```

*S. cerevisiae* 18S rRNA gene (SEQ ID NO: 318)

FIG. 10C-1

V1 region (SEQ ID NO:319)

```
                                                                |....|....|
                                                                        55
E. coli                                                         a acacatgcaa ....|....| ....|....| ....|....| ....|....| ....|....| ....|....|
            65         75         85         95        105        115
E. coli gtcgaacggt aacaggaaga agcttgcttc tttgctgacg agtggcggac gggtgagtaa ....|....| ....|....| ....|....| ....|....| ....|....| ....|....|
           125        135        145        155        165        175
E. coli tgtctgggaa actgcctgat ggaggggat
```

V2 region (SEQ ID NO: 320)

```
                                                    |....|....| ....|....|
                                                        165         175
E. coli                                             a aacggtagct aataccgcat ....|....| ....|....| ....|....| ....|....| ....|....| ....|....|
           185        195        205        215        225        235
E. coli aacgtcgcaa gaccaaagag ggggaccttc gggcctcttg ccatcggatg tgcccagatg ....|....| ....|....| ....|....| ....|....| ....|....| ....|....|
           245        255        265        275        285        295
E. coli ggattagcta
```

V3 region (SEQ ID NO: 321)

```
        ....|....| ....|....| ....|....| ....|....| ....|....| ....|....|
           435        445        455        465        475
E. coli a aagtactttc agcggggagg aaggagtaa agttaatacc tttgctcatt ....|....| ....|....| ....|....| ....|....| ....|....| ....|....|
           485        495        505        515        525        535
E. coli gacgttaccc gcagaagaag caccggctaa
```

FIG. 10C-2

V4 region (SEQ ID NO: 322)

```
                                          |....|....| ....|....|
                                              825        835
E. coli                                   t gtcgacttgg aggttgtgcc ....|....| ....|....| ....|....| ....|....| ....|....| ....|....|
            845        855        865        875        885        895
E. coli     cttgaggcgt ggcttccgga gctaacgcgt taagtcgacc
```

V6 region (SEQ ID NO: 323)

```
                                          |....|....| ....|....| ....|....| ....|....|
                                              1105       1115       1125       1135
E. coli                                   c aacgagcgca acccttatcc tttgttgcca gcggtccggc ....|....| ....|....| ....|....| ....|....| ....|....| ....|....|
            1145       1155       1165       1175       1185       1195
E. coli     cgggaactca aaggagactg
```

FIG. 10D-1

V1 plus flanking region (SEQ ID NO: 324)

```
                                                              |....|....|
                                                                      55
S. cerevis                                                    c atgcatgtct ....|....| ....|....| ....|....| ....|....| ....|....| ....|....|
               65         75         85         95        105        115
S. cerevis aagtataagc aatttataca gtgaaactgc gaatggctca ttaaatcagt tatcgtttat ....|....| ....|....| ....|....| ....|....| ....|....| ....|....|
              125        135        145        155        165        175
S. cerevis ttgatagttc ctttactaca tggtataacc gtggtaattc tagagctaat acatgcttaa ....|....| ....|....| ....|....| ....|....| ....|....| ....|....|
              185        195        205        215        225        235
S. cerevis aatctcgacc ctttggaaga gatgtattta ttagataaaa aatcaatgtc ttcgcactct ....|....| ....|....| ....|....| ....|....| ....|....| ....|....|
              245        255        265        275        285        295
S. cerevis ttgatgattc ataataactt ttcgaatcgc atggccttgt gctggcgatg gttcattcaa ....|....| ....|....| ....|....| ....|....| ....|....| ....|....|
              305        315        325        335        345        355
S. cerevis atttctgccc tatcaacttt cgatggtagg atagtggcct accatggttt caacgggtaa ....|....| ....|....| ....|....| ....|....| ....|....| ....|....|
              365        375        385        395        405        415
S. cerevis cggggaataa gggttcgatt ccggagaggg agcctgagaa acggctacca catccaagga ....|....| ....|....| ....|....| ....|....| ....|....| ....|....|
              425        435        445        455        465        475
S. cerevis aggcagcagg cgcgcaaatt acccaatcct aattcaggga ggtagtgaca ataaataacg ....|....| ....|....| ....|....| ....|....| ....|....| ....|....|
              485        495        505        515        525        535
S. cerevis atacagggcc cattcgggtc ttgtaattgg aatgagtaca atgtaaatac cttaacgagg ....|....| ....|....| ....|....| ....|....| ....|....| ....|....|
              545        555        565        575        585        595
S. cerevis aacaattgga
```

FIG. 10D-2

V2 region (SEQ ID NO: 325)

```
S. cerevis                                                                    t ....|....| ....|....| ....|....| ....|....| ....|....| ....|....|
             605        615        625        635        645        655
S. cerevis   attaaagttg ttgcagttaa aaagctcgta gttgaacttt gggcccggtt ggccggtccg ....|....| ....|....| ....|....| ....|....| ....|....| ....|....|
             665        675        685        695        705        715
S. cerevis   attttttcgt gtactggatt tccaacgggg cctttccttc tggctaacct tgagtccttg ....|....| ....|....| ....|....| ....|....| ....|....| ....|....|
             725        735        745        755        765        775
S. cerevis   tggctcttgg cgaaccagga cttttacttt gaaaaaatta gagtgttcaa agcaggcgta ....|....| ....|....| ....|....| ....|....| ....|....| ....|....|
             785        795        805        815        825        835
S. cerevis   ttgctcgaat atattagcat
```

V3 region (SEQ ID NO: 326)

```
                         |  ....|....| ....|....| ....|....| ....|....|
                            805        815        825        835
S. cerevis                t ggaataatag aataggacgt ttggttctat tttgttggtt ....|....| ....|....| ....|....| ....|....| ....|....| ....|....|
             845        855        865        875        885        895
S. cerevis   tctaggacca tcgtaatgat taatagggac
```

V4 region (SEQ ID NO: 327)

```
                                                     |  ....|....| ....|....|
                                                        1005       1015
S. cerevis                                            t ggtaccgtcg tagtcttaac ....|....| ....|....| ....|....| ....|....| ....|....| ....|....|
             1025       1035       1045       1055       1065       1075
S. cerevis   cataaactat gccgactaga tcgggtggtg ttttttttaat gacccactcg gtaccttacg ....|....| ....|....| ....|....| ....|....| ....|....| ....|....|
             1085       1095       1105       1115       1125       1135
S. cerevis   agaaatcaaa gtctttgggt
```

V5 region (SEQ ID NO: 328)

```
                                        |  ....|....| ....|....| ....|....|
                                           1355       1365       1375
S. cerevis                               t gctagcattt gctggttatc cacttcttag ....|....| ....|....| ....|....| ....|....| ....|....| ....|....|
             1385       1395       1405       1415       1425       1435
S. cerevis   agggactatc ggtttcaagc cgatggaagt ttgaggcaat aacaggtctg tgatgccctt ....|....| ....|....| ....|....| ....|....| ....|....| ....|....|
             1445       1455       1465       1475       1485       1495
S. cerevis   agaacgttct
```

Fig. 11A-1     Fig. 11A-2     Fig. 11B
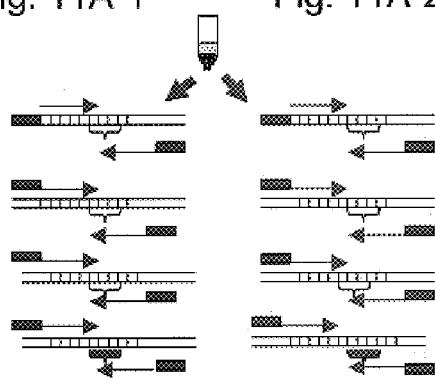

SEQUENCE LISTING

<160> NUMBER OF SEQ ID NOS: 328

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
agagtttgat cctggctcag                                          20

<210> SEQ ID NO 2
<211> LENGTH: 20
<212> TYPE: DNA
<213> ORGANISM: Artificial Sequence
<220> FEATURE:

<223> OTHER INFORMATION: Synthetic

<400> SEQUENCE: 2
aaggaggtga tccagccgca                                               20

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
aacctggttg atcctgccag t                                             21

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
tgatccttct gcaggttcac ctac                                          24

<210> SEQ ID NO 5
<211> LENGTH: 50
<212> TYPE: DNA
<213> ORGANISM: Artificial Sequence
<220> FEATURE:
<223> OTHER INFORMATION: Synthetic

<400> SEQUENCE: 5
actaactcaa tagcaggaac gggaatccag aaggagggga cgggcgggcc              50

<210> SEQ ID NO 6
<211> LENGTH: 50
<212> TYPE: DNA
<213> ORGANISM: Artificial Sequence
<220> FEATURE:
<223> OTHER INFORMATION: Synthetic

<400> SEQUENCE: 6
gatttctcat aaggtgctga aggagtaagg aacaacctcc aatctctagt              50

<210> SEQ ID NO 7
<211> LENGTH: 50
<212> TYPE: DNA
<213> ORGANISM: Artificial Sequence
<220> FEATURE:
<223> OTHER INFORMATION: Synthetic

<400> SEQUENCE: 7
agttccggaa caccaacgca cgcagcgaag cgcggaaggc taccggaaga              50

<210> SEQ ID NO 8
<211> LENGTH: 50
<212> TYPE: DNA
<213> ORGANISM: Artificial Sequence
<220> FEATURE:
<223> OTHER INFORMATION: Synthetic

<400> SEQUENCE: 8
gaaatgtctt attgacatcc cctcagcatt gtcccatgct tgaatattca              50

<210> SEQ ID NO 9
<211> LENGTH: 50
<212> TYPE: DNA
<213> ORGANISM: Artificial Sequence
<220> FEATURE:
<223> OTHER INFORMATION: Synthetic

<400> SEQUENCE: 9
cccacgcggc gggtccaacg ggcctgcctg gagcgctccc gtttcctcgt        50

<210> SEQ ID NO 10
<211> LENGTH: 50
<212> TYPE: DNA
<213> ORGANISM: Artificial Sequence
<220> FEATURE:
<223> OTHER INFORMATION: Synthetic

<400> SEQUENCE: 10
gaatttcacc acgtacacac ccctaagggc ggactggctg cttccagcag        50

<210> SEQ ID NO 11
<211> LENGTH: 50
<212> TYPE: DNA
<213> ORGANISM: Artificial Sequence
<220> FEATURE:
<223> OTHER INFORMATION: Synthetic

<400> SEQUENCE: 11
ctttatcatc ggactcgccc ctggccagcg ctttcgcctc tgtcgctcct        50

<210> SEQ ID NO 12
<211> LENGTH: 50
<212> TYPE: DNA
<213> ORGANISM: Artificial Sequence
<220> FEATURE:
<223> OTHER INFORMATION: Synthetic

<400> SEQUENCE: 12
cctccaacca tctcctgatg gaactagtta ccccgtaaac actcttaggt        50

<210> SEQ ID NO 13
<211> LENGTH: 50
<212> TYPE: DNA
<213> ORGANISM: Artificial Sequence
<220> FEATURE:
<223> OTHER INFORMATION: Synthetic

<400> SEQUENCE: 13
acggagacaa acaagcacca acacaagtga agggcacgtt gctccaacca        50

<210> SEQ ID NO 14
<211> LENGTH: 50
<212> TYPE: DNA
<213> ORGANISM: Artificial Sequence
<220> FEATURE:
<223> OTHER INFORMATION: Synthetic

<400> SEQUENCE: 14
caagcagaaa ggcacgcgcg caccgtccaa ccagaggctg acagttcaca        50

<210> SEQ ID NO 15
<211> LENGTH: 50
<212> TYPE: DNA
<213> ORGANISM: Artificial Sequence
<220> FEATURE:
<223> OTHER INFORMATION: Synthetic

```
<400> SEQUENCE: 15
gcacgcgcat gccgtccgac cagaggccga cagcccacac gcgcccaaaa          50

<210> SEQ ID NO 16
<211> LENGTH: 50
<212> TYPE: DNA
<213> ORGANISM: Artificial Sequence
<220> FEATURE:
<223> OTHER INFORMATION: Synthetic

<400> SEQUENCE: 16
taactgtccc tgatgggact agtagggatt ggtttaaagc ctctccctag          50

<210> SEQ ID NO 17
<211> LENGTH: 50
<212> TYPE: DNA
<213> ORGANISM: Artificial Sequence
<220> FEATURE:
<223> OTHER INFORMATION: Synthetic

<400> SEQUENCE: 17
tctcagacgg atgaacgcct atacctcgac cggagccgct gtacaaacgc          50

<210> SEQ ID NO 18
<211> LENGTH: 50
<212> TYPE: DNA
<213> ORGANISM: Artificial Sequence
<220> FEATURE:
<223> OTHER INFORMATION: Synthetic

<400> SEQUENCE: 18
acctaatgcc acacagattc cacccaagga tggacgagct gcccaagtac          50

<210> SEQ ID NO 19
<211> LENGTH: 50
<212> TYPE: DNA
<213> ORGANISM: Artificial Sequence
<220> FEATURE:
<223> OTHER INFORMATION: Synthetic

<400> SEQUENCE: 19
ccatctgcgc ctcaacatgc aggtaaatcg taaagaaaag gccaaatagc          50

<210> SEQ ID NO 20
<211> LENGTH: 50
<212> TYPE: DNA
<213> ORGANISM: Artificial Sequence
<220> FEATURE:
<223> OTHER INFORMATION: Synthetic

<400> SEQUENCE: 20
gtatcacacc agggaggtta ttgaacgcag accacctagg taacacctaa          50

<210> SEQ ID NO 21
<211> LENGTH: 50
<212> TYPE: DNA
<213> ORGANISM: Artificial Sequence
<220> FEATURE:
<223> OTHER INFORMATION: Synthetic

<400> SEQUENCE: 21
aaggatgctt tcaggcactg atcgcgcaca ctgaggtggg aagtgccgtt          50

<210> SEQ ID NO 22
<211> LENGTH: 50
```

```
<212> TYPE: DNA
<213> ORGANISM: Artificial Sequence
<220> FEATURE:
<223> OTHER INFORMATION: Synthetic

<400> SEQUENCE: 22
taagtgcaac gggatcctca tgcagaaaga cccgagcctg ccgtccgacc         50

<210> SEQ ID NO 23
<211> LENGTH: 50
<212> TYPE: DNA
<213> ORGANISM: Artificial Sequence
<220> FEATURE:
<223> OTHER INFORMATION: Synthetic

<400> SEQUENCE: 23
aaagtaaacc tgccagcaca gacggacact cggcgaagag cacccgcctg         50

<210> SEQ ID NO 24
<211> LENGTH: 50
<212> TYPE: DNA
<213> ORGANISM: Artificial Sequence
<220> FEATURE:
<223> OTHER INFORMATION: Synthetic

<400> SEQUENCE: 24
ttaatgccag atatgctctc cccgaggatg gctgcagaca catagtacag         50

<210> SEQ ID NO 25
<211> LENGTH: 50
<212> TYPE: DNA
<213> ORGANISM: Artificial Sequence
<220> FEATURE:
<223> OTHER INFORMATION: Synthetic

<400> SEQUENCE: 25
agtcgaccag ttctgaccca tgaggccgac cggctgagct cactctgaac         50

<210> SEQ ID NO 26
<211> LENGTH: 50
<212> TYPE: DNA
<213> ORGANISM: Artificial Sequence
<220> FEATURE:
<223> OTHER INFORMATION: Synthetic

<400> SEQUENCE: 26
tcaaacctga ttcaaacccg tatgggtcga tcggtcgtcc tcagcagaaa         50

<210> SEQ ID NO 27
<211> LENGTH: 50
<212> TYPE: DNA
<213> ORGANISM: Artificial Sequence
<220> FEATURE:
<223> OTHER INFORMATION: Synthetic

<400> SEQUENCE: 27
tggtaggcta ccactgcgca tccacaagga ggcagaaact agccaaccag         50

<210> SEQ ID NO 28
<211> LENGTH: 50
<212> TYPE: DNA
<213> ORGANISM: Artificial Sequence
<220> FEATURE:
<223> OTHER INFORMATION: Synthetic

<400> SEQUENCE: 28
```
gcttcatgca ggagcatctc agcatccagt gttgggacca ggacatactg        50

<210> SEQ ID NO 29
<211> LENGTH: 50
<212> TYPE: DNA
<213> ORGANISM: Artificial Sequence
<220> FEATURE:
<223> OTHER INFORMATION: Synthetic

<400> SEQUENCE: 29
gttatgattc tatctcaagg aggagcgtcc tgtgctctcc cacttcactc        50

<210> SEQ ID NO 30
<211> LENGTH: 50
<212> TYPE: DNA
<213> ORGANISM: Artificial Sequence
<220> FEATURE:
<223> OTHER INFORMATION: Synthetic

<400> SEQUENCE: 30
tccagaaggt gaggccgacg caaagagtac tcaccgctag gtggaccctc        50

<210> SEQ ID NO 31
<211> LENGTH: 50
<212> TYPE: DNA
<213> ORGANISM: Artificial Sequence
<220> FEATURE:
<223> OTHER INFORMATION: Synthetic

<400> SEQUENCE: 31
acagtaaagg acgcaggtcc ggacgccgac aagtgaatgc cgacgccttc        50

<210> SEQ ID NO 32
<211> LENGTH: 50
<212> TYPE: DNA
<213> ORGANISM: Artificial Sequence
<220> FEATURE:
<223> OTHER INFORMATION: Synthetic

<400> SEQUENCE: 32
tctctagaag gatgcccaac ccgcaccggc actcacaggc caaaaaggcc        50

<210> SEQ ID NO 33
<211> LENGTH: 50
<212> TYPE: DNA
<213> ORGANISM: Artificial Sequence
<220> FEATURE:
<223> OTHER INFORMATION: Synthetic

<400> SEQUENCE: 33
cgaagacgga tgactaacta tatactgacg taagccagca tataaatagc        50

<210> SEQ ID NO 34
<211> LENGTH: 50
<212> TYPE: DNA
<213> ORGANISM: Artificial Sequence
<220> FEATURE:
<223> OTHER INFORMATION: Synthetic

<400> SEQUENCE: 34
cacaattaag tgcaacggga tcctcatgca gaaagacccg agcctgccgt        50

<210> SEQ ID NO 35
<211> LENGTH: 50
<212> TYPE: DNA
<213> ORGANISM: Artificial Sequence
<220> FEATURE:
<223> OTHER INFORMATION: Synthetic

<400> SEQUENCE: 35
tattaacgca ctacgccctg gaaggatgct ttcaggcact gatcgcgcac        50

<210> SEQ ID NO 36
<211> LENGTH: 50
<212> TYPE: DNA
<213> ORGANISM: Artificial Sequence
<220> FEATURE:
<223> OTHER INFORMATION: Synthetic

<400> SEQUENCE: 36
acagctacca ccaccctaag gtggggaggt catcccgatc agagattcaa        50

<210> SEQ ID NO 37
<211> LENGTH: 50
<212> TYPE: DNA
<213> ORGANISM: Artificial Sequence
<220> FEATURE:
<223> OTHER INFORMATION: Synthetic

<400> SEQUENCE: 37
ttccaagagg atgcctcggt ctaaccagac acaaacccgt atgggtcggt        50

<210> SEQ ID NO 38
<211> LENGTH: 50
<212> TYPE: DNA
<213> ORGANISM: Artificial Sequence
<220> FEATURE:
<223> OTHER INFORMATION: Synthetic

<400> SEQUENCE: 38
aagtgttttc cggaagatgg acgcaaacac ccggtacaca gaccgcgagt        50

<210> SEQ ID NO 39
<211> LENGTH: 50
<212> TYPE: DNA
<213> ORGANISM: Artificial Sequence
<220> FEATURE:
<223> OTHER INFORMATION: Synthetic

<400> SEQUENCE: 39
taacagaagg atggtagggc ggctcagcgc actcaacttg agggcaaagt        50

<210> SEQ ID NO 40
<211> LENGTH: 50
<212> TYPE: DNA
<213> ORGANISM: Artificial Sequence
<220> FEATURE:
<223> OTHER INFORMATION: Synthetic

<400> SEQUENCE: 40
acagtacaag tcttgcgact agaccgtccg gcccaaaacc tgaaatccaa        50

<210> SEQ ID NO 41
<211> LENGTH: 50
<212> TYPE: DNA
<213> ORGANISM: Artificial Sequence
<220> FEATURE:
<223> OTHER INFORMATION: Synthetic

<400> SEQUENCE: 41
aaacaagcca gtaccgaaag cattcggacc gacttctgtc cgccgagatc        50

<210> SEQ ID NO 42
<211> LENGTH: 50
<212> TYPE: DNA
<213> ORGANISM: Artificial Sequence
<220> FEATURE:
<223> OTHER INFORMATION: Synthetic

<400> SEQUENCE: 42
gcaagcggat gactgtcaga atccccgtct aatgactgaa gacctgaaca           50

<210> SEQ ID NO 43
<211> LENGTH: 50
<212> TYPE: DNA
<213> ORGANISM: Artificial Sequence
<220> FEATURE:
<223> OTHER INFORMATION: Synthetic

<400> SEQUENCE: 43
acctaatgcc acacagattc cacccaagga tggacgagct gcccaagtac           50

<210> SEQ ID NO 44
<211> LENGTH: 50
<212> TYPE: DNA
<213> ORGANISM: Artificial Sequence
<220> FEATURE:
<223> OTHER INFORMATION: Synthetic

<400> SEQUENCE: 44
ttcagaaaag aagtgtcgtc ccgatcgcac taccgtaagg cggcaagcgt           50

<210> SEQ ID NO 45
<211> LENGTH: 50
<212> TYPE: DNA
<213> ORGANISM: Artificial Sequence
<220> FEATURE:
<223> OTHER INFORMATION: Synthetic

<400> SEQUENCE: 45
aatgccgctg gtcacacgga agaaagaagc cgaccaaaca gtgcgacttg           50

<210> SEQ ID NO 46
<211> LENGTH: 50
<212> TYPE: DNA
<213> ORGANISM: Artificial Sequence
<220> FEATURE:
<223> OTHER INFORMATION: Synthetic

<400> SEQUENCE: 46
gtgacagccg aagccgcctt tcaatttcga accatgcggt tcaaaatgtt           50

<210> SEQ ID NO 47
<211> LENGTH: 50
<212> TYPE: DNA
<213> ORGANISM: Artificial Sequence
<220> FEATURE:
<223> OTHER INFORMATION: Synthetic

<400> SEQUENCE: 47
ccaacgcggg ccgatcattt gccgataaat ctttccccg aagggcacat            50

<210> SEQ ID NO 48
<211> LENGTH: 50
<212> TYPE: DNA
<213> ORGANISM: Artificial Sequence
<220> FEATURE:
<223> OTHER INFORMATION: Synthetic

```
<400> SEQUENCE: 48
aggcccgaag gtcccccgct ttcatcctca gatcgtatgc ggtattaatc        50

<210> SEQ ID NO 49
<211> LENGTH: 50
<212> TYPE: DNA
<213> ORGANISM: Artificial Sequence
<220> FEATURE:
<223> OTHER INFORMATION: Synthetic

<400> SEQUENCE: 49
tcctacaccg aaaactttc cctactcaac ttgtgttaag caggagtata         50

<210> SEQ ID NO 50
<211> LENGTH: 50
<212> TYPE: DNA
<213> ORGANISM: Artificial Sequence
<220> FEATURE:
<223> OTHER INFORMATION: Synthetic

<400> SEQUENCE: 50
ggtccgaaga tcccttctt taatatgttt tagatgccta aacataccac         50

<210> SEQ ID NO 51
<211> LENGTH: 50
<212> TYPE: DNA
<213> ORGANISM: Artificial Sequence
<220> FEATURE:
<223> OTHER INFORMATION: Synthetic

<400> SEQUENCE: 51
cgccgcgggt ccatctcaaa gcaataaatc tttgataaga aaatcatgcg        50

<210> SEQ ID NO 52
<211> LENGTH: 50
<212> TYPE: DNA
<213> ORGANISM: Artificial Sequence
<220> FEATURE:
<223> OTHER INFORMATION: Synthetic

<400> SEQUENCE: 52
tcatcttata gcacgaggtc cgaagatccc ccgctttgct ccaaagagat        50

<210> SEQ ID NO 53
<211> LENGTH: 50
<212> TYPE: DNA
<213> ORGANISM: Artificial Sequence
<220> FEATURE:
<223> OTHER INFORMATION: Synthetic

<400> SEQUENCE: 53
acatccgatg gcaagaggcc cgaaggtccc cctctttggt cttgcgacgt        50

<210> SEQ ID NO 54
<211> LENGTH: 50
<212> TYPE: DNA
<213> ORGANISM: Artificial Sequence
<220> FEATURE:
<223> OTHER INFORMATION: Synthetic

<400> SEQUENCE: 54
caattctggg aagcgtggca ttaatactga attgtcatca tcatgcatcg        50

<210> SEQ ID NO 55
```

-continued

```
<211> LENGTH: 50
<212> TYPE: DNA
<213> ORGANISM: Artificial Sequence
<220> FEATURE:
<223> OTHER INFORMATION: Synthetic

<400> SEQUENCE: 55
ggttgatgaa aaagcatttg gagccgcgaa atttaccagt gtcttaaaac         50

<210> SEQ ID NO 56
<211> LENGTH: 50
<212> TYPE: DNA
<213> ORGANISM: Artificial Sequence
<220> FEATURE:
<223> OTHER INFORMATION: Synthetic

<400> SEQUENCE: 56
tgtccgattc agcacgggta aatagtcgta ttgttagtgg ccgaatttaa         50

<210> SEQ ID NO 57
<211> LENGTH: 50
<212> TYPE: DNA
<213> ORGANISM: Artificial Sequence
<220> FEATURE:
<223> OTHER INFORMATION: Synthetic

<400> SEQUENCE: 57
ttgctggaga gtccttctcg ggtatcgatt gtcgaagata aacatattta         50

<210> SEQ ID NO 58
<211> LENGTH: 50
<212> TYPE: DNA
<213> ORGANISM: Artificial Sequence
<220> FEATURE:
<223> OTHER INFORMATION: Synthetic

<400> SEQUENCE: 58
gtggtggatt acgccatgac atgggaggat taacgggggg gagtaatagc         50

<210> SEQ ID NO 59
<211> LENGTH: 50
<212> TYPE: DNA
<213> ORGANISM: Artificial Sequence
<220> FEATURE:
<223> OTHER INFORMATION: Synthetic

<400> SEQUENCE: 59
tctggagtat caagcactta taacctaata acacaaaacc ctcttcctgg         50

<210> SEQ ID NO 60
<211> LENGTH: 50
<212> TYPE: DNA
<213> ORGANISM: Artificial Sequence
<220> FEATURE:
<223> OTHER INFORMATION: Synthetic

<400> SEQUENCE: 60
gccctgacgt atggcgggta cgaaatgaag ccagtgacgg tgaccattac         50

<210> SEQ ID NO 61
<211> LENGTH: 50
<212> TYPE: DNA
<213> ORGANISM: Artificial Sequence
<220> FEATURE:
<223> OTHER INFORMATION: Synthetic

<400> SEQUENCE: 61
```

```
actggcggga acacatgaaa acgtaaccac gctaccagta gccagaagaa        50

<210> SEQ ID NO 62
<211> LENGTH: 50
<212> TYPE: DNA
<213> ORGANISM: Artificial Sequence
<220> FEATURE:
<223> OTHER INFORMATION: Synthetic

<400> SEQUENCE: 62
ccattaaaac taatgcctgt cataatggag ggggattcag cgaagttatt        50

<210> SEQ ID NO 63
<211> LENGTH: 50
<212> TYPE: DNA
<213> ORGANISM: Artificial Sequence
<220> FEATURE:
<223> OTHER INFORMATION: Synthetic

<400> SEQUENCE: 63
aagacatctt caccgttcac gatatttga aagcacgagg ggaaatctga         50

<210> SEQ ID NO 64
<211> LENGTH: 50
<212> TYPE: DNA
<213> ORGANISM: Artificial Sequence
<220> FEATURE:
<223> OTHER INFORMATION: Synthetic

<400> SEQUENCE: 64
caccgtcgct ttaaaacgcg cccggtggga gaatcgtcgt tgtacattta        50

<210> SEQ ID NO 65
<211> LENGTH: 50
<212> TYPE: DNA
<213> ORGANISM: Artificial Sequence
<220> FEATURE:
<223> OTHER INFORMATION: Synthetic

<400> SEQUENCE: 65
tttctgatcg cgttgctgcg ctgatcaaag aagtaaacaa agcagcttaa        50

<210> SEQ ID NO 66
<211> LENGTH: 50
<212> TYPE: DNA
<213> ORGANISM: Artificial Sequence
<220> FEATURE:
<223> OTHER INFORMATION: Synthetic

<400> SEQUENCE: 66
atggcatccg tggtatcccg actctgctgc tgttcaaaaa cggtgaagtg        50

<210> SEQ ID NO 67
<211> LENGTH: 50
<212> TYPE: DNA
<213> ORGANISM: Artificial Sequence
<220> FEATURE:
<223> OTHER INFORMATION: Synthetic

<400> SEQUENCE: 67
aggctcatcc atctgcgaca cgccgaaagc cacctttaat ccacagatat        50

<210> SEQ ID NO 68
<211> LENGTH: 50
<212> TYPE: DNA
```

<213> ORGANISM: Artificial Sequence
<220> FEATURE:
<223> OTHER INFORMATION: Synthetic

<400> SEQUENCE: 68
aatccttaaa agtcggtcgt agtccggatt ggagtctgca actcgactcc        50

<210> SEQ ID NO 69
<211> LENGTH: 50
<212> TYPE: DNA
<213> ORGANISM: Artificial Sequence
<220> FEATURE:
<223> OTHER INFORMATION: Synthetic

<400> SEQUENCE: 69
atctccgagc aataaatctt tacccgaaaa atcttatgat ctctcgggac        50

<210> SEQ ID NO 70
<211> LENGTH: 50
<212> TYPE: DNA
<213> ORGANISM: Artificial Sequence
<220> FEATURE:
<223> OTHER INFORMATION: Synthetic

<400> SEQUENCE: 70
tcatctgata gcgtgaggtc cgaagatccc ccactttctc cctcaggacg        50

<210> SEQ ID NO 71
<211> LENGTH: 50
<212> TYPE: DNA
<213> ORGANISM: Artificial Sequence
<220> FEATURE:
<223> OTHER INFORMATION: Synthetic

<400> SEQUENCE: 71
atctgacgcg ggcccatcca tcagcgataa atctttcctc cgtagagaat        50

<210> SEQ ID NO 72
<211> LENGTH: 50
<212> TYPE: DNA
<213> ORGANISM: Artificial Sequence
<220> FEATURE:
<223> OTHER INFORMATION: Synthetic

<400> SEQUENCE: 72
cttggtgagc cgttacctca ccaacaagct aatcccatct gggcacatct        50

<210> SEQ ID NO 73
<211> LENGTH: 50
<212> TYPE: DNA
<213> ORGANISM: Artificial Sequence
<220> FEATURE:
<223> OTHER INFORMATION: Synthetic

<400> SEQUENCE: 73
atcccacctg ggcatatccg gtagcgcaag gcccgaaggt cccctgcttt        50

<210> SEQ ID NO 74
<211> LENGTH: 50
<212> TYPE: DNA
<213> ORGANISM: Artificial Sequence
<220> FEATURE:
<223> OTHER INFORMATION: Synthetic

<400> SEQUENCE: 74
tctgggttca tccgatggcg tgaggcccta aggtcccccca ctttgctctt        50

<210> SEQ ID NO 75
<211> LENGTH: 50
<212> TYPE: DNA
<213> ORGANISM: Artificial Sequence
<220> FEATURE:
<223> OTHER INFORMATION: Synthetic

<400> SEQUENCE: 75
tcaagaccca cggctattaa ccgtaagctt ttcctccctg ctgaaagtgc          50

<210> SEQ ID NO 76
<211> LENGTH: 50
<212> TYPE: DNA
<213> ORGANISM: Artificial Sequence
<220> FEATURE:
<223> OTHER INFORMATION: Synthetic

<400> SEQUENCE: 76
gccggtgctt attcatatgc taccgtcatt ttcttgacat ataaaaggag          50

<210> SEQ ID NO 77
<211> LENGTH: 50
<212> TYPE: DNA
<213> ORGANISM: Artificial Sequence
<220> FEATURE:
<223> OTHER INFORMATION: Synthetic

<400> SEQUENCE: 77
gtaccgtcag accatggctg attagcacca tggcggttct tccctcctga          50

<210> SEQ ID NO 78
<211> LENGTH: 50
<212> TYPE: DNA
<213> ORGANISM: Artificial Sequence
<220> FEATURE:
<223> OTHER INFORMATION: Synthetic

<400> SEQUENCE: 78
caaggtaccg ccctatttga acggtacttg ttcttcccta gcaacagagc          50

<210> SEQ ID NO 79
<211> LENGTH: 50
<212> TYPE: DNA
<213> ORGANISM: Artificial Sequence
<220> FEATURE:
<223> OTHER INFORMATION: Synthetic

<400> SEQUENCE: 79
tattcataag gtacatacaa aacaccacac gtggcgaact ttattccctt          50

<210> SEQ ID NO 80
<211> LENGTH: 50
<212> TYPE: DNA
<213> ORGANISM: Artificial Sequence
<220> FEATURE:
<223> OTHER INFORMATION: Synthetic

<400> SEQUENCE: 80
tattcataaa gtacatgcaa acgggtatgc atacccgact ttattccttt          50

<210> SEQ ID NO 81
<211> LENGTH: 50
<212> TYPE: DNA
<213> ORGANISM: Artificial Sequence
<220> FEATURE:

<223> OTHER INFORMATION: Synthetic

<400> SEQUENCE: 81
tattcatacg gtacatacaa aaaggcacac gtgcctcact ttattcccgt        50

<210> SEQ ID NO 82
<211> LENGTH: 50
<212> TYPE: DNA
<213> ORGANISM: Artificial Sequence
<220> FEATURE:
<223> OTHER INFORMATION: Synthetic

<400> SEQUENCE: 82
aggcccgaag gtcccccgct ttcatccgta gatcgtatgc ggtattaatc        50

<210> SEQ ID NO 83
<211> LENGTH: 50
<212> TYPE: DNA
<213> ORGANISM: Artificial Sequence
<220> FEATURE:
<223> OTHER INFORMATION: Synthetic

<400> SEQUENCE: 83
cggtaccgtc atcccccgac tgtattagag ccaaggattt ctttccggac        50

<210> SEQ ID NO 84
<211> LENGTH: 50
<212> TYPE: DNA
<213> ORGANISM: Artificial Sequence
<220> FEATURE:
<223> OTHER INFORMATION: Synthetic

<400> SEQUENCE: 84
agccgcaagc ttctctttag gcggaaatcc atttcactcg aaagcatatg        50

<210> SEQ ID NO 85
<211> LENGTH: 50
<212> TYPE: DNA
<213> ORGANISM: Artificial Sequence
<220> FEATURE:
<223> OTHER INFORMATION: Synthetic

<400> SEQUENCE: 85
agacgcgagc tcatcctcag gcgaaattca tttcacctct cggcatatgg        50

<210> SEQ ID NO 86
<211> LENGTH: 50
<212> TYPE: DNA
<213> ORGANISM: Artificial Sequence
<220> FEATURE:
<223> OTHER INFORMATION: Synthetic

<400> SEQUENCE: 86
ccatcgcagt aatggagtta agctccacgc tttgacgaca gacttaaaag        50

<210> SEQ ID NO 87
<211> LENGTH: 50
<212> TYPE: DNA
<213> ORGANISM: Artificial Sequence
<220> FEATURE:
<223> OTHER INFORMATION: Synthetic

<400> SEQUENCE: 87
ccatcgctga aatggagttg agctccacgc tttaacgaca gacttgtaaa        50

<210> SEQ ID NO 88
<211> LENGTH: 50
<212> TYPE: DNA
<213> ORGANISM: Artificial Sequence
<220> FEATURE:
<223> OTHER INFORMATION: Synthetic

<400> SEQUENCE: 88
cgctctagta gcacaaggcc cgaaggtccc ctgctttcat ccatagatct          50

<210> SEQ ID NO 89
<211> LENGTH: 50
<212> TYPE: DNA
<213> ORGANISM: Artificial Sequence
<220> FEATURE:
<223> OTHER INFORMATION: Synthetic

<400> SEQUENCE: 89
tcagtgacgc aaaagcgcct ttcaactttc ttccatgcgg aaaatagtgt          50

<210> SEQ ID NO 90
<211> LENGTH: 50
<212> TYPE: DNA
<213> ORGANISM: Artificial Sequence
<220> FEATURE:
<223> OTHER INFORMATION: Synthetic

<400> SEQUENCE: 90
tcctgaagcg ataaatcttt agacacaagt cgatgccgac tcgtgaccac          50

<210> SEQ ID NO 91
<211> LENGTH: 50
<212> TYPE: DNA
<213> ORGANISM: Artificial Sequence
<220> FEATURE:
<223> OTHER INFORMATION: Synthetic

<400> SEQUENCE: 91
aggtcatctt caaccgaaaa actttccagc cccgatcatg cgatcagagc          50

<210> SEQ ID NO 92
<211> LENGTH: 50
<212> TYPE: DNA
<213> ORGANISM: Artificial Sequence
<220> FEATURE:
<223> OTHER INFORMATION: Synthetic

<400> SEQUENCE: 92
tcatcttcaa ccgaaaaact ttccaaaccc gcggatgccc gcaggtttca          50

<210> SEQ ID NO 93
<211> LENGTH: 50
<212> TYPE: DNA
<213> ORGANISM: Artificial Sequence
<220> FEATURE:
<223> OTHER INFORMATION: Synthetic

<400> SEQUENCE: 93
cagacgcgag ctcttcctaa ggtggataaa tccttttacc tctcggcgta          50

<210> SEQ ID NO 94
<211> LENGTH: 50
<212> TYPE: DNA
<213> ORGANISM: Artificial Sequence
<220> FEATURE:
<223> OTHER INFORMATION: Synthetic

<400> SEQUENCE: 94
ggccgctcca ggagcacgag gtcttgcgat cccccgcttt catccttaga      50

<210> SEQ ID NO 95
<211> LENGTH: 50
<212> TYPE: DNA
<213> ORGANISM: Artificial Sequence
<220> FEATURE:
<223> OTHER INFORMATION: Synthetic

<400> SEQUENCE: 95
atctttcatc aaaattttt cccggctcgg cgatgccgcc aagacggagt      50

<210> SEQ ID NO 96
<211> LENGTH: 50
<212> TYPE: DNA
<213> ORGANISM: Artificial Sequence
<220> FEATURE:
<223> OTHER INFORMATION: Synthetic

<400> SEQUENCE: 96
tcatgtaagc cgctcctccg gcggaatcac acctttgctc cgcagagttc      50

<210> SEQ ID NO 97
<211> LENGTH: 50
<212> TYPE: DNA
<213> ORGANISM: Artificial Sequence
<220> FEATURE:
<223> OTHER INFORMATION: Synthetic

<400> SEQUENCE: 97
tattcttaaa gcgccaggcc ttgcggtccc cagcttttct cctcagagat      50

<210> SEQ ID NO 98
<211> LENGTH: 50
<212> TYPE: DNA
<213> ORGANISM: Artificial Sequence
<220> FEATURE:
<223> OTHER INFORMATION: Synthetic

<400> SEQUENCE: 98
ctccatcagc gcccttgcga gctttcatcc cttctgcgac gaagggatcg      50

<210> SEQ ID NO 99
<211> LENGTH: 50
<212> TYPE: DNA
<213> ORGANISM: Artificial Sequence
<220> FEATURE:
<223> OTHER INFORMATION: Synthetic

<400> SEQUENCE: 99
ggggcacggg ctcatcttgg ggcggaatca cacctttggt ccgcaaacat      50

<210> SEQ ID NO 100
<211> LENGTH: 50
<212> TYPE: DNA
<213> ORGANISM: Artificial Sequence
<220> FEATURE:
<223> OTHER INFORMATION: Synthetic

<400> SEQUENCE: 100
tccttgacca aaattctttc cacgcccgtg ggatgcccca aggcgtcgta      50

<210> SEQ ID NO 101
<211> LENGTH: 50

<210> SEQ ID NO 101
<211> LENGTH: 50
<212> TYPE: DNA
<213> ORGANISM: Artificial Sequence
<220> FEATURE:
<223> OTHER INFORMATION: Synthetic

<400> SEQUENCE: 101
tgatatcggc cgctccaatc gcgcgaggtc ttgcgatccc ccgctttcat         50

<210> SEQ ID NO 102
<211> LENGTH: 50
<212> TYPE: DNA
<213> ORGANISM: Artificial Sequence
<220> FEATURE:
<223> OTHER INFORMATION: Synthetic

<400> SEQUENCE: 102
gctcttgcga gctccctttc ccgaaaaact ccttacgagt tccgtcgctc         50

<210> SEQ ID NO 103
<211> LENGTH: 50
<212> TYPE: DNA
<213> ORGANISM: Artificial Sequence
<220> FEATURE:
<223> OTHER INFORMATION: Synthetic

<400> SEQUENCE: 103
agacgcgagc ttctctttag gcggattact ccatttcact cggaagcata         50

<210> SEQ ID NO 104
<211> LENGTH: 50
<212> TYPE: DNA
<213> ORGANISM: Artificial Sequence
<220> FEATURE:
<223> OTHER INFORMATION: Synthetic

<400> SEQUENCE: 104
cgctccaata gcgagaggtc ttgcgatccc ccctttcac ccgaaggtcg          50

<210> SEQ ID NO 105
<211> LENGTH: 50
<212> TYPE: DNA
<213> ORGANISM: Artificial Sequence
<220> FEATURE:
<223> OTHER INFORMATION: Synthetic

<400> SEQUENCE: 105
cggtcccagc ctttccagta atctctctct agactactgc ttacgacgta         50

<210> SEQ ID NO 106
<211> LENGTH: 50
<212> TYPE: DNA
<213> ORGANISM: Artificial Sequence
<220> FEATURE:
<223> OTHER INFORMATION: Synthetic

<400> SEQUENCE: 106
taatcctaaa gcgccaggcc ttgcggtccc cagctttcct cctaagagat         50

<210> SEQ ID NO 107
<211> LENGTH: 50
<212> TYPE: DNA
<213> ORGANISM: Artificial Sequence
<220> FEATURE:
<223> OTHER INFORMATION: Synthetic

<400> SEQUENCE: 107

```
gtcccccgct tcatccata gatcgtatgc ggtattagcg taactttcgc        50
```

<210> SEQ ID NO 108
<211> LENGTH: 50
<212> TYPE: DNA
<213> ORGANISM: Artificial Sequence
<220> FEATURE:
<223> OTHER INFORMATION: Synthetic

<400> SEQUENCE: 108

```
caatattcgg tattagcacc ggtttcccgg tgttatccca aagtggaggg        50
```

<210> SEQ ID NO 109
<211> LENGTH: 50
<212> TYPE: DNA
<213> ORGANISM: Artificial Sequence
<220> FEATURE:
<223> OTHER INFORMATION: Synthetic

<400> SEQUENCE: 109

```
aggtcttgcg atcccccct tcacccgta ggtcgtatgc ggtattaatc         50
```

<210> SEQ ID NO 110
<211> LENGTH: 50
<212> TYPE: DNA
<213> ORGANISM: Artificial Sequence
<220> FEATURE:
<223> OTHER INFORMATION: Synthetic

<400> SEQUENCE: 110

```
cagcttttct cctcagagat tacgcggtat tagcctgagt ttccccaggt       50
```

<210> SEQ ID NO 111
<211> LENGTH: 50
<212> TYPE: DNA
<213> ORGANISM: Artificial Sequence
<220> FEATURE:
<223> OTHER INFORMATION: Synthetic

<400> SEQUENCE: 111

```
ctttcccct cagggcgtat gcggtattag cgcaactttc gctgcgttat        50
```

<210> SEQ ID NO 112
<211> LENGTH: 50
<212> TYPE: DNA
<213> ORGANISM: Artificial Sequence
<220> FEATURE:
<223> OTHER INFORMATION: Synthetic

<400> SEQUENCE: 112

```
cagacgcgag ctcttcctaa ggtggataga tccttttacc tctcggcata      50
```

<210> SEQ ID NO 113
<211> LENGTH: 25
<212> TYPE: DNA
<213> ORGANISM: Artificial Sequence
<220> FEATURE:
<223> OTHER INFORMATION: Synthetic

<400> SEQUENCE: 113

```
tgacgggcgg tgtgtacaag gcccg                                  25
```

<210> SEQ ID NO 114
<211> LENGTH: 20
<212> TYPE: DNA
<213> ORGANISM: Artificial Sequence

```
<220> FEATURE:
<223> OTHER INFORMATION: Synthetic

<400> SEQUENCE: 114
atacaggcgc tcgataagag                                               20

<210> SEQ ID NO 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
agctgctagg ggagtcattc                                               20

<210> SEQ ID NO 116
<211> LENGTH: 20
<212> TYPE: DNA
<213> ORGANISM: Artificial Sequence
<220> FEATURE:
<223> OTHER INFORMATION: Synthetic

<400> SEQUENCE: 116
aactcgactt tatggaaggg                                               20

<210> SEQ ID NO 117
<211> LENGTH: 20
<212> TYPE: DNA
<213> ORGANISM: Artificial Sequence
<220> FEATURE:
<223> OTHER INFORMATION: Synthetic

<400> SEQUENCE: 117
caaagtccct ctaagaagac                                               20

<210> SEQ ID NO 118
<211> LENGTH: 20
<212> TYPE: DNA
<213> ORGANISM: Artificial Sequence
<220> FEATURE:
<223> OTHER INFORMATION: Synthetic

<400> SEQUENCE: 118
ttggctttag ccggcgatag                                               20

<210> SEQ ID NO 119
<211> LENGTH: 20
<212> TYPE: DNA
<213> ORGANISM: Artificial Sequence
<220> FEATURE:
<223> OTHER INFORMATION: Synthetic

<400> SEQUENCE: 119
aagccaaggt aggcgtttcc                                               20

<210> SEQ ID NO 120
<211> LENGTH: 20
<212> TYPE: DNA
<213> ORGANISM: Artificial Sequence
<220> FEATURE:
<223> OTHER INFORMATION: Synthetic

<400> SEQUENCE: 120
gacgacacat aactctagag                                               20
```

```
<210> SEQ ID NO 121
<211> LENGTH: 20
<212> TYPE: DNA
<213> ORGANISM: Artificial Sequence
<220> FEATURE:
<223> OTHER INFORMATION: Synthetic

<400> SEQUENCE: 121
tcatccaatc cttggttgac                                                     20

<210> SEQ ID NO 122
<211> LENGTH: 18
<212> TYPE: DNA
<213> ORGANISM: Artificial Sequence
<220> FEATURE:
<223> OTHER INFORMATION: Synthetic

<400> SEQUENCE: 122
aacttgccca atgcgcgg                                                       18

<210> SEQ ID NO 123
<211> LENGTH: 19
<212> TYPE: DNA
<213> ORGANISM: Artificial Sequence
<220> FEATURE:
<223> OTHER INFORMATION: Synthetic

<400> SEQUENCE: 123
gggaatacgg tggtgtctg                                                      19

<210> SEQ ID NO 124
<211> LENGTH: 20
<212> TYPE: DNA
<213> ORGANISM: Artificial Sequence
<220> FEATURE:
<223> OTHER INFORMATION: Synthetic

<400> SEQUENCE: 124
gattggaatg atgggaatcc                                                     20

<210> SEQ ID NO 125
<211> LENGTH: 20
<212> TYPE: DNA
<213> ORGANISM: Artificial Sequence
<220> FEATURE:
<223> OTHER INFORMATION: Synthetic

<400> SEQUENCE: 125
aggagaagtc aagtatgacg                                                     20

<210> SEQ ID NO 126
<211> LENGTH: 19
<212> TYPE: DNA
<213> ORGANISM: Artificial Sequence
<220> FEATURE:
<223> OTHER INFORMATION: Synthetic

<400> SEQUENCE: 126
gcggtagtaa ggagacgtg                                                      19

<210> SEQ ID NO 127
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 127
gcatcggcat cgtttactgc                                              20

<210> SEQ ID NO 128
<211> LENGTH: 20
<212> TYPE: DNA
<213> ORGANISM: Artificial Sequence
<220> FEATURE:
<223> OTHER INFORMATION: Synthetic

<400> SEQUENCE: 128
ttcggtggtg aggtattatc                                              20

<210> SEQ ID NO 129
<211> LENGTH: 20
<212> TYPE: DNA
<213> ORGANISM: Artificial Sequence
<220> FEATURE:
<223> OTHER INFORMATION: Synthetic

<400> SEQUENCE: 129
aagatcgctg ggatagtgtc                                              20

<210> SEQ ID NO 130
<211> LENGTH: 20
<212> TYPE: DNA
<213> ORGANISM: Artificial Sequence
<220> FEATURE:
<223> OTHER INFORMATION: Synthetic

<400> SEQUENCE: 130
atcgagtatc aattggaggg                                              20

<210> SEQ ID NO 131
<211> LENGTH: 20
<212> TYPE: DNA
<213> ORGANISM: Artificial Sequence
<220> FEATURE:
<223> OTHER INFORMATION: Synthetic

<400> SEQUENCE: 131
gacggggtca atacaacgac                                              20

<210> SEQ ID NO 132
<211> LENGTH: 20
<212> TYPE: DNA
<213> ORGANISM: Artificial Sequence
<220> FEATURE:
<223> OTHER INFORMATION: Synthetic

<400> SEQUENCE: 132
gccaatggtc ttcttattgg                                              20

<210> SEQ ID NO 133
<211> LENGTH: 20
<212> TYPE: DNA
<213> ORGANISM: Artificial Sequence
<220> FEATURE:
<223> OTHER INFORMATION: Synthetic

<400> SEQUENCE: 133
gaggtcgtaa attgacactc                                              20

<210> SEQ ID NO 134
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 134
ttcaaaccgg cctcgttctg                                               20

<210> SEQ ID NO 135
<211> LENGTH: 20
<212> TYPE: DNA
<213> ORGANISM: Artificial Sequence
<220> FEATURE:
<223> OTHER INFORMATION: Synthetic

<400> SEQUENCE: 135
cccataacca acgaaatagc                                               20

<210> SEQ ID NO 136
<211> LENGTH: 20
<212> TYPE: DNA
<213> ORGANISM: Artificial Sequence
<220> FEATURE:
<223> OTHER INFORMATION: Synthetic

<400> SEQUENCE: 136
ttagcgaatc gtggcacgtc                                               20

<210> SEQ ID NO 137
<211> LENGTH: 20
<212> TYPE: DNA
<213> ORGANISM: Artificial Sequence
<220> FEATURE:
<223> OTHER INFORMATION: Synthetic

<400> SEQUENCE: 137
aatgtattcc tgcaaacgcc                                               20

<210> SEQ ID NO 138
<211> LENGTH: 20
<212> TYPE: DNA
<213> ORGANISM: Artificial Sequence
<220> FEATURE:
<223> OTHER INFORMATION: Synthetic

<400> SEQUENCE: 138
gggttcttac gaactttggg                                               20

<210> SEQ ID NO 139
<211> LENGTH: 20
<212> TYPE: DNA
<213> ORGANISM: Artificial Sequence
<220> FEATURE:
<223> OTHER INFORMATION: Synthetic

<400> SEQUENCE: 139
ctgatcgggc ttgaaagacc                                               20

<210> SEQ ID NO 140
<211> LENGTH: 20
<212> TYPE: DNA
<213> ORGANISM: Artificial Sequence
<220> FEATURE:
<223> OTHER INFORMATION: Synthetic

<400> SEQUENCE: 140
```

```
tatcgaggac caattggagg                                              20

<210> SEQ ID NO 141
<211> LENGTH: 20
<212> TYPE: DNA
<213> ORGANISM: Artificial Sequence
<220> FEATURE:
<223> OTHER INFORMATION: Synthetic

<400> SEQUENCE: 141
gacggagtca atacaacgac                                              20

<210> SEQ ID NO 142
<211> LENGTH: 20
<212> TYPE: DNA
<213> ORGANISM: Artificial Sequence
<220> FEATURE:
<223> OTHER INFORMATION: Synthetic

<400> SEQUENCE: 142
tggactcttt tgagtccggc                                              20

<210> SEQ ID NO 143
<211> LENGTH: 20
<212> TYPE: DNA
<213> ORGANISM: Artificial Sequence
<220> FEATURE:
<223> OTHER INFORMATION: Synthetic

<400> SEQUENCE: 143
atcaatacta acacccaccg                                              20

<210> SEQ ID NO 144
<211> LENGTH: 20
<212> TYPE: DNA
<213> ORGANISM: Artificial Sequence
<220> FEATURE:
<223> OTHER INFORMATION: Synthetic

<400> SEQUENCE: 144
taacgatagc gggctcgttc                                              20

<210> SEQ ID NO 145
<211> LENGTH: 20
<212> TYPE: DNA
<213> ORGANISM: Artificial Sequence
<220> FEATURE:
<223> OTHER INFORMATION: Synthetic

<400> SEQUENCE: 145
catagggtgc tgatagagtc                                              20

<210> SEQ ID NO 146
<211> LENGTH: 20
<212> TYPE: DNA
<213> ORGANISM: Artificial Sequence
<220> FEATURE:
<223> OTHER INFORMATION: Synthetic

<400> SEQUENCE: 146
ccgagatttc tcggaaattg                                              20

<210> SEQ ID NO 147
<211> LENGTH: 20
<212> TYPE: DNA
```

<213> ORGANISM: Artificial Sequence
<220> FEATURE:
<223> OTHER INFORMATION: Synthetic

<400> SEQUENCE: 147
tttctcacga gctgctgagg                                               20

<210> SEQ ID NO 148
<211> LENGTH: 20
<212> TYPE: DNA
<213> ORGANISM: Artificial Sequence
<220> FEATURE:
<223> OTHER INFORMATION: Synthetic

<400> SEQUENCE: 148
atggtggagg tgattcattc                                               20

<210> SEQ ID NO 149
<211> LENGTH: 20
<212> TYPE: DNA
<213> ORGANISM: Artificial Sequence
<220> FEATURE:
<223> OTHER INFORMATION: Synthetic

<400> SEQUENCE: 149
aattgacatc cactgatccc                                               20

<210> SEQ ID NO 150
<211> LENGTH: 20
<212> TYPE: DNA
<213> ORGANISM: Artificial Sequence
<220> FEATURE:
<223> OTHER INFORMATION: Synthetic

<400> SEQUENCE: 150
gatacaggac tcatccgagg                                               20

<210> SEQ ID NO 151
<211> LENGTH: 20
<212> TYPE: DNA
<213> ORGANISM: Artificial Sequence
<220> FEATURE:
<223> OTHER INFORMATION: Synthetic

<400> SEQUENCE: 151
aaacgcctgc agatcgctag                                               20

<210> SEQ ID NO 152
<211> LENGTH: 20
<212> TYPE: DNA
<213> ORGANISM: Artificial Sequence
<220> FEATURE:
<223> OTHER INFORMATION: Synthetic

<400> SEQUENCE: 152
acaatgccgg gcctttcaag                                               20

<210> SEQ ID NO 153
<211> LENGTH: 20
<212> TYPE: DNA
<213> ORGANISM: Artificial Sequence
<220> FEATURE:
<223> OTHER INFORMATION: Synthetic

<400> SEQUENCE: 153
tggagtcgtt acaaacttcc                                               20

<210> SEQ ID NO 154
<211> LENGTH: 20
<212> TYPE: DNA
<213> ORGANISM: Artificial Sequence
<220> FEATURE:
<223> OTHER INFORMATION: Synthetic

<400> SEQUENCE: 154
tcggcgacga tgattcattc                                                  20

<210> SEQ ID NO 155
<211> LENGTH: 20
<212> TYPE: DNA
<213> ORGANISM: Artificial Sequence
<220> FEATURE:
<223> OTHER INFORMATION: Synthetic

<400> SEQUENCE: 155
tgaacaaacc acgcccaatc                                                  20

<210> SEQ ID NO 156
<211> LENGTH: 20
<212> TYPE: DNA
<213> ORGANISM: Artificial Sequence
<220> FEATURE:
<223> OTHER INFORMATION: Synthetic

<400> SEQUENCE: 156
cggtttaccg gcgatagatc                                                  20

<210> SEQ ID NO 157
<211> LENGTH: 20
<212> TYPE: DNA
<213> ORGANISM: Artificial Sequence
<220> FEATURE:
<223> OTHER INFORMATION: Synthetic

<400> SEQUENCE: 157
ttctctcgag gtgctgaagg                                                  20

<210> SEQ ID NO 158
<211> LENGTH: 20
<212> TYPE: DNA
<213> ORGANISM: Artificial Sequence
<220> FEATURE:
<223> OTHER INFORMATION: Synthetic

<400> SEQUENCE: 158
aatcggatcg catgggctag                                                  20

<210> SEQ ID NO 159
<211> LENGTH: 20
<212> TYPE: DNA
<213> ORGANISM: Artificial Sequence
<220> FEATURE:
<223> OTHER INFORMATION: Synthetic

<400> SEQUENCE: 159
gaacgggata attctcgccc                                                  20

<210> SEQ ID NO 160
<211> LENGTH: 20
<212> TYPE: DNA
<213> ORGANISM: Artificial Sequence
<220> FEATURE:

```
<223> OTHER INFORMATION: Synthetic

<400> SEQUENCE: 160
cccacttatg tgggtttgac                                               20

<210> SEQ ID NO 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
gaagtagagg atcttgcctc                                               20

<210> SEQ ID NO 162
<211> LENGTH: 20
<212> TYPE: DNA
<213> ORGANISM: Artificial Sequence
<220> FEATURE:
<223> OTHER INFORMATION: Synthetic

<400> SEQUENCE: 162
gacagcttct ttaatggagg                                               20

<210> SEQ ID NO 163
<211> LENGTH: 20
<212> TYPE: DNA
<213> ORGANISM: Artificial Sequence
<220> FEATURE:
<223> OTHER INFORMATION: Synthetic

<400> SEQUENCE: 163
atctgttggt cctccaaatc                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic

<400> SEQUENCE: 164
aatacagggc tctttgagtc                                               20

<210> SEQ ID NO 165
<211> LENGTH: 20
<212> TYPE: DNA
<213> ORGANISM: Artificial Sequence
<220> FEATURE:
<223> OTHER INFORMATION: Synthetic

<400> SEQUENCE: 165
aagacgtacc accgatcctg                                               20

<210> SEQ ID NO 166
<211> LENGTH: 20
<212> TYPE: DNA
<213> ORGANISM: Artificial Sequence
<220> FEATURE:
<223> OTHER INFORMATION: Synthetic

<400> SEQUENCE: 166
taacaatgcg gagccttcgg                                               20
```

```
<210> SEQ ID NO 167
<211> LENGTH: 20
<212> TYPE: DNA
<213> ORGANISM: Artificial Sequence
<220> FEATURE:
<223> OTHER INFORMATION: Synthetic

<400> SEQUENCE: 167
aagaacgtcc gccaatcctg                                               20

<210> SEQ ID NO 168
<211> LENGTH: 20
<212> TYPE: DNA
<213> ORGANISM: Artificial Sequence
<220> FEATURE:
<223> OTHER INFORMATION: Synthetic

<400> SEQUENCE: 168
tatctggcgc ttttgcgtcg                                               20

<210> SEQ ID NO 169
<211> LENGTH: 20
<212> TYPE: DNA
<213> ORGANISM: Artificial Sequence
<220> FEATURE:
<223> OTHER INFORMATION: Synthetic

<400> SEQUENCE: 169
caacgtctac ccatcccaag                                               20

<210> SEQ ID NO 170
<211> LENGTH: 20
<212> TYPE: DNA
<213> ORGANISM: Artificial Sequence
<220> FEATURE:
<223> OTHER INFORMATION: Synthetic

<400> SEQUENCE: 170
actcgggaac ctagttctac                                               20

<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
tctcttacgg cgccgaaaag                                               20

<210> SEQ ID NO 172
<211> LENGTH: 20
<212> TYPE: DNA
<213> ORGANISM: Artificial Sequence
<220> FEATURE:
<223> OTHER INFORMATION: Synthetic

<400> SEQUENCE: 172
agggccaacg gtcttgttat                                               20

<210> SEQ ID NO 173
<211> LENGTH: 20
<212> TYPE: DNA
<213> ORGANISM: Artificial Sequence
<220> FEATURE:
<223> OTHER INFORMATION: Synthetic
```

<400> SEQUENCE: 173
tcgcaaattg acatccactg                                                    20

<210> SEQ ID NO 174
<211> LENGTH: 20
<212> TYPE: DNA
<213> ORGANISM: Artificial Sequence
<220> FEATURE:
<223> OTHER INFORMATION: Synthetic

<400> SEQUENCE: 174
ctctctccga gtatcaattg                                                    20

<210> SEQ ID NO 175
<211> LENGTH: 20
<212> TYPE: DNA
<213> ORGANISM: Artificial Sequence
<220> FEATURE:
<223> OTHER INFORMATION: Synthetic

<400> SEQUENCE: 175
acttccctca atcgctagtc                                                    20

<210> SEQ ID NO 176
<211> LENGTH: 20
<212> TYPE: DNA
<213> ORGANISM: Artificial Sequence
<220> FEATURE:
<223> OTHER INFORMATION: Synthetic

<400> SEQUENCE: 176
gcagagcttc acagttttgc                                                    20

<210> SEQ ID NO 177
<211> LENGTH: 20
<212> TYPE: DNA
<213> ORGANISM: Artificial Sequence
<220> FEATURE:
<223> OTHER INFORMATION: Synthetic

<400> SEQUENCE: 177
agacgtctcc tgatcgcaag                                                    20

<210> SEQ ID NO 178
<211> LENGTH: 20
<212> TYPE: DNA
<213> ORGANISM: Artificial Sequence
<220> FEATURE:
<223> OTHER INFORMATION: Synthetic

<400> SEQUENCE: 178
atacgtcccg ggactgcaat                                                    20

<210> SEQ ID NO 179
<211> LENGTH: 20
<212> TYPE: DNA
<213> ORGANISM: Artificial Sequence
<220> FEATURE:
<223> OTHER INFORMATION: Synthetic

<400> SEQUENCE: 179
cgaaggcgga taattctcgc                                                    20

<210> SEQ ID NO 180
<211> LENGTH: 20

```
<212> TYPE: DNA
<213> ORGANISM: Artificial Sequence
<220> FEATURE:
<223> OTHER INFORMATION: Synthetic

<400> SEQUENCE: 180
acaatgcagg gcctttacgg                                               20

<210> SEQ ID NO 181
<211> LENGTH: 20
<212> TYPE: DNA
<213> ORGANISM: Artificial Sequence
<220> FEATURE:
<223> OTHER INFORMATION: Synthetic

<400> SEQUENCE: 181
gaataacact cactgatccc                                               20

<210> SEQ ID NO 182
<211> LENGTH: 20
<212> TYPE: DNA
<213> ORGANISM: Artificial Sequence
<220> FEATURE:
<223> OTHER INFORMATION: Synthetic

<400> SEQUENCE: 182
atacaggact catccgaggc                                               20

<210> SEQ ID NO 183
<211> LENGTH: 20
<212> TYPE: DNA
<213> ORGANISM: Artificial Sequence
<220> FEATURE:
<223> OTHER INFORMATION: Synthetic

<400> SEQUENCE: 183
aaacgcctgc agatcgctag                                               20

<210> SEQ ID NO 184
<211> LENGTH: 20
<212> TYPE: DNA
<213> ORGANISM: Artificial Sequence
<220> FEATURE:
<223> OTHER INFORMATION: Synthetic

<400> SEQUENCE: 184
ctttacaggt ctggcaattg                                               20

<210> SEQ ID NO 185
<211> LENGTH: 20
<212> TYPE: DNA
<213> ORGANISM: Artificial Sequence
<220> FEATURE:
<223> OTHER INFORMATION: Synthetic

<400> SEQUENCE: 185
catacagtgc tgacagggtc                                               20

<210> SEQ ID NO 186
<211> LENGTH: 20
<212> TYPE: DNA
<213> ORGANISM: Artificial Sequence
<220> FEATURE:
<223> OTHER INFORMATION: Synthetic

<400> SEQUENCE: 186
```

-continued cagggccttt tcaggtcttg　　　　　　　　　　　　　　　　　　　　　　　　　20

<210> SEQ ID NO 187
<211> LENGTH: 20
<212> TYPE: DNA
<213> ORGANISM: Artificial Sequence
<220> FEATURE:
<223> OTHER INFORMATION: Synthetic

<400> SEQUENCE: 187
cacaaggtgc caacagagtc　　　　　　　　　　　　　　　　　　　　　　　　　20

<210> SEQ ID NO 188
<211> LENGTH: 20
<212> TYPE: DNA
<213> ORGANISM: Artificial Sequence
<220> FEATURE:
<223> OTHER INFORMATION: Synthetic

<400> SEQUENCE: 188
aacaatgtct ggccctacgg　　　　　　　　　　　　　　　　　　　　　　　　　20

<210> SEQ ID NO 189
<211> LENGTH: 20
<212> TYPE: DNA
<213> ORGANISM: Artificial Sequence
<220> FEATURE:
<223> OTHER INFORMATION: Synthetic

<400> SEQUENCE: 189
gtaaacaacg cccaccgatc　　　　　　　　　　　　　　　　　　　　　　　　　20

<210> SEQ ID NO 190
<211> LENGTH: 20
<212> TYPE: DNA
<213> ORGANISM: Artificial Sequence
<220> FEATURE:
<223> OTHER INFORMATION: Synthetic

<400> SEQUENCE: 190
gagggcaagt ctggtgccag　　　　　　　　　　　　　　　　　　　　　　　　　20

<210> SEQ ID NO 191
<211> LENGTH: 20
<212> TYPE: DNA
<213> ORGANISM: Artificial Sequence
<220> FEATURE:
<223> OTHER INFORMATION: Synthetic

<400> SEQUENCE: 191
cgaatggatt aagagcttgc　　　　　　　　　　　　　　　　　　　　　　　　　20

<210> SEQ ID NO 192
<211> LENGTH: 20
<212> TYPE: DNA
<213> ORGANISM: Artificial Sequence
<220> FEATURE:
<223> OTHER INFORMATION: Synthetic

<400> SEQUENCE: 192
tgccagctta ttcaactagc　　　　　　　　　　　　　　　　　　　　　　　　　20

<210> SEQ ID NO 193
<211> LENGTH: 20
<212> TYPE: DNA
<213> ORGANISM: Artificial Sequence

```
<220> FEATURE:
<223> OTHER INFORMATION: Synthetic

<400> SEQUENCE: 193
gaacgtacca tttgctacgg                                              20

<210> SEQ ID NO 194
<211> LENGTH: 20
<212> TYPE: DNA
<213> ORGANISM: Artificial Sequence
<220> FEATURE:
<223> OTHER INFORMATION: Synthetic

<400> SEQUENCE: 194
accgtcatta tcttcaccgg                                              20

<210> SEQ ID NO 195
<211> LENGTH: 18
<212> TYPE: DNA
<213> ORGANISM: Artificial Sequence
<220> FEATURE:
<223> OTHER INFORMATION: Synthetic

<400> SEQUENCE: 195
acgggcttcg gcctggtg                                                18

<210> SEQ ID NO 196
<211> LENGTH: 20
<212> TYPE: DNA
<213> ORGANISM: Artificial Sequence
<220> FEATURE:
<223> OTHER INFORMATION: Synthetic

<400> SEQUENCE: 196
tccgggtatt agccagaatg                                              20

<210> SEQ ID NO 197
<211> LENGTH: 20
<212> TYPE: DNA
<213> ORGANISM: Artificial Sequence
<220> FEATURE:
<223> OTHER INFORMATION: Synthetic

<400> SEQUENCE: 197
gcttgctaga agtggattag                                              20

<210> SEQ ID NO 198
<211> LENGTH: 20
<212> TYPE: DNA
<213> ORGANISM: Artificial Sequence
<220> FEATURE:
<223> OTHER INFORMATION: Synthetic

<400> SEQUENCE: 198
cgtcagaatt cttccctaag                                              20

<210> SEQ ID NO 199
<211> LENGTH: 20
<212> TYPE: DNA
<213> ORGANISM: Artificial Sequence
<220> FEATURE:
<223> OTHER INFORMATION: Synthetic

<400> SEQUENCE: 199
tttagtggcg gaagggttag                                              20
```

```
<210> SEQ ID NO 200
<211> LENGTH: 20
<212> TYPE: DNA
<213> ORGANISM: Artificial Sequence
<220> FEATURE:
<223> OTHER INFORMATION: Synthetic

<400> SEQUENCE: 200
atctctctta ttcccaagcg                                              20

<210> SEQ ID NO 201
<211> LENGTH: 20
<212> TYPE: DNA
<213> ORGANISM: Artificial Sequence
<220> FEATURE:
<223> OTHER INFORMATION: Synthetic

<400> SEQUENCE: 201
aagcttcctt cgggaagtgg                                              20

<210> SEQ ID NO 202
<211> LENGTH: 19
<212> TYPE: DNA
<213> ORGANISM: Artificial Sequence
<220> FEATURE:
<223> OTHER INFORMATION: Synthetic

<400> SEQUENCE: 202
ggtaccgtca ttatcgtcc                                               19

<210> SEQ ID NO 203
<211> LENGTH: 20
<212> TYPE: DNA
<213> ORGANISM: Artificial Sequence
<220> FEATURE:
<223> OTHER INFORMATION: Synthetic

<400> SEQUENCE: 203
ataacctggg gaaactcggg                                              20

<210> SEQ ID NO 204
<211> LENGTH: 20
<212> TYPE: DNA
<213> ORGANISM: Artificial Sequence
<220> FEATURE:
<223> OTHER INFORMATION: Synthetic

<400> SEQUENCE: 204
ccaaggatat taccttgag                                               20

<210> SEQ ID NO 205
<211> LENGTH: 20
<212> TYPE: DNA
<213> ORGANISM: Artificial Sequence
<220> FEATURE:
<223> OTHER INFORMATION: Synthetic

<400> SEQUENCE: 205
agaagcttgc ttctttgctg                                              20

<210> SEQ ID NO 206
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 206
ttcctccccg ctgaaagtac                                                 20

<210> SEQ ID NO 207
<211> LENGTH: 18
<212> TYPE: DNA
<213> ORGANISM: Artificial Sequence
<220> FEATURE:
<223> OTHER INFORMATION: Synthetic

<400> SEQUENCE: 207
caattctggg aagcgtgg                                                   18

<210> SEQ ID NO 208
<211> LENGTH: 18
<212> TYPE: DNA
<213> ORGANISM: Artificial Sequence
<220> FEATURE:
<223> OTHER INFORMATION: Synthetic

<400> SEQUENCE: 208
cgatgcatga tgatgaca                                                   18

<210> SEQ ID NO 209
<211> LENGTH: 18
<212> TYPE: DNA
<213> ORGANISM: Artificial Sequence
<220> FEATURE:
<223> OTHER INFORMATION: Synthetic

<400> SEQUENCE: 209
gtggtggatt acgccatg                                                   18

<210> SEQ ID NO 210
<211> LENGTH: 18
<212> TYPE: DNA
<213> ORGANISM: Artificial Sequence
<220> FEATURE:
<223> OTHER INFORMATION: Synthetic

<400> SEQUENCE: 210
gctattactc cccccgt                                                    18

<210> SEQ ID NO 211
<211> LENGTH: 18
<212> TYPE: DNA
<213> ORGANISM: Artificial Sequence
<220> FEATURE:
<223> OTHER INFORMATION: Synthetic

<400> SEQUENCE: 211
tctggagtat caagcact                                                   18

<210> SEQ ID NO 212
<211> LENGTH: 18
<212> TYPE: DNA
<213> ORGANISM: Artificial Sequence
<220> FEATURE:
<223> OTHER INFORMATION: Synthetic

<400> SEQUENCE: 212
ccaggaagag ggttttgt                                                   18

<210> SEQ ID NO 213
```

```
<211> LENGTH: 18
<212> TYPE: DNA
<213> ORGANISM: Artificial Sequence
<220> FEATURE:
<223> OTHER INFORMATION: Synthetic

<400> SEQUENCE: 213
gccctgacgt atggcggg                                                18

<210> SEQ ID NO 214
<211> LENGTH: 18
<212> TYPE: DNA
<213> ORGANISM: Artificial Sequence
<220> FEATURE:
<223> OTHER INFORMATION: Synthetic

<400> SEQUENCE: 214
gtaatggtca ccgtcact                                                18

<210> SEQ ID NO 215
<211> LENGTH: 18
<212> TYPE: DNA
<213> ORGANISM: Artificial Sequence
<220> FEATURE:
<223> OTHER INFORMATION: Synthetic

<400> SEQUENCE: 215
aagacatctt caccgttc                                                18

<210> SEQ ID NO 216
<211> LENGTH: 18
<212> TYPE: DNA
<213> ORGANISM: Artificial Sequence
<220> FEATURE:
<223> OTHER INFORMATION: Synthetic

<400> SEQUENCE: 216
tcagatttcc cctcgtgc                                                18

<210> SEQ ID NO 217
<211> LENGTH: 18
<212> TYPE: DNA
<213> ORGANISM: Artificial Sequence
<220> FEATURE:
<223> OTHER INFORMATION: Synthetic

<400> SEQUENCE: 217
atggcatccg tggtatcc                                                18

<210> SEQ ID NO 218
<211> LENGTH: 18
<212> TYPE: DNA
<213> ORGANISM: Artificial Sequence
<220> FEATURE:
<223> OTHER INFORMATION: Synthetic

<400> SEQUENCE: 218
cacttcaccg tttttgaa                                                18

<210> SEQ ID NO 219
<211> LENGTH: 20
<212> TYPE: DNA
<213> ORGANISM: Artificial Sequence
<220> FEATURE:
<223> OTHER INFORMATION: Synthetic

<400> SEQUENCE: 219
```

-continued aacagcttgc tgtttcgctg                                           20

<210> SEQ ID NO 220
<211> LENGTH: 20
<212> TYPE: DNA
<213> ORGANISM: Artificial Sequence
<220> FEATURE:
<223> OTHER INFORMATION: Synthetic

<400> SEQUENCE: 220
ttcctccccg ctgaaagtac                                           20

<210> SEQ ID NO 221
<211> LENGTH: 20
<212> TYPE: DNA
<213> ORGANISM: Artificial Sequence
<220> FEATURE:
<223> OTHER INFORMATION: Synthetic

<400> SEQUENCE: 221
caggtcttag gatgctgacg                                           20

<210> SEQ ID NO 222
<211> LENGTH: 20
<212> TYPE: DNA
<213> ORGANISM: Artificial Sequence
<220> FEATURE:
<223> OTHER INFORMATION: Synthetic

<400> SEQUENCE: 222
aaggctatta accttgaggc                                           20

<210> SEQ ID NO 223
<211> LENGTH: 20
<212> TYPE: DNA
<213> ORGANISM: Artificial Sequence
<220> FEATURE:
<223> OTHER INFORMATION: Synthetic

<400> SEQUENCE: 223
agactatcta cttctggtgc                                           20

<210> SEQ ID NO 224
<211> LENGTH: 20
<212> TYPE: DNA
<213> ORGANISM: Artificial Sequence
<220> FEATURE:
<223> OTHER INFORMATION: Synthetic

<400> SEQUENCE: 224
atacaggtgc tgcatggctg                                           20

<210> SEQ ID NO 225
<211> LENGTH: 20
<212> TYPE: DNA
<213> ORGANISM: Artificial Sequence
<220> FEATURE:
<223> OTHER INFORMATION: Synthetic

<400> SEQUENCE: 225
gagtagcaat actcagcggc                                           20

<210> SEQ ID NO 226
<211> LENGTH: 20
<212> TYPE: DNA

```
<213> ORGANISM: Artificial Sequence
<220> FEATURE:
<223> OTHER INFORMATION: Synthetic

<400> SEQUENCE: 226
taccatcatc acattgctgc                                              20

<210> SEQ ID NO 227
<211> LENGTH: 20
<212> TYPE: DNA
<213> ORGANISM: Artificial Sequence
<220> FEATURE:
<223> OTHER INFORMATION: Synthetic

<400> SEQUENCE: 227
gagcttgctc ctggattcag                                              20

<210> SEQ ID NO 228
<211> LENGTH: 20
<212> TYPE: DNA
<213> ORGANISM: Artificial Sequence
<220> FEATURE:
<223> OTHER INFORMATION: Synthetic

<400> SEQUENCE: 228
gtaacgtcaa aacagcaagg                                              20

<210> SEQ ID NO 229
<211> LENGTH: 20
<212> TYPE: DNA
<213> ORGANISM: Artificial Sequence
<220> FEATURE:
<223> OTHER INFORMATION: Synthetic

<400> SEQUENCE: 229
agttaattag tggcagacgg                                              20

<210> SEQ ID NO 230
<211> LENGTH: 20
<212> TYPE: DNA
<213> ORGANISM: Artificial Sequence
<220> FEATURE:
<223> OTHER INFORMATION: Synthetic

<400> SEQUENCE: 230
actaaaccgc ctacgcactc                                              20

<210> SEQ ID NO 231
<211> LENGTH: 20
<212> TYPE: DNA
<213> ORGANISM: Artificial Sequence
<220> FEATURE:
<223> OTHER INFORMATION: Synthetic

<400> SEQUENCE: 231
agcttgctgc tttgctgacg                                              20

<210> SEQ ID NO 232
<211> LENGTH: 20
<212> TYPE: DNA
<213> ORGANISM: Artificial Sequence
<220> FEATURE:
<223> OTHER INFORMATION: Synthetic

<400> SEQUENCE: 232
taaccacaac accttcctcc                                              20
```

```
<210> SEQ ID NO 233
<211> LENGTH: 20
<212> TYPE: DNA
<213> ORGANISM: Artificial Sequence
<220> FEATURE:
<223> OTHER INFORMATION: Synthetic

<400> SEQUENCE: 233
gaacttgttc cttgggtggc                                        20

<210> SEQ ID NO 234
<211> LENGTH: 20
<212> TYPE: DNA
<213> ORGANISM: Artificial Sequence
<220> FEATURE:
<223> OTHER INFORMATION: Synthetic

<400> SEQUENCE: 234
ttaaccacct tcctccctac                                        20

<210> SEQ ID NO 235
<211> LENGTH: 20
<212> TYPE: DNA
<213> ORGANISM: Artificial Sequence
<220> FEATURE:
<223> OTHER INFORMATION: Synthetic

<400> SEQUENCE: 235
gtagtttact actttgccgg                                        20

<210> SEQ ID NO 236
<211> LENGTH: 20
<212> TYPE: DNA
<213> ORGANISM: Artificial Sequence
<220> FEATURE:
<223> OTHER INFORMATION: Synthetic

<400> SEQUENCE: 236
gagcgtatta aactcaaccc                                        20

<210> SEQ ID NO 237
<211> LENGTH: 20
<212> TYPE: DNA
<213> ORGANISM: Artificial Sequence
<220> FEATURE:
<223> OTHER INFORMATION: Synthetic

<400> SEQUENCE: 237
gcaaagtggc cctctgattc                                        20

<210> SEQ ID NO 238
<211> LENGTH: 20
<212> TYPE: DNA
<213> ORGANISM: Artificial Sequence
<220> FEATURE:
<223> OTHER INFORMATION: Synthetic

<400> SEQUENCE: 238
ccataaatga acccaacggc                                        20

<210> SEQ ID NO 239
<211> LENGTH: 20
<212> TYPE: DNA
<213> ORGANISM: Artificial Sequence
<220> FEATURE:
```

<223> OTHER INFORMATION: Synthetic

<400> SEQUENCE: 239
accggataca ccttcatacc                                                 20

<210> SEQ ID NO 240
<211> LENGTH: 20
<212> TYPE: DNA
<213> ORGANISM: Artificial Sequence
<220> FEATURE:
<223> OTHER INFORMATION: Synthetic

<400> SEQUENCE: 240
ccgcaatgac aagcatcacg                                                 20

<210> SEQ ID NO 241
<211> LENGTH: 20
<212> TYPE: DNA
<213> ORGANISM: Artificial Sequence
<220> FEATURE:
<223> OTHER INFORMATION: Synthetic

<400> SEQUENCE: 241
acgctccgat ttcacagttc                                                 20

<210> SEQ ID NO 242
<211> LENGTH: 20
<212> TYPE: DNA
<213> ORGANISM: Artificial Sequence
<220> FEATURE:
<223> OTHER INFORMATION: Synthetic

<400> SEQUENCE: 242
aagtccagca gtatcaaggg                                                 20

<210> SEQ ID NO 243
<211> LENGTH: 20
<212> TYPE: DNA
<213> ORGANISM: Artificial Sequence
<220> FEATURE:
<223> OTHER INFORMATION: Synthetic

<400> SEQUENCE: 243
tgggtttacc taacactacg                                                 20

<210> SEQ ID NO 244
<211> LENGTH: 20
<212> TYPE: DNA
<213> ORGANISM: Artificial Sequence
<220> FEATURE:
<223> OTHER INFORMATION: Synthetic

<400> SEQUENCE: 244
tagagtcgag ttacagaccg                                                 20

<210> SEQ ID NO 245
<211> LENGTH: 20
<212> TYPE: DNA
<213> ORGANISM: Artificial Sequence
<220> FEATURE:
<223> OTHER INFORMATION: Synthetic

<400> SEQUENCE: 245
atcatgagtt cacatgtccg                                                 20

<210> SEQ ID NO 246
<211> LENGTH: 18
<212> TYPE: DNA
<213> ORGANISM: Artificial Sequence
<220> FEATURE:
<223> OTHER INFORMATION: Synthetic

<400> SEQUENCE: 246
caatcggagt tcttcgtg                                                 18

<210> SEQ ID NO 247
<211> LENGTH: 20
<212> TYPE: DNA
<213> ORGANISM: Artificial Sequence
<220> FEATURE:
<223> OTHER INFORMATION: Synthetic

<400> SEQUENCE: 247
atcatgagtt cacatgtccg                                               20

<210> SEQ ID NO 248
<211> LENGTH: 18
<212> TYPE: DNA
<213> ORGANISM: Artificial Sequence
<220> FEATURE:
<223> OTHER INFORMATION: Synthetic

<400> SEQUENCE: 248
caatcggagt tcttcgtg                                                 18

<210> SEQ ID NO 249
<211> LENGTH: 17
<212> TYPE: DNA
<213> ORGANISM: Artificial Sequence
<220> FEATURE:
<223> OTHER INFORMATION: Synthetic

<400> SEQUENCE: 249
gccgtctact cttggcc                                                  17

<210> SEQ ID NO 250
<211> LENGTH: 18
<212> TYPE: DNA
<213> ORGANISM: Artificial Sequence
<220> FEATURE:
<223> OTHER INFORMATION: Synthetic

<400> SEQUENCE: 250
cctgcctcta ctgtactc                                                 18

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
acgggtgctt gcacctgg                                                 18

<210> SEQ ID NO 252
<211> LENGTH: 20
<212> TYPE: DNA
<213> ORGANISM: Artificial Sequence
<220> FEATURE:
<223> OTHER INFORMATION: Synthetic

```
<400> SEQUENCE: 252
cgactgtatt agagccaagg                                               20

<210> SEQ ID NO 253
<211> LENGTH: 20
<212> TYPE: DNA
<213> ORGANISM: Artificial Sequence
<220> FEATURE:
<223> OTHER INFORMATION: Synthetic

<400> SEQUENCE: 253
gttggccgat ggctgattag                                               20

<210> SEQ ID NO 254
<211> LENGTH: 20
<212> TYPE: DNA
<213> ORGANISM: Artificial Sequence
<220> FEATURE:
<223> OTHER INFORMATION: Synthetic

<400> SEQUENCE: 254
tctgccatac tctagcctgc                                               20

<210> SEQ ID NO 255
<211> LENGTH: 20
<212> TYPE: DNA
<213> ORGANISM: Artificial Sequence
<220> FEATURE:
<223> OTHER INFORMATION: Synthetic

<400> SEQUENCE: 255
acatgcaagt cgtacgagag                                               20

<210> SEQ ID NO 256
<211> LENGTH: 20
<212> TYPE: DNA
<213> ORGANISM: Artificial Sequence
<220> FEATURE:
<223> OTHER INFORMATION: Synthetic

<400> SEQUENCE: 256
acacgtcatt tattcctccc                                               20

<210> SEQ ID NO 257
<211> LENGTH: 20
<212> TYPE: DNA
<213> ORGANISM: Artificial Sequence
<220> FEATURE:
<223> OTHER INFORMATION: Synthetic

<400> SEQUENCE: 257
acgaaccttc gggttagtgg                                               20

<210> SEQ ID NO 258
<211> LENGTH: 20
<212> TYPE: DNA
<213> ORGANISM: Artificial Sequence
<220> FEATURE:
<223> OTHER INFORMATION: Synthetic

<400> SEQUENCE: 258
tcaagtaccg tcagatcttc                                               20

<210> SEQ ID NO 259
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 259
aaaggcctac caaggcttcg                                                  20

<210> SEQ ID NO 260
<211> LENGTH: 20
<212> TYPE: DNA
<213> ORGANISM: Artificial Sequence
<220> FEATURE:
<223> OTHER INFORMATION: Synthetic

<400> SEQUENCE: 260
ggcactctct cgtttccaag                                                  20

<210> SEQ ID NO 261
<211> LENGTH: 20
<212> TYPE: DNA
<213> ORGANISM: Artificial Sequence
<220> FEATURE:
<223> OTHER INFORMATION: Synthetic

<400> SEQUENCE: 261
aaaggcttac caaggcattg                                                  20

<210> SEQ ID NO 262
<211> LENGTH: 17
<212> TYPE: DNA
<213> ORGANISM: Artificial Sequence
<220> FEATURE:
<223> OTHER INFORMATION: Synthetic

<400> SEQUENCE: 262
cctccggttt cccagag                                                     17

<210> SEQ ID NO 263
<211> LENGTH: 20
<212> TYPE: DNA
<213> ORGANISM: Artificial Sequence
<220> FEATURE:
<223> OTHER INFORMATION: Synthetic

<400> SEQUENCE: 263
gtaacaggtc tttcgggatg                                                  20

<210> SEQ ID NO 264
<211> LENGTH: 20
<212> TYPE: DNA
<213> ORGANISM: Artificial Sequence
<220> FEATURE:
<223> OTHER INFORMATION: Synthetic

<400> SEQUENCE: 264
caagactttt cgttccgtac                                                  20

<210> SEQ ID NO 265
<211> LENGTH: 20
<212> TYPE: DNA
<213> ORGANISM: Artificial Sequence
<220> FEATURE:
<223> OTHER INFORMATION: Synthetic

<400> SEQUENCE: 265
```

| | |
|---|---|
| tctttcaccg gagcttgctc | 20 |

<210> SEQ ID NO 266
<211> LENGTH: 20
<212> TYPE: DNA
<213> ORGANISM: Artificial Sequence
<220> FEATURE:
<223> OTHER INFORMATION: Synthetic

<400> SEQUENCE: 266

| | |
|---|---|
| ctctcatcct tgttcttctc | 20 |

<210> SEQ ID NO 267
<211> LENGTH: 20
<212> TYPE: DNA
<213> ORGANISM: Artificial Sequence
<220> FEATURE:
<223> OTHER INFORMATION: Synthetic

<400> SEQUENCE: 267

| | |
|---|---|
| acggtcgcgt aacacgtaag | 20 |

<210> SEQ ID NO 268
<211> LENGTH: 20
<212> TYPE: DNA
<213> ORGANISM: Artificial Sequence
<220> FEATURE:
<223> OTHER INFORMATION: Synthetic

<400> SEQUENCE: 268

| | |
|---|---|
| cgtcaaattt cttcccactc | 20 |

<210> SEQ ID NO 269
<211> LENGTH: 20
<212> TYPE: DNA
<213> ORGANISM: Artificial Sequence
<220> FEATURE:
<223> OTHER INFORMATION: Synthetic

<400> SEQUENCE: 269

| | |
|---|---|
| atgaagctac ttcggtagtg | 20 |

<210> SEQ ID NO 270
<211> LENGTH: 20
<212> TYPE: DNA
<213> ORGANISM: Artificial Sequence
<220> FEATURE:
<223> OTHER INFORMATION: Synthetic

<400> SEQUENCE: 270

| | |
|---|---|
| tgtaggtacc gtcactttcg | 20 |

<210> SEQ ID NO 271
<211> LENGTH: 20
<212> TYPE: DNA
<213> ORGANISM: Artificial Sequence
<220> FEATURE:
<223> OTHER INFORMATION: Synthetic

<400> SEQUENCE: 271

| | |
|---|---|
| atgaagcacc ttcgggtgtg | 20 |

<210> SEQ ID NO 272
<211> LENGTH: 20
<212> TYPE: DNA
<213> ORGANISM: Artificial Sequence

```
<220> FEATURE:
<223> OTHER INFORMATION: Synthetic

<400> SEQUENCE: 272
tgcaggtacc gtcactttcg                                                 20

<210> SEQ ID NO 273
<211> LENGTH: 20
<212> TYPE: DNA
<213> ORGANISM: Artificial Sequence
<220> FEATURE:
<223> OTHER INFORMATION: Synthetic

<400> SEQUENCE: 273
gatctttgat cttagtggcg                                                 20

<210> SEQ ID NO 274
<211> LENGTH: 20
<212> TYPE: DNA
<213> ORGANISM: Artificial Sequence
<220> FEATURE:
<223> OTHER INFORMATION: Synthetic

<400> SEQUENCE: 274
tcaagtaccg tcagaacttc                                                 20

<210> SEQ ID NO 275
<211> LENGTH: 18
<212> TYPE: DNA
<213> ORGANISM: Artificial Sequence
<220> FEATURE:
<223> OTHER INFORMATION: Synthetic

<400> SEQUENCE: 275
aacgtaccca agagtggg                                                   18

<210> SEQ ID NO 276
<211> LENGTH: 20
<212> TYPE: DNA
<213> ORGANISM: Artificial Sequence
<220> FEATURE:
<223> OTHER INFORMATION: Synthetic

<400> SEQUENCE: 276
aaggatatta gcctctaccg                                                 20

<210> SEQ ID NO 277
<211> LENGTH: 20
<212> TYPE: DNA
<213> ORGANISM: Artificial Sequence
<220> FEATURE:
<223> OTHER INFORMATION: Synthetic

<400> SEQUENCE: 277
tgaagttcct tcgggaatgg                                                 20

<210> SEQ ID NO 278
<211> LENGTH: 20
<212> TYPE: DNA
<213> ORGANISM: Artificial Sequence
<220> FEATURE:
<223> OTHER INFORMATION: Synthetic

<400> SEQUENCE: 278
ttcttcccta ctgaaagagg                                                 20
```

<210> SEQ ID NO 279
<211> LENGTH: 20
<212> TYPE: DNA
<213> ORGANISM: Artificial Sequence
<220> FEATURE:
<223> OTHER INFORMATION: Synthetic

<400> SEQUENCE: 279
ctcatcagca atggtgggag                                               20

<210> SEQ ID NO 280
<211> LENGTH: 19
<212> TYPE: DNA
<213> ORGANISM: Artificial Sequence
<220> FEATURE:
<223> OTHER INFORMATION: Synthetic

<400> SEQUENCE: 280
tcaactccgg aggagaacc                                                19

<210> SEQ ID NO 281
<211> LENGTH: 20
<212> TYPE: DNA
<213> ORGANISM: Artificial Sequence
<220> FEATURE:
<223> OTHER INFORMATION: Synthetic

<400> SEQUENCE: 281
ggcagcacgg tctagtttac                                               20

<210> SEQ ID NO 282
<211> LENGTH: 20
<212> TYPE: DNA
<213> ORGANISM: Artificial Sequence
<220> FEATURE:
<223> OTHER INFORMATION: Synthetic

<400> SEQUENCE: 282
tcaaatcctc ctccccactg                                               20

<210> SEQ ID NO 283
<211> LENGTH: 20
<212> TYPE: DNA
<213> ORGANISM: Artificial Sequence
<220> FEATURE:
<223> OTHER INFORMATION: Synthetic

<400> SEQUENCE: 283
gtcagacttc ggtctgattg                                               20

<210> SEQ ID NO 284
<211> LENGTH: 20
<212> TYPE: DNA
<213> ORGANISM: Artificial Sequence
<220> FEATURE:
<223> OTHER INFORMATION: Synthetic

<400> SEQUENCE: 284
ggtacttctt cccgagcaac                                               20

<210> SEQ ID NO 285
<211> LENGTH: 20
<212> TYPE: DNA
<213> ORGANISM: Artificial Sequence
<220> FEATURE:
<223> OTHER INFORMATION: Synthetic

<400> SEQUENCE: 285
atgtagcaat acaggacagc                                                              20

<210> SEQ ID NO 286
<211> LENGTH: 20
<212> TYPE: DNA
<213> ORGANISM: Artificial Sequence
<220> FEATURE:
<223> OTHER INFORMATION: Synthetic

<400> SEQUENCE: 286
cgtacatttg attccctacg                                                              20

<210> SEQ ID NO 287
<211> LENGTH: 20
<212> TYPE: DNA
<213> ORGANISM: Artificial Sequence
<220> FEATURE:
<223> OTHER INFORMATION: Synthetic

<400> SEQUENCE: 287
atgaagctgg agcttgctcc                                                              20

<210> SEQ ID NO 288
<211> LENGTH: 18
<212> TYPE: DNA
<213> ORGANISM: Artificial Sequence
<220> FEATURE:
<223> OTHER INFORMATION: Synthetic

<400> SEQUENCE: 288
gcgagctcat ccttgacc                                                                18

<210> SEQ ID NO 289
<211> LENGTH: 18
<212> TYPE: DNA
<213> ORGANISM: Artificial Sequence
<220> FEATURE:
<223> OTHER INFORMATION: Synthetic

<400> SEQUENCE: 289
acgggagcaa tcctggtg                                                                18

<210> SEQ ID NO 290
<211> LENGTH: 20
<212> TYPE: DNA
<213> ORGANISM: Artificial Sequence
<220> FEATURE:
<223> OTHER INFORMATION: Synthetic

<400> SEQUENCE: 290
ccactgtatt agagcagacc                                                              20

<210> SEQ ID NO 291
<211> LENGTH: 20
<212> TYPE: DNA
<213> ORGANISM: Artificial Sequence
<220> FEATURE:
<223> OTHER INFORMATION: Synthetic

<400> SEQUENCE: 291
acggcttcgg cctagtaaag                                                              20

<210> SEQ ID NO 292

```
<211> LENGTH: 20
<212> TYPE: DNA
<213> ORGANISM: Artificial Sequence
<220> FEATURE:
<223> OTHER INFORMATION: Synthetic

<400> SEQUENCE: 292
agggctgttc accctaatgg                                                    20

<210> SEQ ID NO 293
<211> LENGTH: 20
<212> TYPE: DNA
<213> ORGANISM: Artificial Sequence
<220> FEATURE:
<223> OTHER INFORMATION: Synthetic

<400> SEQUENCE: 293
ttaacttaag tggcggacgg                                                    20

<210> SEQ ID NO 294
<211> LENGTH: 20
<212> TYPE: DNA
<213> ORGANISM: Artificial Sequence
<220> FEATURE:
<223> OTHER INFORMATION: Synthetic

<400> SEQUENCE: 294
ggtacacgtc gttttattcc                                                    20

<210> SEQ ID NO 295
<211> LENGTH: 18
<212> TYPE: DNA
<213> ORGANISM: Artificial Sequence
<220> FEATURE:
<223> OTHER INFORMATION: Synthetic

<400> SEQUENCE: 295
taacgcgggg caacctgg                                                      18

<210> SEQ ID NO 296
<211> LENGTH: 18
<212> TYPE: DNA
<213> ORGANISM: Artificial Sequence
<220> FEATURE:
<223> OTHER INFORMATION: Synthetic

<400> SEQUENCE: 296
gggtattagc ccagagcg                                                      18

<210> SEQ ID NO 297
<211> LENGTH: 20
<212> TYPE: DNA
<213> ORGANISM: Artificial Sequence
<220> FEATURE:
<223> OTHER INFORMATION: Synthetic

<400> SEQUENCE: 297
agagtttgat cctggctcag                                                    20

<210> SEQ ID NO 298
<211> LENGTH: 20
<212> TYPE: DNA
<213> ORGANISM: Artificial Sequence
<220> FEATURE:
<223> OTHER INFORMATION: Synthetic

<400> SEQUENCE: 298
```
acggaggtag caatacctta                                              20

<210> SEQ ID NO 299
<211> LENGTH: 20
<212> TYPE: DNA
<213> ORGANISM: Artificial Sequence
<220> FEATURE:
<223> OTHER INFORMATION: Synthetic

<400> SEQUENCE: 299
gtgcttcttc ttccggtacc                                              20

<210> SEQ ID NO 300
<211> LENGTH: 20
<212> TYPE: DNA
<213> ORGANISM: Artificial Sequence
<220> FEATURE:
<223> OTHER INFORMATION: Synthetic

<400> SEQUENCE: 300
ttcggttatg ttgatggcga                                              20

<210> SEQ ID NO 301
<211> LENGTH: 20
<212> TYPE: DNA
<213> ORGANISM: Artificial Sequence
<220> FEATURE:
<223> OTHER INFORMATION: Synthetic

<400> SEQUENCE: 301
tcgggtaacg tcaataaacc                                              20

<210> SEQ ID NO 302
<211> LENGTH: 18
<212> TYPE: DNA
<213> ORGANISM: Artificial Sequence
<220> FEATURE:
<223> OTHER INFORMATION: Synthetic

<400> SEQUENCE: 302
aaccccggtg gcgagtgg                                                18

<210> SEQ ID NO 303
<211> LENGTH: 18
<212> TYPE: DNA
<213> ORGANISM: Artificial Sequence
<220> FEATURE:
<223> OTHER INFORMATION: Synthetic

<400> SEQUENCE: 303
aaccctggtg gcgagtgg                                                18

<210> SEQ ID NO 304
<211> LENGTH: 19
<212> TYPE: DNA
<213> ORGANISM: Artificial Sequence
<220> FEATURE:
<223> OTHER INFORMATION: Synthetic

<400> SEQUENCE: 304
ttcttacggt accgtcatg                                               19

<210> SEQ ID NO 305
<211> LENGTH: 20
<212> TYPE: DNA

```
<213> ORGANISM: Artificial Sequence
<220> FEATURE:
<223> OTHER INFORMATION: Synthetic

<400> SEQUENCE: 305
gagcgatgaa gtttcttcgg                                          20

<210> SEQ ID NO 306
<211> LENGTH: 20
<212> TYPE: DNA
<213> ORGANISM: Artificial Sequence
<220> FEATURE:
<223> OTHER INFORMATION: Synthetic

<400> SEQUENCE: 306
agccggtgct tcttttgtag                                          20

<210> SEQ ID NO 307
<211> LENGTH: 20
<212> TYPE: DNA
<213> ORGANISM: Artificial Sequence
<220> FEATURE:
<223> OTHER INFORMATION: Synthetic

<400> SEQUENCE: 307
ggtaacaggt taagctgacg                                          20

<210> SEQ ID NO 308
<211> LENGTH: 20
<212> TYPE: DNA
<213> ORGANISM: Artificial Sequence
<220> FEATURE:
<223> OTHER INFORMATION: Synthetic

<400> SEQUENCE: 308
cagagtatta atccgaagcg                                          20

<210> SEQ ID NO 309
<211> LENGTH: 20
<212> TYPE: DNA
<213> ORGANISM: Artificial Sequence
<220> FEATURE:
<223> OTHER INFORMATION: Synthetic

<400> SEQUENCE: 309
ggtctagttt actagatggg                                          20

<210> SEQ ID NO 310
<211> LENGTH: 20
<212> TYPE: DNA
<213> ORGANISM: Artificial Sequence
<220> FEATURE:
<223> OTHER INFORMATION: Synthetic

<400> SEQUENCE: 310
ttcttctgtg ggtaacgtcc                                          20

<210> SEQ ID NO 311
<211> LENGTH: 20
<212> TYPE: DNA
<213> ORGANISM: Artificial Sequence
<220> FEATURE:
<223> OTHER INFORMATION: Synthetic

<400> SEQUENCE: 311
catcggaacg taccttatcg                                          20
```

<210> SEQ ID NO 312
<211> LENGTH: 20
<212> TYPE: DNA
<213> ORGANISM: Artificial Sequence
<220> FEATURE:
<223> OTHER INFORMATION: Synthetic

<400> SEQUENCE: 312
cgcagtctgt gttagagctg                                               20

<210> SEQ ID NO 313
<211> LENGTH: 20
<212> TYPE: DNA
<213> ORGANISM: Artificial Sequence
<220> FEATURE:
<223> OTHER INFORMATION: Synthetic

<400> SEQUENCE: 313
cgtgagaatc taccettagg                                               20

<210> SEQ ID NO 314
<211> LENGTH: 20
<212> TYPE: DNA
<213> ORGANISM: Artificial Sequence
<220> FEATURE:
<223> OTHER INFORMATION: Synthetic

<400> SEQUENCE: 314
gcttgcatcc tctgtattac                                               20

<210> SEQ ID NO 315
<211> LENGTH: 18
<212> TYPE: DNA
<213> ORGANISM: Artificial Sequence
<220> FEATURE:
<223> OTHER INFORMATION: Synthetic

<400> SEQUENCE: 315
tgtcgtcagc tcgtgtcg                                                 18

<210> SEQ ID NO 316
<211> LENGTH: 18
<212> TYPE: DNA
<213> ORGANISM: Artificial Sequence
<220> FEATURE:
<223> OTHER INFORMATION: Synthetic

<400> SEQUENCE: 316
aaggaggtga tccagccg                                                 18

<210> SEQ ID NO 317
<211> LENGTH: 1442
<212> TYPE: DNA
<213> ORGANISM: Escherichia coli

<400> SEQUENCE: 317
aaattgaaga gtttgatcat ggctcagatt gaacgctggc ggcaggccta acacatgcaa      60
gtcgaacggt aacaggaaga agcttgcttc tttgctgacg agtggcggac gggtgagtaa     120
tgtctgggaa actgcctgat ggagggggat aactactgga aacggtagct aataccgcat     180
aacgtcgcaa gaccaaagag ggggaccttc gggcctcttg ccatcggatg tgcccagatg     240
ggattagcta gtaggtgggg taacggctca cctaggcgac gatccctagc tggtctgaga     300

| | |
|---|---:|
| ggatgaccag ccacactgga actgagacac ggtccagact cctacgggag gcagcagtgg | 360 |
| ggaatattgc acaatgggcg caagcctgat gcagccatgc cgcgtgtatg aagaaggcct | 420 |
| tcgggttgta aagtactttc agcggggagg aagggagtaa agttaatacc tttgctcatt | 480 |
| gacgttaccc gcagaagaag caccggctaa ctccgtgcca gcagccgcgg taatacggag | 540 |
| ggtgcaagcg ttaatcggaa ttactgggcg taaagcgcac gcaggcggtt tgttaagtca | 600 |
| gatgtgaaat ccccgggctc aacctgggaa ctgcatctga tactggcaag cttgagtctc | 660 |
| gtagaggggg gtagaattcc aggtgtagcg gtgaaatgcg tagagatctg gaggaatacc | 720 |
| ggtggcgaag gcggcccccct ggacgaagac tgacgctcag gtgcgaaagc gtggggagca | 780 |
| aacaggatta gataccctgg tagtccacgc cgtaaacgat gtcgacttgg aggttgtgcc | 840 |
| cttgaggcgt ggcttccgga gctaacgcgt taagtcgacc gcctgggag tacgccgca | 900 |
| aggttaaaac tcaaatgaat tgacgggggc cgcacaagc ggtggagcat gtggtttaat | 960 |
| tcgatgcaac gcgaagaacc ttacctggtc ttgacatcca cggaagtttt cagagatgag | 1020 |
| aatgtgcctt cgggaaccgt gagacaggtg ctgcatggct gtcgtcagct cgtgttgtga | 1080 |
| aatgttgggt taagtcccgc aacgagcgca acccttatcc tttgttgcca gcggtccggc | 1140 |
| cgggaactca aaggagactg ccagtgataa actggaggaa ggtggggatg acgtcaagtc | 1200 |
| atcatggccc ttacgaccag ggctacacac gtgctacaat ggcgcataca agagaagcg | 1260 |
| acctcgcgag agcaagcgga cctcataaag tgcgtcgtag tccggattgg agtctgcaac | 1320 |
| tcgactccat gaagtcggaa tcgctagtaa tcgtggatca gaatgccacg gtgaatacgt | 1380 |
| tcccgggcct tgtacacacc gcccgtcaca ccatgggagt gggttgcaaa agaagtaggt | 1440 |
| ag | 1442 |

<210> SEQ ID NO 318
<211> LENGTH: 1798
<212> TYPE: DNA
<213> ORGANISM: Saccharomyces cerevisiae

<400> SEQUENCE: 318

| | |
|---|---:|
| tatctggttg atcctgccag tagtcatatg cttgtctcaa agattaagcc atgcatgtct | 60 |
| aagtataagc aatttataca gtgaaactgc gaatggctca ttaaatcagt tatcgtttat | 120 |
| ttgatagttc ctttactaca tggtataacc gtggtaattc tagagctaat acatgcttaa | 180 |
| aatctcgacc ctttggaaga gatgtattta ttagataaaa aatcaatgtc ttcgcactct | 240 |
| ttgatgattc ataataactt ttcgaatcgc atggccttgt gctggcgatg gttcattcaa | 300 |
| atttctgccc tatcaacttt cgatggtagg atagtggcct accatggttt caacgggtaa | 360 |
| cggggaataa gggttcgatt ccggagaggg agcctgagaa acggctacca catccaagga | 420 |
| aggcagcagg cgcgcaaatt acccaatcct aattcaggga ggtagtgaca ataaataacg | 480 |
| atacagggcc cattcgggtc ttgtaattgg aatgagtaca atgtaaatac cttaacgagg | 540 |
| aacaattgga gggcaagtct ggtgccagca gccgcggtaa ttccagctcc aatagcgtat | 600 |
| attaaagttg ttgcagttaa aaagctcgta gttgaacttt gggcccggtt ggccggtccg | 660 |
| attttttcgt gtactggatt tccaacgggg ccttttccttc tggctaacct tgagtccttg | 720 |
| tggctcttgg cgaaccagga cttttacttt gaaaaaatta gagtgttcaa gcaggcgta | 780 |
| ttgctcgaat atattagcat ggaataatag aataggacgt ttggttctat tttgttggtt | 840 |
| tctaggacca tcgtaatgat taatagggac ggtcgggggc atcggtattc aattgtcgag | 900 |
| gtgaaattct tggatttatt gaagactaac tactgcgaaa gcatttgcca aggacgtttt | 960 |

```
cattaatcaa gaacgaaagt taggggatcg aagatgatct ggtaccgtcg tagtcttaac    1020
cataaactat gccgactaga tcgggtggtg ttttttttaat gacccactcg gtaccttacg   1080
agaaatcaaa gtctttgggt tctgggggga gtatggtcgc aaggctgaaa cttaaaggaa    1140
ttgacggaag ggcaccacta ggagtggagc ctgcggctaa tttgactcaa cacggggaaa    1200
ctcaccaggt ccagacacaa taaggattga cagattgaga gctctttctt gattttgtgg    1260
gtggtggtgc atggccgttt ctcagttggt ggagtgattt gtctgcttaa ttgcgataac    1320
gaacgagacc ttaacctact aaatagtggt gctagcattt gctggttatc cacttcttag    1380
agggactatc ggtttcaagc cgatggaagt ttgaggcaat aacaggtctg tgatgccctt    1440
agaacgttct gggccgcacg cgcgctacac tgacggagcc agcgagtcta accttggccg    1500
agaggtcttg gtaatcttgt gaaactccgt cgtgctgggg atagagcatt gtaattattg    1560
ctcttcaacg aggaattcct agtaagcgca agtcatcagc ttgcgttgat tacgtccctg    1620 cccttgtac acaccgcccg tcgctagtac cgattgaatg gcttagtgag gcctcaggat     1680
ctgcttagag aaggggggcaa ctccatctca gagcggagaa tttggacaaa cttggtcatt   1740
tagaggaact aaaagtcgta acaaggtttc cgtaggtgaa cctgcggaag gatcatta     1798
```

<210> SEQ ID NO 319
<211> LENGTH: 101
<212> TYPE: DNA
<213> ORGANISM: Escherichia coli

<400> SEQUENCE: 319

```
aacacatgca agtcgaacgg taacaggaag aagcttgctt ctttgctgac gagtggcgga    60
cgggtgagta atgtctggga aactgcctga tggagggga t                        101
```

<210> SEQ ID NO 320
<211> LENGTH: 91
<212> TYPE: DNA
<213> ORGANISM: Escherichia coli

<400> SEQUENCE: 320

```
aaacggtagc taataccgca taacgtcgca agaccaaaga ggggggaccttt cgggcctctt   60 gccatcggat gtgcccagat gggattagct a                                   91
```

<210> SEQ ID NO 321
<211> LENGTH: 81
<212> TYPE: DNA
<213> ORGANISM: Escherichia coli

<400> SEQUENCE: 321

```
aaagtacttt cagcggggag gaagggagta aagttaatac ctttgctcat tgacgttacc    60
cgcagaagaa gcaccggcta a                                              81
```

<210> SEQ ID NO 322
<211> LENGTH: 61
<212> TYPE: DNA
<213> ORGANISM: Escherichia coli

<400> SEQUENCE: 322

```
tgtcgacttg gaggttgtgc ccttgaggcg tggcttccgg agctaacgcg ttaagtcgac    60
c                                                                    61
```

<210> SEQ ID NO 323

```
<211> LENGTH: 61
<212> TYPE: DNA
<213> ORGANISM: Escherichia coli

<400> SEQUENCE: 323
caacgagcgc aaccttatc ctttgttgcc agcggtccgg ccgggaactc aaaggagact      60
g                                                                     61

<210> SEQ ID NO 324
<211> LENGTH: 501
<212> TYPE: DNA
<213> ORGANISM: Saccharomyces cerevisiae

<400> SEQUENCE: 324
catgcatgtc taagtataag caatttatac agtgaaactg cgaatggctc attaaatcag     60
ttatcgttta tttgatagtt cctttactac atggtataac cgtggtaatt ctagagctaa   120
tacatgctta aaatctcgac cctttggaag agatgtattt attagataaa aaatcaatgt   180
cttcgcactc tttgatgatt cataataact tttcgaatcg catggccttg tgctggcgat   240
ggttcattca aatttctgcc ctatcaactt tcgatggtag gatagtggcc taccatggtt   300
tcaacgggta acgggaata agggttcgat tccggagagg gagcctgaga acggctacc     360 acatccaagg aaggcagcag gcgcgcaaat tacccaatcc taattcaggg aggtagtgac   420
aataaataac gatacagggc ccattcgggt cttgtaattg gaatgagtac aatgtaaata   480
ccttaacgag gaacaattgg a                                              501

<210> SEQ ID NO 325
<211> LENGTH: 201
<212> TYPE: DNA
<213> ORGANISM: Saccharomyces cerevisiae

<400> SEQUENCE: 325
tattaaagtt gttgcagtta aaaagctcgt agttgaactt tgggcccggt tggccggtcc     60
gattttttcg tgtactggat ttccaacggg gcctttcctt ctggctaacc ttgagtcctt   120
gtggctcttg gcgaaccagg acttttactt tgaaaaaatt agagtgttca aagcaggcgt   180
attgctcgaa tatattagca t                                              201

<210> SEQ ID NO 326
<211> LENGTH: 71
<212> TYPE: DNA
<213> ORGANISM: Saccharomyces cerevisiae

<400> SEQUENCE: 326
tggaataata gaataggacg tttggttcta ttttgttggt ttctaggacc atcgtaatga     60
ttaataggga c                                                          71

<210> SEQ ID NO 327
<211> LENGTH: 101
<212> TYPE: DNA
<213> ORGANISM: Saccharomyces cerevisiae

<400> SEQUENCE: 327
tggtaccgtc gtagtcttaa ccataaacta tgccgactag atcgggtggt gttttttaa     60 tgacccactc ggtaccttac gagaaatcaa agtctttggg t                       101

<210> SEQ ID NO 328
<211> LENGTH: 101
```

-continued

```
<212> TYPE: DNA
<213> ORGANISM: Saccharomyces cerevisiae

<400> SEQUENCE: 328
tgctagcatt tgctggttat ccacttctta gagggactat cggtttcaag ccgatggaag       60
tttgaggcaa taacaggtct gtgatgccct tagaacgttc t                          101
```

NUCLEIC ACID ARRAYS TO MONITOR WATER AND OTHER ECOSYSTEMS

RELATED APPLICATIONS

This application is a continuation-in-part of U.S. patent application Ser. No. 10/131,618, filed Apr. 24, 2002 now abandoned. The disclosure of U.S. patent application Ser. No. 10/131,618, is hereby incorporated by reference in its entirety.

FEDERAL FUNDING

Parts of this work were supported by federal funding in the form of a Cooperative Agreement #82946501 with the Environmental Protection Agency to C. Neal Stewart, Vincent C. Henrich and Parke A. Rublee and an Environmental Protection Agency STAR Grant #R831627 to Parke A. Rublee.

FIELD OF THE INVENTION

The present invention relates to nucleic acid arrays to monitor water and other ecosystems.

BACKGROUND

As the threat of bioterrorist activities has become evident in recent years, concern about the vulnerability of ecosystems such as municipal water supplies to deliberate contamination has grown. Additionally, human development can result in chemicals, waste, and/or agricultural runoff being introduced into the ecosystem. Increases in population may lead to over-harvesting of marine resources, landscape alterations that alter the ecosystem, and the introduction of living and non-living contaminants into the ecosystem (Mallin, J. M., et al. 2000, *Marine Pollution Bulletin*, 41:56–75). For example, spills from concentrated animal feeding operations can degrade water quality and stimulate algal blooms (Mallin, M. A., 2000, *American Scientist*, 88:26–37). Also, over-development of coastal areas may introduce coliform bacteria, and the introduction of nutrients and or chemical compounds may lead to eutrophication or other changes in microbial communities (Mallin, M. A., et al. 2000, *Ecological Applications*, 10:1047–1056; Paerl, H. W., et al. 2003, *FEMS Microbiology Ecology*, 46:233–246; DeLorenzo, M. E., et al., 1999, *Environmental Toxicology and Chemistry*, 18:2824–2835).

Reservoirs, recreational lakes, and coastal areas can be difficult to secure against accidental or intentional contamination. Further, the contamination of a water source has the propensity to impact a relatively large population, and water filtration systems may not sufficiently alleviate the threat. Perhaps most troubling is the lack of a real-time test to detect the agents that are most likely to contaminate water supplies. The turnaround times for culturing microbes is slow enough that consumption of contaminated water may occur before the test results are known. Also, the expense involved in frequent monitoring of the water supply with currently available laboratory tests can be prohibitive.

As yet, there has not been a large-scale, deliberate contamination of a municipal water source. However, sporadic and relatively confined natural contaminations have demonstrated the importance in being able to monitor the water supply. The number of outbreaks attributable to contaminated drinking water supplies more than doubled in 1999–2000 over the previous two-year period, with contamination of well water also on the rise. In addition, recreational water sources have also reported significant increases in contamination (Bowman, 2002, Outbreaks of waterborne illnesses on the rise in US, *Scripps-Howard News Service*, Nov. 23, 2002). These incidents of water contamination were exacerbated by the difficulty in pinpointing the cause of the outbreak and subsequent misdiagnosis of the symptoms, illustrating the importance of "early warning" diagnostics of water supplies.

A number of microbial genome sequencing projects have been initiated to characterize pathogenic organisms. Although identification and characterization of genomic sequence data for individual pathogens may provide for the identification of specific microbes, such targeted testing fails to provide a comprehensive, economically feasible system for monitoring ecosystems of interest, such as municipal water supplies. The accuracy of a molecular diagnostic test for a microbe may be compromised where the pathogenic agent is endemic, or possesses substantial genetic similarity to non-pathogenic organisms (Leff et al., 1995, *Appl. Environ. Microbiol.*, 61:1634–1636; Xiao et al, 1999, *Appl Environ. Microbiol.*, 65:3386–3391). Also, although some putative contaminants of water have been identified, anticipating all possible contaminants is not feasible, and thus, specific tests are inherently limited.

Thus, there is a need for devices and methods that enable real-time monitoring of water supplies and other ecosystems of interest. The monitoring system should allow for detection of known, as well as unknown, contaminants. The monitoring system should be available in a format that is accessible for routine monitoring, as well as for rapid testing in response to a specific event.

SUMMARY

The present invention provides devices and systems for monitoring water and other ecosystems. The present invention may be embodied in a variety of ways.

One embodiment of the present invention comprises an array for monitoring an ecosystem comprising a plurality of oligonucleotides immobilized at known locations on a substrate, such that each location on the array comprises an oligonucleotide having a sequence derived from a single, predetermined microbial operational taxonomic unit (OTU).

In another embodiment, the present invention may comprise a device for monitoring water quality comprising an array, wherein the array comprises a plurality of oligonucleotides immobilized at known locations on a substrate, and wherein each location on the array comprises an oligonucleotide having a sequence that is derived from a single, predetermined microbial operational taxonomic unit (OTU).

Another embodiment of the present invention comprises a system for monitoring an ecosystem of interest. The system may comprise an array comprising a plurality of oligonucleotides immobilized at known locations on a substrate. In one embodiment, the array may be designed such that each location on the array comprises an oligonucleotide having a sequence derived from a single, predetermined microbial operational taxonomic unit (OTU). The system may further include a device able to measure hybridization of a DNA sample to the array. Also, the system may include a DNA sample for hybridizing to the array. In one embodiment, the ecosystem may comprise a body of water.

Yet other embodiments of the present invention comprise methods for monitoring ecosystems. The method may comprise the step of generating an array comprising a plurality of oligonucleotides immobilized at known locations on a substrate, such that each location on the array comprises an oligonucleotide having a sequence derived from a single predetermined microbial operational taxonomic unit (OTU). The method may also comprise the step of preparing a nucleic acid sample derived from a water sample of interest and hybridizing the nucleic acid sample to the array. Also, the method may comprise the step of measuring hybridization of the nucleic acid sample to the array, and correlating the hybridization of the nucleic acid to the array with a parameter that comprises at least part of the ecosystem. In one embodiment, the ecosystem of interest comprises a body of water.

In yet another embodiment, the present invention comprises a method of analyzing a pattern to evaluate the status of a biosystem. The method may comprise the step of measuring hybridization of a DNA sample to an array of oligonucleotides immobilized at known locations on a substrate, wherein each location on the array comprises an oligonucleotide having a sequence that is derived from a single, predetermined microbial operational taxonomic unit (OTU), and correlating the hybridization of the DNA to the array with a parameter that comprises at least part of the ecosystem. A single change in the pattern of hybridization to the array for a first DNA sample isolated from an ecosystem of interest as compared to a second DNA sample isolated from an ecosystem of interest may be associated with a change in one parameter, or a plurality of parameters. Additionally or alternatively, a plurality of changes in the pattern of hybridization to the array for a first DNA sample isolated from an ecosystem of interest as compared to a second DNA sample isolated from an ecosystem of interest is associated with a change in one or more parameters. Samples may vary by location of the ecosystem, the time of sampling of a single ecosystem, or the location of sampling within a single ecosystem.

Embodiments of the present invention also comprise methods for identifying and/or generating bioindicators for ecosystems of interest. In one embodiment, a method of generating a bioindicator may comprise preparing a nucleic acid sample comprising a plurality of DNA molecules from an ecosystem of interest. The method may also comprise determining the sequence of at least some of the plurality of DNA molecules in the isolated DNA sample. The method may further comprise grouping the DNA sequences into operational taxonomic units (OTUs). Also, the method may comprise identifying at least one nucleic acid sequence that is specific to a single OTU. In one embodiment, the ecosystem of interest comprises a body of water.

Embodiments of the present invention also comprise bioindicators isolated using the methods and systems of the present invention. In one embodiment, the present invention comprises a bioindicator, or a collection of bioindicators, for the analysis of an ecosystem of interest, wherein a bioindicator comprises an isolated nucleic acid having a sequence derived from a single predetermined microbial operational taxonomic unit.

In yet another embodiment, the present invention also comprises a method to prepare a nucleic acid sample from a biosystem of interest, the nucleic acid sample comprising a plurality of bioindicator DNA sequences, comprising the step of amplifying a DNA sample isolated from a biosystem with a plurality of primers that have the ability to specifically amplify nucleic acid sequences comprising bioindicators. Also, in an embodiment, the present invention comprises an oligonucleotide primer having a sequence identical to any one of SEQ ID NO: 114–SEQ ID NO: 316 or a fragment thereof.

In yet another embodiment, the present invention may comprise a method to identify a microbe comprising the ability to modify, or adjust to, an ecosystem. The method may comprise the step of identifying a bioindicator that is associated with a particular microbe. Also, the method may comprise the steps of identifying the bioindicator in at least one ecosystem, and correlating the presence of the microbe with a parameter specific to the ecosystem. Also, the method may comprise identifying the nature of the ability of the microbe to modify, or adjust to, the ecosystem.

There may be certain advantages that may be realized with various embodiments of the present invention. By using a microarray comprising nucleic acid sequences that are specific to microbial operational taxonomic units, the array may cover a wide variety of microbial taxa. Thus, the array may provide a single test that provides substantially comprehensive information on community structure.

The array may, in certain embodiments, provide quantitative data. For example, by using quantifiable labels to label individual samples, or to differentially label specific sequences in a single sample, the array may provide information on the abundance of specific organisms of interest, such as key bioindicators, pathogens, or microbial contaminants in a water system.

Also, the array, if applied to a number of samples over time, may be able to indicate the "trajectory" of the system as either improving or degrading, where probes associated with the quality of the ecosystem of interest are known.

Microorganisms generally respond rapidly to environmental changes. The microarrays of the present invention may therefore provide results in near "real-time" (i.e., within hours) of an event, such as a contamination, occurring. Thus, the array may detect changes in ecosystem perturbations early, so that potential problems may be quickly rectified.

There may be a large number of microorganisms specific to any one ecosystem of interest, such as a specific body of water. Also, the prevalence of particular microorganisms may vary depending upon the water source. Still, by prudent selection of the nucleic acid sequences used as part of an array, the array may be diagnostic of a plurality of microorganisms that are specific to many types of ecosystems. Thus, once developed, the array can be a highly cost-effective way to monitor a variety of ecosystems. Also, the microarray platform may be easily modified and expanded to include new targets of interest as they are identified.

A microbial community may be affected by biological changes, physical changes, or chemical changes to the environment. Because the microarrays of the present invention provide a measure of the microbial community, the array may be sensitive to a wide variety of changes that may occur in the ecosystem of interest.

The present invention may be better understood by reference to the description and figures that follow. It is to be understood that the invention is not limited in its application to the specific details as set forth in the following description and figures. The invention is capable of other embodiments and of being practiced or carried out in various ways.

BRIEF DESCRIPTION OF THE FIGURES

The present invention may be better understood by reference to the following figures. The patent or application file contains at least one drawing executed in color. Copies of this patent or patent application publication with color drawing(s) will be provided by the Office upon request and payment of the necessary fee.

FIG. 3 shows rank-abundance curves for 18S rDNA libraries from three different lakes (Lake Townsend, NC; City Lake, NC; and Lake Toolik, AK) in accordance with an embodiment of the present invention. The curves on left-hand side represent Lake Townsend samples taken from different stations (Station 1 or Station 2) or at different times of the year (March or June). The median for each distribution partitions the operational taxonomic units (OTUs) into two groups shown in black and white; a stippled pattern is used for a median that falls within an OTU.

FIG. 10 illustrates the sequences from prokaryotic rDNA (Panels A-1 and A-2), eukaryotic rDNA (Panels B-1 and B-2), prokaryotic variable regions (Panels C-1 and C-2), and prokaryotic variable regions (Panels D-1 and D-2), in accordance with an embodiment of the present invention.

FIG. 11 shows a schematic diagram of amplification and labeling of two DNA samples for array analysis with universal primers for 16S rDNA or 18S rDNA (Panel A); and results of one hybridization experiment (Panel B), where the eukaryotic and prokaryotic PCR products are detected on the microarray, in accordance with an embodiment of the present invention.

DETAILED DESCRIPTION

Figure 1:
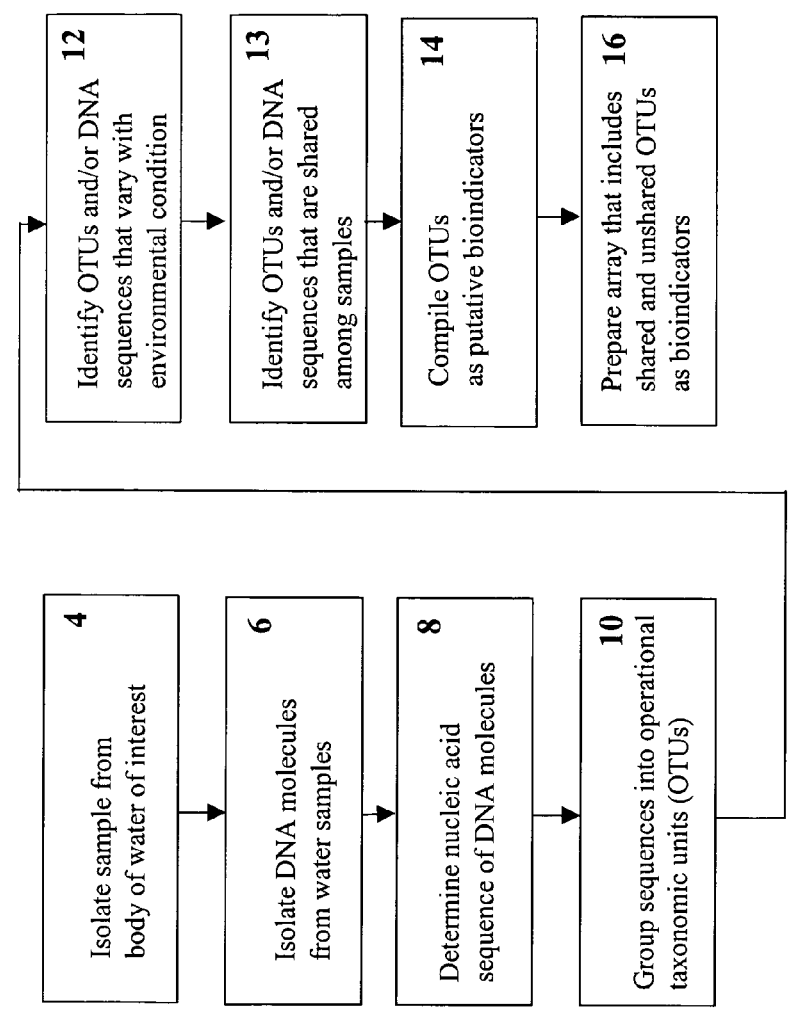
FIG. 1 shows a method for identification of a bioindicator in accordance with an example embodiment of the present invention.

Ecogenomics is the recovery, characterization, and analysis of genomes recovered from organisms living in the natural environment. The present invention utilizes ecogenomics to develop nucleic acid based arrays for monitoring water supplies and other ecosystems.

Thus, the present invention provides methods, systems, and devices to monitor ecosystems. The methods, systems, and devices of the present invention may be used to monitor water. Embodiments of the present invention comprise bioindicators, and methods for isolating a bioindicator for the analysis of an ecosystem of interest. In one embodiment, the present invention comprises a method for developing bioindicators for monitoring water. The bioindicator may comprise a biological system, such as a microorganism, or a molecule, such as a nucleic acid sequence, that changes in response to a parameter that is related to the ecosystem of interest. The bioindicators may comprise known microorganisms or unknown microorganisms. Rather than measuring the microorganism itself, the present invention provides molecular bioindicators to monitor ecosystems of interest.

A bioindicator for the analysis of an ecosystem of interest may comprise an isolated nucleic acid having a sequence derived from a single predetermined microbial operational taxonomic unit (OTU). In one embodiment, the present invention may comprise a method for preparing a bioindicator for the analysis of a biosystem of interest comprising the steps of: preparing a nucleic acid sample comprising a plurality of DNA molecules from an ecosystem of interest; determining the sequence of at least some of the plurality of DNA molecules in the isolated DNA sample; grouping the DNA sequences into operational taxonomic units (OTUs); and identifying at least one nucleic acid sequence that is specific to a single OTU.

DNA from a variety of ecosystems may be used to develop bioindicators. In one embodiment, the ecosystem may comprise a body of water. For example, water from freshwater lakes may be used. Additionally or alternatively, water from estuaries may be used. Additionally or alternatively, water from other types of biosystems, such as tidal pools, wetlands, streams, rivers, and salt water may be used.

The method may utilize bioindicators that are shared among biosystems, and/or bioindicators that are specific to one, or a few, biosystems. Thus, a plurality of bioindicators may be developed. The bioindicators may be used as a means to analyze biosystems of interest. In one embodiment, the method may comprise the step of identifying the distribution of at least one of the OTUs in at least two ecosystems of interest.

Once the DNA molecules have been categorized and grouped by OTU, the sequences of the DNA molecules in each of the OTUs may be used to develop the collection of bioindicators as an assay system. Thus, the method may comprise preparing a collection of bioindicators wherein at least one of the OTUs comprises sequences that are unshared between at least two of the ecosystems of interest. Additionally and alternatively, the method may comprise preparing a collection of bioindicators wherein at least one of the OTUs comprises sequences that are shared between at least two of the ecosystems of interest.

The method may also include a step of immobilizing a plurality of oligonucleotide bioindicators at known locations on a substrate to form an array, wherein each oligonucleotide has a sequence that is derived from a single, predetermined microbial operational taxonomic unit (OTU). In one embodiment, at least one of the OTUs comprises sequences that are shared between at least two of the ecosystems of interest. Alternatively or additionally, at least one of the OTUs may comprise sequences that are unshared between at least two of the ecosystems of interest.

The oligonucleotides immobilized on the array should be of sufficient length to provide specific hybridization to nucleic acid molecules isolated from various water samples that are used to probe the array. The immobilized oligonucleotides may be at least 20 nucleotides in length. In alternate embodiments, the immobilized oligonucleotides may range from about 30 to 200, or from 40 to 100 nucleotides in length. In one example embodiment, the immobilized oligonucleotides are each about 50 nucleotides in length. Specific hybridization does not require a perfect match between the oligonucleotide immobilized on the array and the ecosystem sample used to probe the array. As used herein, specific hybridization comprises hybridization such that a nucleic acid molecule isolated from the ecosystem of interest hybridizes to a single location (i.e., a single oligonucleotide sequence) on the array. As is known in the art, specific hybridization does not require that the immobilized oligonucleotide and the DNA sequence from the sample comprise perfect complementarity, but may allow for a mismatch at one or several base pairs. The level of mismatch will be determined at least in part by the sequence and length of the oligonucleotide immobilized on the array, as well as the hybridization conditions.

Also, the amount of the oligonucleotide immobilized on the array should be sufficient to allow detection of complementary nucleic acid sequences by the array, but in an amount such that background hybridization to unrelated sequences is avoided. In alternate embodiments, the oligonucleotides immobilized on the array range from about 1 fg to about 10 µg, or from about 50 fg to about 10 ng, or from about 0.5 pg to 1,000 pg, or from about 2 pg to 200 pg, or from about 8 pg to about 50 pg, at each location.

The operational taxonomic units may utilize variable ribosomal DNA (rDNA) sequences as a means to detect specific organisms. Thus, the immobilized oligonucleotides may comprise eukaryotic ribosomal DNA sequences, and/or prokaryotic ribosomal DNA sequences. Additionally, or alternatively, the immobilized oligonucleotides may comprise pathogen-specific sequences. Additionally, or alternatively, the immobilized oligonucleotides may comprise novel sequences from as yet unidentified microbes.

The oligonucleotides immobilized on the array may be derived from sequences found by analysis of microbes present in various sources of water. In one embodiment, oligonucleotides having sequences specific to organisms found in freshwater lakes may be used. Additionally or alternatively, oligonucleotides having sequences specific to organisms found in estuaries may be used. Additionally or alternatively, oligonucleotides having sequences specific to organisms found in other types of water systems, such as tidal pools, wetlands, streams, rivers, and salt water may be used.

In one embodiment, at least one immobilized oligonucleotide comprises a sequence identical to any one of SEQ ID NO: 5–SEQ ID NO: 113 or a fragment thereof, or the complement of SEQ ID NO: 5–SEQ ID NO: 113 or a fragment thereof. In alternative embodiments, the array may comprise at least 10 immobilized oligonucleotides that individually comprises a sequence identical to any one of SEQ ID NO: 5–SEQ ID NO: 113 or a fragment thereof, or the complement of SEQ ID NO: 5–SEQ. SEQ ID NO: 113 or a fragment thereof, or at least 20 immobilized oligonucleotides that individually comprises a sequence identical to any one of SEQ ID NO: 5–SEQ ID NO: 113 or a fragment thereof, or the complement of SEQ ID NO: 5–SEQ ID NO: 113 or a fragment thereof, or at least 50 immobilized oligonucleotides that individually comprises a sequence identical to any one of SEQ ID NO: 5–SEQ ID NO: 113 or a fragment thereof, or the complement of SEQ ID NO: 5–SEQ ID NO: 113 or a fragment thereof, or at least 100 immobilized oligonucleotides that individually comprises a sequence identical to any one of SEQ ID NO: 5–SEQ ID NO: 113 or a fragment thereof, or the complement of SEQ ID NO: 5–SEQ ID NO: 113 or a fragment thereof.

The bioindicators may be used to probe an array comprising nucleic acid sequences that are specific to organisms of interest. In one embodiment, the bioindicator may be evaluated to determine how the presence and/or absence of the bioindicator may correlate with a parameter of the ecosystem. Thus, the method may comprise using the polymerase chain reaction (PCR) to amplify a DNA sequence comprising a predetermined OTU. In one embodiment, at least one of the PCR primers comprises a sequence identical to any one of SEQ ID NO: 114–SEQ ID NO: 316 or a fragment thereof. For example, the bioindicator may be used to probe an array comprising a plurality of oligonucleotides immobilized at known locations on a substrate, and wherein each location on the array comprises an oligonucleotide having a sequence that is derived from a single, predetermined microbial operational taxonomic unit (OTU) so as to correlate the pattern of hybridization with a parameter that comprises at least part of the ecosystem. In an embodiment, the parameter comprises water quality.

Also, the method may use a first bioindicator from a particular microbe as an "entry point" for isolating other bioindicators from the microbe. Thus, in one embodiment, a bioindicator isolated from a portion of the genome of a microbe is used to identify a second bioindicator nucleic acid sequence from the same microbe. For example, the sequence of a first bioindicator nucleic acid molecule may be used to identify and isolate contiguous DNA sequence from the microbe that can serve as a bioindicator.

Embodiments of the present invention also comprise bioindicators isolated using the methods and systems of the present invention. In one embodiment, the present invention comprises a bioindicator, or a collection of bioindicators, for the analysis of an ecosystem of interest, wherein a bioindicator comprises an isolated nucleic acid having a sequence derived from a single predetermined microbial operational taxonomic unit (OTU). The bioindicator may comprise a sequence identical to any one of SEQ ID NO: 5–SEQ ID NO: 113 or a fragment thereof, or the complement of SEQ ID NO: 5–SEQ ID NO: 113 or a fragment thereof. Or, in alternate embodiments, the collection of bioindicators may comprise at least 2, or 5, or 10, or 20, or 40, or 50 distinct nucleic acid sequences that individually comprise a sequence identical to SEQ ID NO: 5–SEQ ID NO: 113 or a fragment thereof, or the complement of SEQ ID NO: 5–SEQ ID NO: 113 or a fragment thereof.

The present invention also comprises methods to monitor ecosystems. For example, one embodiment of the present invention may comprise a method for monitoring the water quality in a water sample of interest comprising measuring the hybridization of a nucleic acid sample from a water sample of interest to a plurality of oligonucleotides, and assessing at least one parameter of water quality based upon hybridization of the nucleic acid sample to the plurality of oligonucleotides. In one embodiment, an array of oligonucleotides is used. Thus, the plurality of oligonucleotides may be immobilized at known locations on a substrate, such that each location on the array comprises an oligonucleotide.

In one embodiment, the method may comprise the steps of: generating an array comprising a plurality of oligonucleotides immobilized at known locations on a substrate, wherein each location on the array comprises an oligonucleotide having a sequence derived from a single, predetermined microbial operational taxonomic unit (OTU); preparing a nucleic acid sample from the ecosystem of interest; hybridizing the nucleic acid sample to the array; measuring hybridization of the nucleic acid sample to the array; and correlating hybridization of the nucleic acid sample to the array with a parameter that comprises at least part of the ecosystem.

In one embodiment, the ecosystem may comprise a body of water. For example, water from freshwater lakes may be used. Additionally or alternatively, water from estuaries may be used. Additionally or alternatively, water from other types of biosystems, such as tidal pools, wetlands, streams, rivers, and salt water may be used.

Where the ecosystem of interest comprises water, the parameter comprising at least part of the ecosystem may relate to the quality of the water. Thus, the parameter may relate to a quality that is important to evaluate if the water is suitable for drinking, cooking, bathing, agriculture, or other uses of water.

In one approach, the oligonucleotides are each selected to comprise different taxonomic units. Or, the oligonucleotides may be selected such that at least some are from the same microbial operational taxonomic unit (OTU).

The oligonucleotides immobilized on the array should be of sufficient length to provide specific hybridization to nucleic acid molecules isolated from various ecosystem samples that are used to probe the array. The immobilized oligonucleotides may be at least 20 nucleotides in length. In alternate embodiments, the immobilized oligonucleotides may range from about 30 to 200, or from 40 to 100 nucleotides in length. In one example embodiment, the immobilized oligonucleotides are each about 50 nucleotides in length.

Also, the amount of the oligonucleotide immobilized on the array should be sufficient to allow detection of complementary nucleic acid sequences by the array, but in an amount such that background hybridization to unrelated sequences is avoided. In alternate embodiments, the oligonucleotides immobilized on the array range from about 1 fg to about 10 µg, or from about 50 fg to about 10 ng, or from about 0.5 pg to 1,000 pg, or from about 2 pg to 200 pg, or from about 8 pg to about 50 pg, at each location.

The operational taxonomic units may utilize variable ribosomal DNA (rDNA) sequences as a means to detect specific organisms. Thus, the immobilized oligonucleotides may comprise eukaryotic ribosomal DNA sequences, and/or prokaryotic ribosomal DNA sequences. Additionally, or alternatively, the immobilized oligonucleotides may comprise pathogen-specific sequences. Additionally, or alternatively, the immobilized oligonucleotides may comprise novel sequences from as yet unidentified microbes.

The oligonucleotides immobilized on the array may be derived from sequences found by analysis of microbes present in various ecosystems of interest. In one embodiment, oligonucleotides having sequences specific to organisms found in freshwater lakes may be used. Additionally or alternatively, oligonucleotides having sequences specific to organisms found in estuaries may be used. Additionally or alternatively, oligonucleotides having sequences specific to organisms found in other types of water systems, such as tidal pools, wetlands, streams, rivers and salt water may be used.

In one embodiment, at least one immobilized oligonucleotide comprises a sequence identical to any one of SEQ ID NO: 5–SEQ ID NO: 113 or a fragment thereof, or the complement of SEQ ID NO: 5–SEQ ID NO: 113 or a fragment thereof. In alternative embodiments, the array may comprise at least 10 immobilized oligonucleotides that individually comprises a sequence identical to any one of SEQ ID NO: 5–SEQ ID NO: 113 or a fragment thereof, or the complement of SEQ ID NO: 5–SEQ ID NO: 113 or a fragment thereof, or at least 20 immobilized oligonucleotides that individually comprises a sequence identical to any one of SEQ ID NO: 5–SEQ ID NO: 113 or a fragment thereof, or the complement of SEQ ID NO: 5–SEQ ID NO: 113 or a fragment thereof, or at least 50 immobilized oligonucleotides that individually comprises a sequence identical to any one of SEQ ID NO: 5–SEQ ID NO: 113 or a fragment thereof, or the complement of SEQ ID NO: 5–SEQ ID NO: 113 or a fragment thereof, or at least 100 immobilized oligonucleotides that individually comprises a sequence identical to any one of SEQ ID NO: 5–SEQ ID NO: 113 or a fragment thereof, or the complement of SEQ ID NO: 5–SEQ ID NO: 113 or a fragment thereof.

The array may be hybridized with a nucleic acid sample comprising at least one bioindicator that is isolated from the sample of interest. For example, PCR may be used to amplify rDNA sequences from genomic DNA from a water sample of interest, and the array used to probe those sequences. Alternatively or additionally, PCR may be used to amplify known pathogen-specific sequences from a water sample of interest, and the array used to probe those sequences. Alternatively and additionally, PCR may be used to amplify unidentified (i.e., novel) sequences specific to a water sample of interest, and the array used to probe those sequences. Alternatively or additionally, PCR may be used to amplify known non-pathogen specific sequences specific to a water sample of interest, and the array used to probe those sequences.

The bioindicator isolated from the ecosystem of interest may comprise nucleic acid sequences isolated from rDNA. In one embodiment, the nucleic acid sample hybridized to the array sequence comprises a plurality of rDNA sequences. For example, the nucleic acid sequence hybridized to the array may be generated using PCR primers derived at least in part from a ribosomal variable region so as to specifically amplify rDNA sequences. For example, the primers may comprise at least one oligonucleotide molecule having a sequence identical to any one of SEQ ID NO: 114–SEQ ID NO: 316 or a fragment thereof. In separate and alternative embodiments, the primers used for amplification of DNA from a sample of interest may comprise at least 10 oligonucleotide molecules having a sequence identical to any one of SEQ ID NO: 114–SEQ ID NO: 316 or a fragment thereof, or at least 20 oligonucleotide molecules having a sequence identical to any one of SEQ ID NO: 114–SEQ ID NO: 316 or a fragment thereof, or at least 40 oligonucleotide molecules having a sequence identical to any one of SEQ ID NO: 114–SEQ ID NO: 316 or a fragment thereof. In one example embodiment, the primers used for amplification of a sample of interest include about 50 oligonucleotide molecules having a sequence identical to any one of SEQ ID NO: 114–SEQ ID NO: 316 or a fragment thereof.

By measuring hybridization of the array to a sample from an ecosystem of interest, changes in at least one parameter that are indicative of a change in the ecosystem may be measured. Thus, in one embodiment, the present invention comprises a method for analyzing a pattern to evaluate the status of a biosystem comprising the step of measuring hybridization of a nucleic acid sample to an array of oligonucleotides immobilized at known locations on a substrate, wherein each location on the array comprises an oligonucleotide having a sequence that is derived from a single, predetermined microbial operational taxonomic unit (OTU), and correlating the hybridization of the nucleic acid to the array with a parameter that comprises at least part of the ecosystem. In one embodiment, a single change in the pattern of hybridization to the array for a first nucleic acid sample isolated from an ecosystem of interest as compared to a second nucleic acid sample isolated from an ecosystem of interest is associated with a change in one parameter. Or, a single change in the pattern of hybridization to the array for a first nucleic acid sample isolated from an ecosystem of interest as compared to a second nucleic acid sample isolated from an ecosystem of interest may be associated with a change in a plurality of parameters. Additionally or alternatively, a plurality of changes in the pattern of hybridization to the array of a first nucleic acid sample isolated from an ecosystem of interest as compared to a second nucleic acid sample isolated from an ecosystem of interest is associated with a change in one parameter. Or, a plurality of changes in the pattern of hybridization to the array of a first nucleic acid sample isolated from an ecosystem of interest as compared to a second nucleic acid sample isolated from an ecosystem of interest may be associated with a change in a plurality of parameters. In one embodiment, the pattern analysis may comprise a computer program including known patterns such that samples may be analyzed using a computer. Samples may vary by location of the ecosystem, the time of sampling of a single ecosystem, or the location of sampling within a single ecosystem.

Embodiments of the present invention also comprise arrays of oligonucleotides for monitoring an ecosystem of interest. For example, one embodiment of the present invention comprises a device comprising an array comprising a plurality of oligonucleotides immobilized at known locations on a substrate, such that each location on the array comprises an oligonucleotide having a sequence that is derived from a single, predetermined microbial operational taxonomic unit (OTU).

For example, in an embodiment the present invention comprises a device for monitoring water quality comprising an array, wherein the array comprises a plurality of oligonucleotides immobilized at known locations on a substrate, and wherein each location on the array comprises an oligonucleotide having a sequence that is derived from a single, predetermined microbial operational taxonomic unit (OTU).

Also included as part of the present invention are systems for monitoring ecosystems of interest. Thus, another embodiment of the present invention comprises a system for monitoring an ecosystem of interest comprising an array comprising a plurality oligonucleotides immobilized at known locations on a substrate, such that each location on the array comprises an oligonucleotide having a sequence that is derived from a single predetermined microbial operational taxonomic unit (OTU), and a device able to measure hybridization of the nucleic acid sample to the array. The system may further include a DNA sample comprising a plurality of nucleic acid sequences derived from an ecosystem sample of interest.

In one embodiment, the ecosystem analyzed using the devices and or systems of the present invention may comprise a body of water. For example, water from freshwater lakes may be used. Additionally or alternatively, water from estuaries may be used. Additionally or alternatively, water from other types of biosystems, such as tidal pools, wetlands, streams, rivers and salt water may be used.

The oligonucleotides immobilized on the array should be of sufficient length to provide specific hybridization to nucleic acid molecules isolated from various water samples that are used to probe the array. The immobilized oligonucleotides may be at least 20 nucleotides in length. In alternate embodiments, the immobilized oligonucleotides may range from about 30 to 200, or from 40 to 100 nucleotides in length. In one example embodiment, the immobilized oligonucleotides are each about 50 nucleotides in length.

Also, the amount of the oligonucleotide immobilized on the array of the devices and/or systems of the present invention should be sufficient to allow detection of complementary nucleic acid sequences by the array, but in an amount such that background hybridization to unrelated sequences is avoided. In alternate embodiments, the oligonucleotides immobilized on the array range from about 1 fg to about 10 μg, or from about 50 fg to about 10 ng, or from about 0.5 pg to 1,000 pg, or from about 2 pg to 200 pg, or from about 8 pg to about 50 pg, at each location.

The operational taxonomic units may utilize variable ribosomal DNA (rDNA) sequences as a means to detect specific organisms. Thus, the immobilized oligonucleotides may comprise eukaryotic ribosomal DNA sequences, and/or prokaryotic ribosomal DNA sequences. Additionally, or alternatively, the immobilized oligonucleotides may comprise pathogen-specific sequences. Additionally, or alternatively, the immobilized oligonucleotides may comprise novel sequences from as yet unidentified microbes.

The oligonucleotides immobilized on the array of the devices and/or systems of the present invention may be derived from sequences found by analysis of microbes present in various sources of water. In one embodiment, oligonucleotides having sequences specific to organisms found in freshwater lakes may be used. Additionally or alternatively, oligonucleotides having sequences specific to organisms found in estuaries may be used. Additionally or alternatively, oligonucleotides having sequences specific to organisms found in other types of water systems, such as tidal pools, wetlands, streams, rivers, and salt water may be used.

In one embodiment, at least one immobilized oligonucleotide comprises a sequence identical to any one of SEQ ID NO: 5–SEQ ID NO: 113 or a fragment thereof, or the complement of SEQ ID NO: 5–SEQ ID NO: 113 or a fragment thereof. In alternative embodiments, the array may comprise at least 10 immobilized oligonucleotides that individually comprises a sequence identical to any one of SEQ ID NO: 5–SEQ ID NO: 113 or a fragment thereof, or the complement of SEQ ID NO: 5–SEQ ID NO: 113 or a fragment thereof, or at least 20 immobilized oligonucleotides that individually comprises a sequence identical to any one of SEQ ID NO: 5–SEQ ID NO: 113 or a fragment thereof, or the complement of SEQ ID NO: 5–SEQ ID NO: 113 or a fragment thereof, or at least 50 immobilized oligonucleotides that individually comprises a sequence identical to any one of SEQ ID NO: 5–SEQ ID NO: 113 or a fragment thereof, or the complement of SEQ ID NO: 5–SEQ ID NO: 113 or a fragment thereof, or at least 100 immobilized oligonucleotides that individually comprises a sequence identical to any one of SEQ ID NO: 5–SEQ ID NO: 113 or a fragment thereof, or the complement of SEQ ID NO: 5–SEQ ID NO: 113 or a fragment thereof.

The array devices and/or systems of the present invention may be hybridized with a nucleic acid sample that is isolated from the sample of interest. For example, PCR may be used to amplify rDNA sequences from genomic DNA from a water sample of interest, and the array used to probe those sequences. The nucleic acid sequence for hybridizing to the array may be generated using polymerase chain reaction (PCR) primers derived at least in part from at least one of a eukaryotic or prokaryotic ribosomal variable region. In an embodiment at least one of the PCR primers comprises a sequence identical to any one of SEQ ID NO: 114–SEQ ID NO: 316 or a fragment thereof. In alternate embodiments, the PCR primers comprise at least 2, or 5, or 10, or 20, or 40, or 50 primers that individually have a sequence identical to any one of SEQ ID NO: 114–SEQ ID NO: 316 or a fragment thereof. Alternatively or additionally, PCR may be used to amplify known pathogen-specific sequences from a water sample of interest, and the array used to probe those sequences. Alternatively and additionally, PCR may be used to amplify unidentified (i.e., novel) sequences specific to a water sample of interest, and the array used to probe those sequences. Alternatively or additionally, PCR may be used to amplify known non-pathogen specific sequences specific to a water sample of interest, and the array used to probe those sequences.

The present invention also provides methods for isolating samples from an ecosystem of interest that may be analyzed using molecular methods. Thus, in yet another embodiment, the present invention comprises a method to prepare a nucleic acid sample from a biosystem of interest, the nucleic acid sample comprising a plurality of bioindicator DNA sequences, wherein the method comprises amplifying a DNA sample isolated from a biosystem with a plurality of primers that have the ability to specifically amplify nucleic acid sequences comprising bioindicators. In one embodiment, at least some of the primers comprise at least a portion of a variable region of a ribosomal RNA. For example, the primers may comprise at least one oligonucleotide molecule having a sequence identical to any one of SEQ ID NO: 114–SEQ ID NO: 316 or a fragment thereof. In separate and alternative embodiments, the primers used for amplification of DNA from a sample of interest may comprise at least 10 oligonucleotide molecules having a sequence identical to any one of SEQ ID NO: 114–SEQ ID NO: 316, or a fragment thereof, or at least 20 oligonucleotide molecules having a sequence identical to any one of SEQ ID NO: 114–SEQ ID NO: 316 or a fragment thereof, or at least 40 oligonucleotide molecules having a sequence identical to any one of SEQ ID NO: 114–SEQ ID NO: 316, or a fragment thereof. In one example embodiment, the primers used for amplification of a sample of interest include about 50 oligonucleotide molecules having a sequence identical to any one of SEQ ID NO: 114–SEQ ID NO: 316 or a fragment thereof.

The present invention also comprises compositions for isolating samples from an ecosystem of interest that may be analyzed using molecular methods. Thus, in yet another embodiment, the present invention comprises an oligonucleotide having a sequence identical to any one sequence of SEQ ID NO: 114–SEQ ID NO: 316 or a fragment thereof.

The present invention may also comprise a method to identify microbes that are able to modify, or adjust to, an a particular ecosystem. In one embodiment, the method may comprise the steps of: (a) identifying a bioindicator that is associated with a particular microbe; (b) identifying the bioindicator in at least one ecosystem; and (c) correlating the presence of the microbe with a parameter specific to the ecosystem. The method may further comprise identifying the nature of the ability of the microbe to modify, or adjust to, the ecosystem. For example, the identification of a microbe whose presence shows an association with a particular toxin may indicate that the microbe has the ability to modify the toxin and/or modify the effect of the toxin on the environment.

Definitions

As used herein, the following terms shall have the definitions set out below. Also, in accordance with the present invention, conventional molecular biology, microbiology, and recombinant DNA techniques may be used that will be apparent to those skilled in the relevant art. Such techniques are explained fully in the literature (see, e.g., Maniatis, Fritsch & Sambrook, "Molecular Cloning: A Laboratory Manual (1982); "DNA Cloning: A Practical Approach," Volumes I and II (D. N. Glover ed. 1985).

As used herein, "taxonomic unit" is a group of organisms that are considered distinct enough to be treated as a separate unit. A taxonomic unit may comprise a family, genus or species but is not limited as such. Also as used herein, each "operational taxonomic unit (OTU)" comprises a group of one or more microorganisms that are treated as a unit based on a SSU rDNA sequence identity of ≧97.5% among all members of the group.

As used herein, a bioindicator is an organism or part thereof, or a biological process, whose change in numbers, structure, or function points to a change, or a plurality of changes, in the environment. Generally, a bioindicator has a relatively high and easily identifiable sensitivity to selective environmental influences. The changes in the environment may relate to various changes in the ecosystem such as changes in a single chemical or chemical combinations in either absolute abundance or relative abundance to each other, changes in temperature, changes in biological populations, and the like. Any microbe whose relative abundance depends upon a biotic and/or an abiotic aspect(s) of biosystem of interest, or whose appearance is restricted to a subset of biosystems, is a bioindicator. Moreover, a plurality of two or more bioindicators (two or more present or more abundant than in the absence of a condition, two or more absent or less abundant than in the absence of the condition, or combinations of two or more in abundance and/or presence) may together indicate a condition of the ecosystem of interest. A condition of an ecosystem may refer to either a single biotic or abiotic factor or a combination of such factors.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), microbes, viruses, plasmids, and chromosomes.

DNA molecules may be identified by their nucleic acid sequences, which are generally presented in the 5' to 3' direction, wherein 5' and 3' indicate the linkages formed between the 5'-phosphate group of one nucleotide and the 3'-hydroxyl group of the next. As used herein, for a sequence presented in the 5'-3' direction, its complement is the DNA strand which hybridizes to that sequence according to the Watson-Crick base pairing model. Thus, the sequence of the complement is defined by the sequence of the original strand, such that adenine base-pairs with thymine, and cytosine base-pairs with guanine.

The term "gene" means a region of DNA encoding for the mRNA sequence that codes for a given protein/polypeptide along with elements regulating mRNA expression, or a region of DNA encoding for a ribosomal RNA (rRNA) sequence that performs a structural function as a subunit of ribosomes along with elements regulating rRNA expression.

"Messenger RNA" or "mRNA" shall mean a RNA molecule that encodes for a polypeptide. "Ribosomal RNA" or "rRNA" shall mean a RNA molecule that performs a structural function in ribosomes.

"Complementary DNA" or "cDNA" shall mean the DNA molecule synthesized by polymerization of deoxyribonucleotides from an RNA template by an enzyme with reverse transcriptase activity.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as an oligonucleotide, a genomic fragment, a fragment produced by polymerase chain reaction (PCR), or a restriction fragment; and (d) a recombinant nucleotide sequence that is part of a hybrid gene, i.e., a gene encoding a fusion protein.

"Oligonucleotide", as used herein, is defined as a molecule comprised of two or more deoxy- or ribonucleotides, preferably more than eight. Its exact size will depend upon many factors which, in turn, depend upon the ultimate function and use of the oligonucleotide. As is known in the art, it is possible that each of the olignucleotide molecules may vary by a few bases. For example, the synthesis of the oligonucleotide may result in a portion of the oligonucleotides being less than full length. Or, a portion of the oligonucleotides immobilized at a particular location may degrade by a small percentage over time. Such oligonucleotides are considered to be "fragments" of the original oligonucleotide. Thus, an oligonucleotide sequence that is derived from, and specific to, a single, individual OTU may include fragments of that oligonucleotide.

A "DNA fragment" includes polynucleotides and/or oligonucleotides and refers to a plurality of joined nucleotide units formed from naturally-occurring bases and cyclofuranosyl groups joined by native phosphodiester bonds. This term effectively refers to naturally-occurring species or synthetic species formed from naturally-occurring subunits. "DNA fragment" also refers to purine and pyrimidine groups and moieties which function similarly but which have non naturally-occurring portions. Thus, DNA fragments may have altered sugar moieties or inter-sugar linkages. Exemplary among these are the phosphorothioate and other sulfur containing species. They may also contain altered base units or other modifications, provided that biological activity is retained. DNA fragments may also include species that include at least some modified base forms. Thus, purines and pyrimidines other than those normally found in nature may be so employed. Similarly, modifications on the cyclofuranose portions of the nucleotide subunits may also occur as long as biological function is not eliminated by such modifications.

The term "identical" refers to sequence identity between two amino acid sequences or between two nucleic acid sequences. Percent identity can be determined by aligning two sequences and refers to the number of identical residues (i.e., amino acid or nucleotide) at positions shared by the compared sequences. Sequence alignment and comparison may be conducted using the algorithms standard in the art (e.g. Smith and Waterman, *Adv. Appl. Math.* 2:482 (1981); Needleman and Wunsch, *J. Mol. Biol.* 48:443 (1970); Pearson and Lipman, *Proc. Natl. Acad. Sci. (USA)*, 85:2444 (1988)) or by computerized versions of these algorithms (Wisconsin Genetics Software Package Release 7.0, Genetics Computer Group, 575 Science Drive, Madison, Wis.) publicly available as BLAST and FASTA. Also, ENTREZ, available through the National Institutes of Health, Bethesda Md., may be used for sequence comparison. In one embodiment, percent identity of two sequences may be determined using GCG with a gap weight of 1, such that each amino acid gap is weighted as if it were a single amino acid or nucleotide mismatch between the two sequences.

"Primer" shall refer to an oligonucleotide, whether occurring naturally or produced synthetically, which is capable of acting as a point of initiation of DNA synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used. For example, for multiplex PCR amplification of genomic DNA, the oligonucleotide primer typically contains 15–30 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

"Probe" shall refer to any oligonucleotide that can be immobilized at individual addresses on the array. Such probes are single-stranded DNA molecules. The act of "probing" as used herein describes the step of hybridizing a nucleic acid sample with a probe having a known sequence, or a plurality of probes having known sequences (i.e., an array), to determine whether any of the sequences in the sample are complementary to the probe sequence(s).

As used herein, the term "hybridization" refers generally to a technique wherein denatured RNA or DNA is combined with complementary nucleic acid sequence that is either free in solution or bound to a solid phase. As recognized by one skilled in the art, complete complementarity between the two nucleic acid sequences is not a pre-requisite for hybridization to occur. Hybridization conditions can be described as ranging from low to high stringency. Hybridization that occurs under high stringency conditions is specific in that a large percentage of complementarity between two nucleotide molecules is required for hybridization to occur under stringent conditions. Hybridization that occurs under low stringency conditions is less specific in that a lower percentage of complementarity between two nucleotide molecules is required for hybridization to occur under stringent conditions. Even under highly stringent conditions, there may not be perfect complementarity between two oligonucleotide molecules that hybyridize. Generally, highly stringent conditions refer to washing hybrids in low salt buffer at high temperatures. Hybridization may be to filter bound DNA using hybridization solutions standard in the art such as 0.5M $NaHPO_4$, 7% sodium dodecyl sulfate (SDS) at 65° C., and washing in 0.25 M $NaHPO_4$, 3.5% SDS followed by washing 0.1×SSC/0.1% SDS at a temperature ranging from room temperature to 68° C. depending on the length of the probe (see e.g. Ausubel, F. M. et al., *Short Protocols in Molecular Biology*, $4^{th}$ Ed., Chapter 2, John Wiley & Sons, N.Y). For example, a high stringency wash comprises washing in 6×SSC/0.05% sodium pyrophosphate at 37° C. for a 14 base oligonucleotide, or at 48° C. for a 17 base oligonucleotide, or at 55° C. for a 20 base oligonucleotide, or at 60° C. for a 25 base oligonucleotide, or at 65° C. for a nucleotide probe about 250 nucleotides in length. Equivalent stringencies may be obtained with other wash solutions by varying the temperature as is known in the art. Nucleic acid probes may be labeled with radionucleotides by end-labeling with, for example, [$\gamma$-$^{32}$P]ATP, or by incorporation of radiolabeled nucleotides such as [$\alpha$-$^{32}$P]dCTP by random primer labeling. Alternatively, probes may be labeled by incorporation of biotinylated or fluorescein labeled nucleotides, and the probe detected using antibodies to the label, or by chemical incorporation of cyanin dyes as described herein.

As used herein, "restriction endonucleases" and "restriction enzymes" shall refer to bacterial enzymes that cleave double-stranded DNA at or near a specific nucleotide sequence.

A polypeptide refers to any peptide generated from a protein or the full-length protein itself. A polypeptide may include the full-length protein or a fragment generated by proteolytic cleavage, chemical cleavage, or other means.

As used herein, an array or microarray is a solid-state grid containing short sequences of nucleic acid (usually DNA) of known sequence fixed at a particular position (i.e., location or address) on the grid. DNA arrays are usually termed microarrays due to the small size of the grid and the small amounts of nucleotide (e.g., μM or nM amounts) present at each address.

As used herein, a computer program comprises a computer-encoded language that encodes the steps required for the computer to perform a specific task or tasks.

Also, as used herein, software comprises the computer program(s) used in conjunction with any other operating systems required for computer function.

As used herein, the singular forms "a", "an" and "the" include plural references unless the context clearly dictates otherwise.

Water Surveillance Using Nucleic Acid Based Arrays

The present invention recognizes that the abundance of certain microorganisms may be affected by local water conditions. These conditions may vary for individual species and strains. For example, whereas one species might proliferate in phosphate-rich water, another species may prefer low-phosphate water (Kilham et al, 1986, *Limnol. Oceanogr.*, 31:1169–1181; Siver et al., 1999, *Limnol. Oceanograph.*, 44:1928–1955). Also, phytoplankton and benthic algae may be used as indicators of eutrophication (Shubert, L. E. (ed.), 1984, *Algae as ecological indicators*. Academic Press, N.Y; Stoermer, E. F. and J. P. Smol, 1999, *The Diatoms: applications for the environmental and earth sciences*, Cambridge Univ. Press, Cambridge, UK). Or, the abundance of known microbial species can vary as a function of pollution levels (Lemke et al., 1997, *Microb. Ecol.*, 34:224–231). It has been shown that the presence of high levels of heavy metals in water may be reflected in the tissue of the marine limpet (Pérez-López, M., et al., 2003, *Journal of Environmental Health, Part A—Toxic/Hazardous Substances and Environmental Engineering*, 38:2845–2856). Also, coliform bacteria may be used as an indicator of the presence of human sewage in aquatic systems.

Over the past decade, direct observation and culturing of microbes has been complemented by emerging molecular approaches, including: in situ hybridization (Schöhuber, W., et al. 1991, *Appl. Environ. Microbiol.* 65:1258–1267), selective PCR detection of individual taxa (e.g. Oldach, D. W., et al. 2000, *Proc. Natl. Acad. Sci. USA*, 97:4303–4308; Rublee, P. A., et al. 2001, *Environ. Health Perspectives*, 109 [Supplement 5]:765–767), community assays such as Differential Gradient Gel Electrophoresis (DGGE) analyses (e.g., Díez, B., et al. 2001, *Appl. Environ. Microbiol.*, 67:2942–2951) and filter macroarray hybridization (e.g., Rudi, K., et al. 2000, *Appl. Environ. Microbiol.*, 66:4004–4011). In situ hybridization allows taxon-specific identification and enumeration of target organisms. Although highly specific, the method is time consuming as it generally involves microscopic observation of the sample. PCR, the polymerase chain reaction, may detect a targeted organism that exists in low abundance in the natural environment. Selective PCR detection of individual microbes is highly specific, rapid, and may even be quantitative (e.g., real-time quantitative PCR), but may be limited in that primers specific to the sequence to be amplified must be available. DGGE analysis has become a relatively common approach to community assessment of prokaryotic or even eukaryotic communities, but is limited in that it relies on the assumption that different nucleic acid sequences will display differential mobility in a gradient gel, which is not always the case.

From the standpoint of environmental investigations, recent microarray development efforts have increasingly focused on the identification of genes from specific microbial organisms associated with environmental processes, such as nitrogen fixation, or with the detection of specific microbes (Wu et al., 2001, *Appl Environ. Microbiol.*, 67:5780–5790). Most of the microbes that exist in freshwater sources, however, are unknown and/or unculturable (Kaeberlein et al., 2002, *Science*, 296:1127–1129; Hiorns et al., 1997, *Appl. Evnviron. Microbiol.*, 63: 2957–2960; Lopez-Garcia et al., 2001, *Nature*, 409:603–607).

A first step of developing methods and systems to monitor water may be the identification of suitable bioindicator molecules. For example, one aspect of developing an array to monitor a water supply is to develop nucleic acid sequences that are diagnostic of the aqueous microbial population. FIG. 1 shows an embodiment of a method of the present invention that may be used to identify potential ecosystem biomarkers. As shown in FIG. 1, the method 2 may comprise a first step of isolating a sample from an ecosystem of interest 4. The ecosystem may comprise a body of water. In alternate embodiments, water from a freshwater lake, an estuary, a tidal pool, wetlands, a stream, river, or salt water may be used.

The bioindicator may comprise the microorganism itself, or a molecule that provides information about the microorganism. The bioindicator may comprise a nucleic acid molecule. Nucleic acid molecules may be useful as bioindicators as nucleic acid molecules comprise a source of qualitative and quantitative information. By analyzing the sequence of the DNA molecules in the water sample, information about the genetic make-up of the microbes present in the sample may be obtained. Also, by measuring the amount of DNA molecules in the water sample, information about the amount of specific microbes in the sample may be obtained. As described herein, nucleic acid molecules, such as DNA, may be used to identify and classify microorganisms into operational taxonomic units (OTUs). Thus, the method may comprise the step of isolating nucleic molecules from the water sample 6.

The method may next comprise the step of determining the sequence of DNA molecules isolated from the sample of interest 8. In an embodiment, rDNA may be used as diagnostic sequences. Thus, to make an array for monitoring water, a first step may comprise the isolation and sequence characterization of 16S rDNA (prokaryotic) and 18S (eukaryotic) rDNA species from selected water reservoir samples. The DNA molecules selected for analysis may comprise small subunit (SSU) ribosomal RNA genes (SSU rDNA). In this way, recovery of DNA sequences may be based on the endogenous abundance of individual microbes, and is not restricted to the recovery of known microorganisms.

The DNA sequences isolated from the ecosystem of interest may be used to generate bioindicator probes. In one embodiment, the bioindicator probes are categorized into operational taxonomic units (OTUs) 10. Both prokaryotic and eukaryotic SSU rDNA can be useful targets for determination of operational taxonomic units because SSU rDNA sequences contain highly conserved nucleotide regions interspersed with variable regions. The conserved sequences provide an anchor by which a plurality of different rDNA sequences may be isolated from a sample. By using primers that hybridize to the conserved regions of either eukaryotic or prokaryotic rRNA genes, a library of amplified rDNA sequences that are different in the variable regions may be isolated from a single sample. Primers that may be used for amplification of prokaryotic rDNA sequences may comprise SEQ ID NOS: 1 and 2 (Table 1). Primers that may be used for amplification of eukaryotic rDNA sequences may comprise SEQ ID NOS: 3 and 4 (Table 1).

TABLE 1

Sequences and target positions of primers used to amplify rRNAs

| Primer | Sequence | SEQ ID NO: | Location |
|---|---|---|---|
| 16S Forward | AGAGTTTGATCCTGGCTCAG[1] | 1 | 8–27[2] |
| 16S Reverse | AAGGAGGTGATCCAGCCGCA[1] | 2 | 1541–1522[2] |

TABLE 1-continued

Sequences and target positions of primers used to amplify rRNAs

| Primer | Sequence | SEQ ID NO: | Location |
|---|---|---|---|
| 18S Forward | AACCTGGTTGATCCTGCCAGT[3] | 3 | 1–21[4] |
| 18S Reverse | TGATCCTTCTGCAGGTTCACCTAC[3] | 4 | 1795–1772[4] |

[1]Primers from Edwards et al., 1989, Nucleic Acids Res., 17, 7843–7853; Bruce et al., 1992, Appl. Environ. Microbiol., 58, 3413–3416.
[2]Position in *E. coli* (Brosius et al., 1981, J. Mol. Biol., 148, 107–127).
[3]Primers from Medlin et al., 1988, Gene 71, 491–499.
[4]Position in *S. cerevisiae* (Rubstov et al., 1980, Nucl. Acids Res., 8, 5779–5794).

The amplified rDNA products may be used to provide a foundation for phylogenetic classification and comparison of both prokaryotic and eukaryotic microbial species isolated from the water samples of interest (see e.g., McCaig, A. E., et al., 1999, Appl. Environ. Microbiol., 65:1721–173036, Reysenbach, A. L., et al., 1992, Appl. Environ. Microbiol., 58:3417–3418; Pace et al., 1986, Adv. Microb. Ecol., 9:1–55; Sogin and Gunderson, 1987, Annals. NY Acad. Sci. 503:125–139). A level of 97.5% sequence identity is a generally accepted criterion by which rDNAs may be placed in the same operational taxonomic unit (OTU). Because multiple small subunit rDNAs may reside within a genome for any single species (Farrelly et al., 1995, Appl. Environ. Microbiol. 61:2798–2801), a 97.5% level of sequence identity generally allows for the possibility that sequences in the same species are recovered. In performing this type of analysis, it may be necessary to check for artifactual sequences resulting from the amplification protocol (e.g., CHIMERA-CHECK; Kopzcysnski et al., 1994, Appl. Environ. Microbiol., 60:746–748; Wang and Wang, 1995, Appl. Environ. Microbiol., 63:4645–4650; Qui et al., 2001, App. Environ. Microbiol., 58: 2717–2722).

Figure 2:
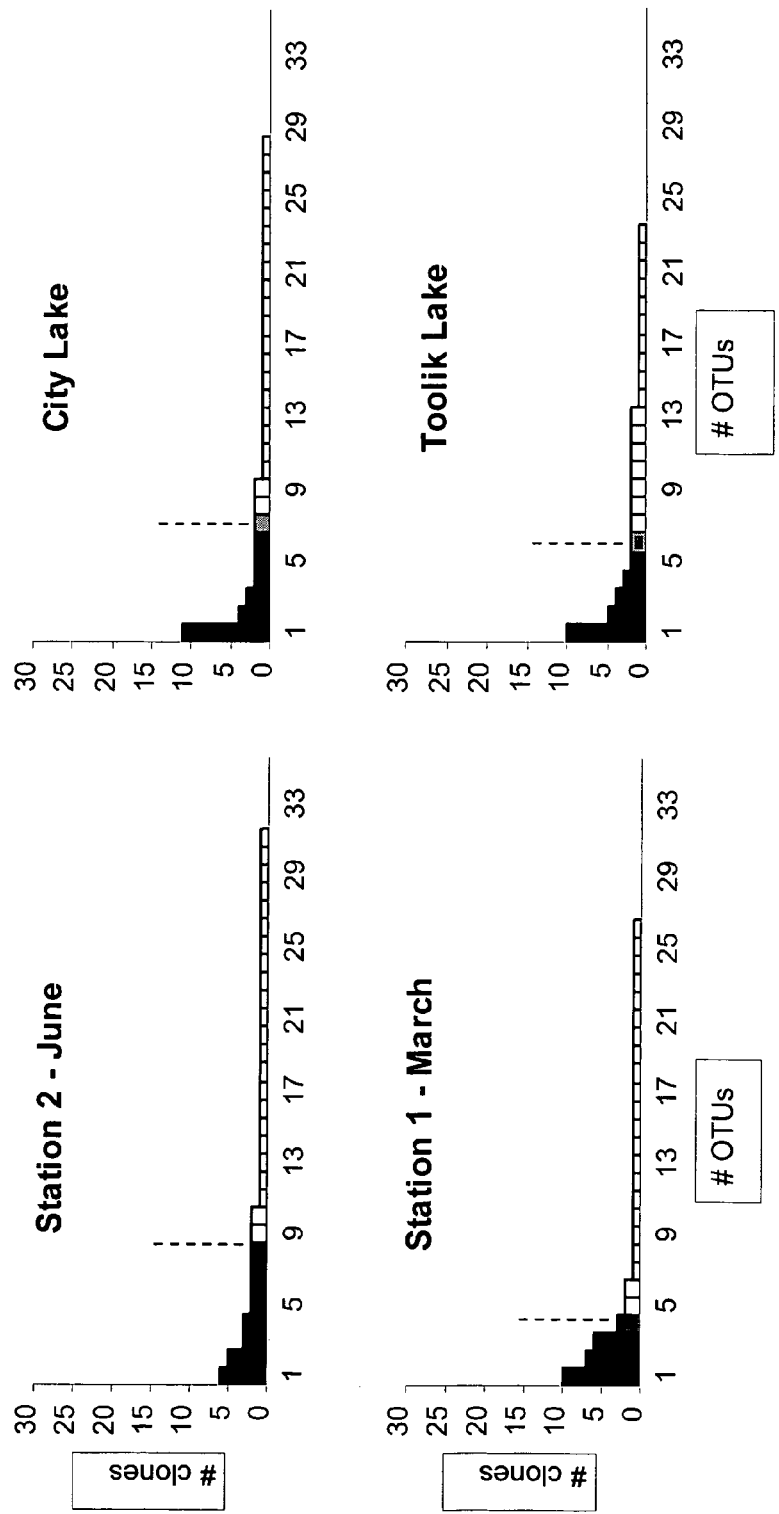
FIG. 2 shows rank-abundance curves for 16S rDNA libraries from three different lakes (Lake Townsend, NC; City Lake, NC; and Lake Toolik, AK) in accordance with an embodiment of the present invention. The curves on left-hand side represent Lake Townsend samples taken from different stations (Station 1 or Station 2) or at different times of the year (March or June). The median for each distribution partitions the operational taxonomic units (OTUs) into two groups shown in black and white; a stippled pattern is used where the median falls within an OTU.

The present invention recognizes that the sequences of small subunit rRNAs in prokaryotes and eukaryotes may allow for phylogenetic classification of known and novel species as operational taxonomic units (OTUs). For example, FIGS. 2 and 3 show rank-abundance curves for 16S rDNA sequences, and 18S sequences, respectively, isolated from five separate samplings from three different lakes that were organized as operational taxonomic units. The water samples were taken from the following lakes: Lake Townsend, NC, Station 1, in June; Lake Townsend, NC, Station 2 in June; Lake Townsend, Station 1, in March; City Lake, NC; and Lake Toolik, AK. It can be seen that some of the OTUs have multiple members (i.e., # clones >1), whereas many of the OTUs were represented by only one sequence. In one embodiment, a sequence from a defined OTU will recognize (i.e., hybridize to) other members of the OTU under the conditions used for hybridization of the array. Thus, in one embodiment, an array may be made using unique OTUs as isolated from the various samples.

Figure 4:
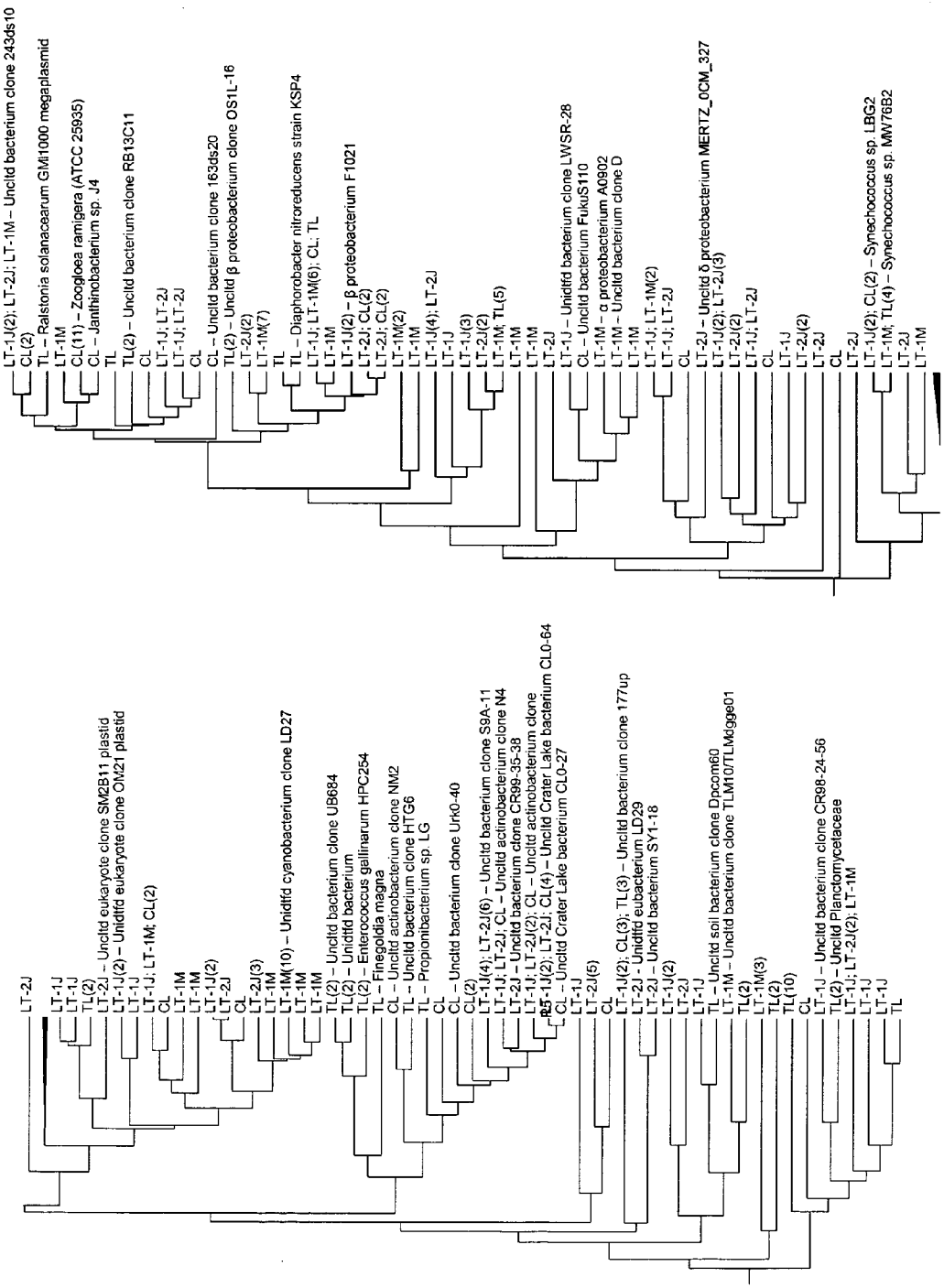
FIG. 4 shows a phylogenetic tree of 16S rDNA operational taxonomic units (OTUs) derived by an Unweighted Pair-Group Method with Arithmetic Mean (UPGMA) analysis using DNA isolated from three different lakes in accordance with an embodiment of the present invention. Numbers in parentheses designate the size of OTUs (i.e., the number of unique sequences per OTU). Identifications by BLAST analysis using the GenBank database are shown. Water samples from which the rDNA was isolated were as follows: LT-1J: Lake Townsend, station 1, June; LT-2J: Lake Townsend, station 2, June; LT-1M: Lake Townsend, station 1, March; CL: City Lake; TL: Toolik Lake.
Figure 5:
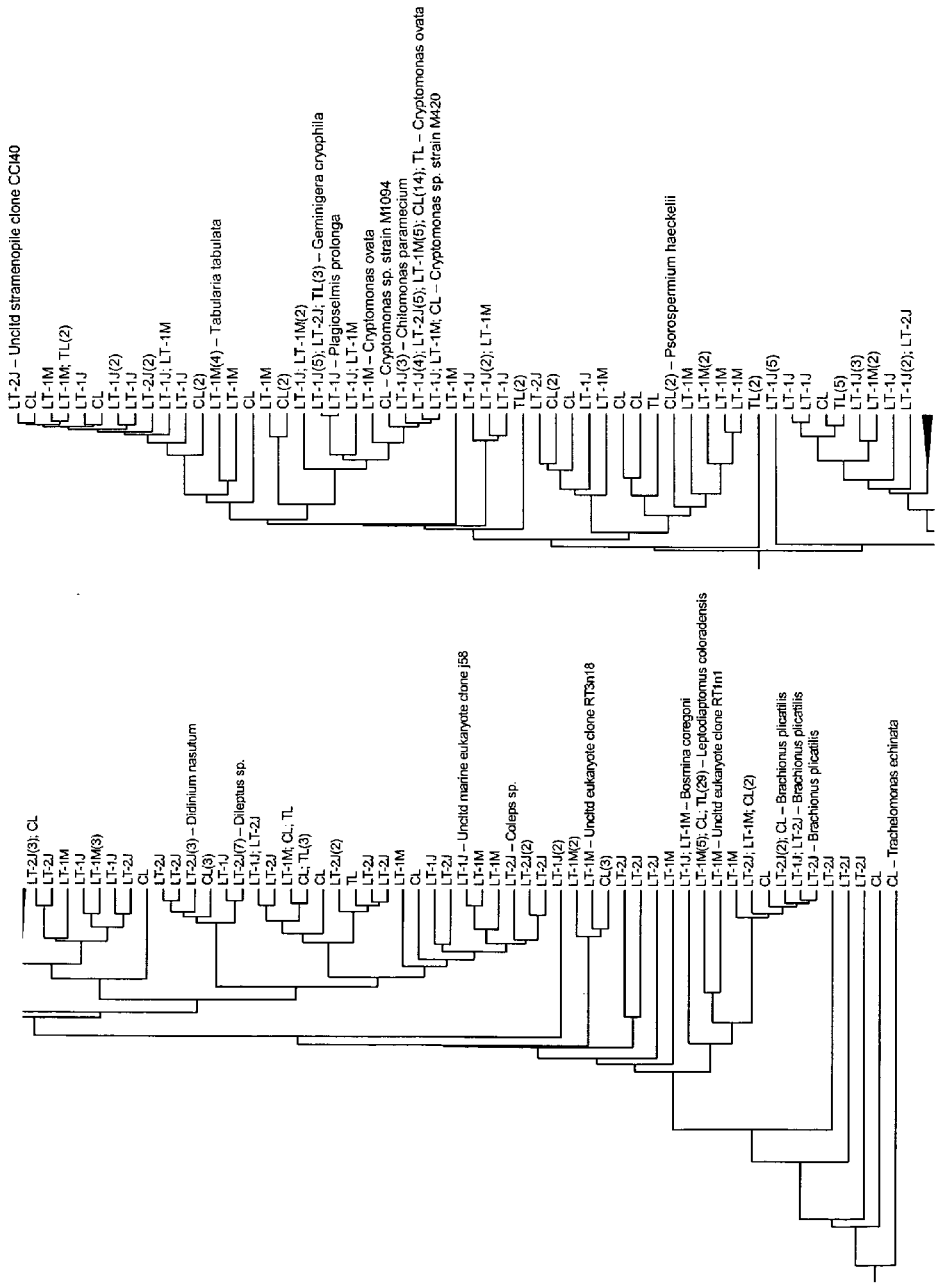
FIG. 5 shows a phylogenetic tree of 18S rDNA operational taxonomic units (OTUs) derived by an Unweighted Pair-Group Method with Arithmetic Mean (UPGMA) analysis using DNA isolated from three different lakes in accordance with an embodiment of the present invention. Numbers in parentheses designate the size of OTUs (i.e., the number of unique sequences per OTU). Identifications by BLAST analysis using the GenBank database are shown. Water samples from which the rDNA was isolated were as follows: LT-1J: Lake Townsend, station 1, June; LT-2J: Lake Townsend, station 2, June; LT-1M: Lake Townsend, station 1, March; CL: City Lake; TL: Toolik Lake.

The sequences of rDNAs from isolated samples may be used to generate phylogenetic trees. In one embodiment, the Unweighted Pair Group Method with Arithmetic Mean (UPGMA) may be used to compare the sequence data from OTUs and to generate a phylogenetic tree. This type of analysis may be used to confirm the relationship between known sequences, and to order newly identified sequences and OTUs. For example, FIG. 4 shows a prokaryote tree constructed using 111 different 16S rDNA OTUs, including 40 OTUs that are based on known rDNA sequences. FIG. 5 shows a eukaryote tree constructed using 109 18S rDNA OTUs, and including 22 known rDNA sequences. In FIGS. 4 and 5, Lake Townsend, NC, samples are denoted LT (1J, Station 1 in June; 2J, Station 2 in June; 1M, Station 1 in March), City Lake, NC samples are denoted CL, and Toolik Lake, AK samples are denoted TL.

The sequence information may also permit the development of species specific primers. Species-specific primers may be used to characterize a variety of prokaryotic and eukaryotic microbes such as cyanobacteria, *Mycobacterium*, *Pfiesteria piscicida*, and other types of microbial species (see e.g., Edwards, U., et al., 1989, *Nucleic Acids Res.*, 17:7843–7853; Reysenbach, A. L., et al., 1992, *Appl. Environ. Microbiol.*, 58:3417–3418; Shi, W., et al., 2002, *Appl. Environ. Microbiol.*, 68:3859–3866; and O'Brien, W. J., et al., 1997, The Limnology of Toolik Lake, p. 61–106, In: Freshwaters of Alaska—ecological syntheses, A. M. Milner and M. W. Oswood (eds), Springer-Verlag Publishers, New York, N.Y.).

Bioindicators may be unique to a specific biosystem, or may be shared among a plurality of biosystems. A diversity of microbial species may be readily retrievable even from a single body of water. Also, while any one body of water may have several unique OTUs, it is highly likely that the sample will include OTUs that are common to other biosystems. Such common OTUs may represent 10% or more of the rDNAs analyzed in the sample, and may be shared across water samples. Also, an environmental event that occurs in an environmental community, such as a contamination, may alter the abundance of individual microbial species and related bioindicators in that community. The method may therefore comprise the step of determining whether an operational taxonomic unit (OTU) and/or an individual or species-specific DNA sequence is specific to a particular ecosystem, or varies in abundance between ecosystems. For example, a bioindicator for assessing freshwater microbial communities may comprise nucleic acid sequences that are characteristic of the freshwater system, or that are diagnostic of the response of microbes to certain changes in the fresh water environment. Or, a bioindicator for assessing marsh water microbial communities may comprise nucleic acid sequences that are characteristic of the marsh environment, or that are diagnostic of the response of microbes found in the marsh environment to certain changes in a marsh water environment. Thus, referring back to FIG. 1, the method may therefore comprise identifying bioindicators or OTUs that vary among ecosystems 12. The method may also comprise identifying bioindicators or OTUs that are shared among ecosystems 13.

To determine which OTUs, if any, appear in more than one ecosystem, the sequences from a library of DNA sequences isolated from a biosystem of interest may be compared to those sequences in every other library from biosystems of interest in pairwise library comparisons, and a similarity coefficient may be calculated for each pairing. For example, in an analysis of five different samplings of DNA molecules from three different lakes (Lake Townsend, NC; City Lake, NC; and Toolik Lake, AK) there was some overlap between every pair of samples. There were also notable differences between the lakes. For example, none of the prokaryotic sequences were shared between Lake Townsend, a mesotrophic lake in North Carolina, and Toolik Lake, an oligotrophic lake in Alaska.

Venn diagrams may be used depict sample comparisons at different spatial and temporal scales to identify sequences that may differ between biosystems. Referring now to FIG.

6, in a fine-scale spatial comparison of samples taken in June from stations 1 and 2 at Lake Townsend, NC (LT-1J and LT-2J), it can be seen that even between samples that may be expected to be highly similar, differences in sequences may be found. For example, for LT-1J and LT-2J, there were two rDNA sequences that occurred four times as often in LT-2J as in LT-1J: an unidentified 16S rDNA OTU, and an 18S rDNA from *Geminigera cryophila* (not shown). Such unequal occurrences of an OTU between samples may signify a detectable difference in the relative abundance of a specific microbial population between samples, and OTUs that consistently vary in frequency among samples are potential bioindicators.

Once the nucleic acid sequences isolated from various ecosystems have been identified and compared, it may be possible to compile OTUs as putative bioindicators 14 (FIG. 1). For example, for five samplings from three different lakes, 26 different eukaryotic OTUs represented by multiple copies, including 11 that are associated with known species, may be identified. Another 79 eukaryotic OTUs may be obtained as single copy clones, with many of the single-copy OTUs representing unidentified species (Marshall, 2002, Masters Thesis, University of North Carolina at Greensboro). Also, 45 different prokaryotic OTUs may be detected in multiple copies. Of these, 10 species are associated with a known species, and 19 species display substantial homology to reported sequences for as yet unidentified species. Another 92 single copy rDNA sequences, most from unidentified prokaryotes, may be recovered (Amos, 2002, Masters Thesis, University of North Carolina at Greensboro). As described in more detail herein, all of the sequences identified from the ecosystems of interest (e.g., water samples), whether derived from known or previously unidentified rDNA sequences, may be used as probes printed on an array of the present invention.

The method may next comprise the step of organizing a nucleic acid array that can reflect microorganisms that are common to multiple communities, as well as organisms that are specific to one or only a few communities to thereby monitor the effect of an ecological change 16. Thus, the ability to assess environmental parameters of water quality may require a sufficient number of bioindicator species that have unique profiles in different ecosystems, but may also require species that are shared among samples to allow for general application.

The array may comprise nucleic acids that are specific to known organisms. Additionally or alternatively, the array may comprise nucleic acids that are grouped to provide information about various taxonomic groups. For example, the array may comprise a plurality of prokaryotic and/or eukaryotic nucleic acid sequences derived from specific rDNAs. Or, the array may comprise a plurality of nucleic acid sequences organized by operational taxonomic unit. Notably, there is no requirement that the environmental DNA samples used to develop the array are the same as the environmental communities to be analyzed.

Samples that are derived from very different environmental communities may be expected to vary more than samples that are derived from similar communities, or the same community. Still, samples taken from a single lake, but either at a different location, or a different season, may also show variation (e.g., FIG. 6). The variation may be qualitative, in that specific OTUs are either absent from, or present in, a water sample. Or, it may be that a certain OTU is much less abundant in one sample than another sample. For example, FIG. 7 illustrates a quantitative PCR determination of the relative amounts of three nucleic acid sequences found in each of three lake samples tested, but in highly varied amounts. For each of the curves shown in FIGS. 7 (7A, 7B, and 7C), the second curve from the left represents the sample from which the nucleic acid of interest was detected in high abundance, and the third and fourth curves from the left represent other lake samples tested. Also, results for a positive control, including each of the test samples, and a negative control with no DNA, are shown. Such skewed amplification curves may be found where DNAs vary in quantity between samples. In alternate embodiments, the template DNAs may vary 10-fold, or 20-fold, or 50-fold, or more than 200-fold, between samples.

Figure 8:
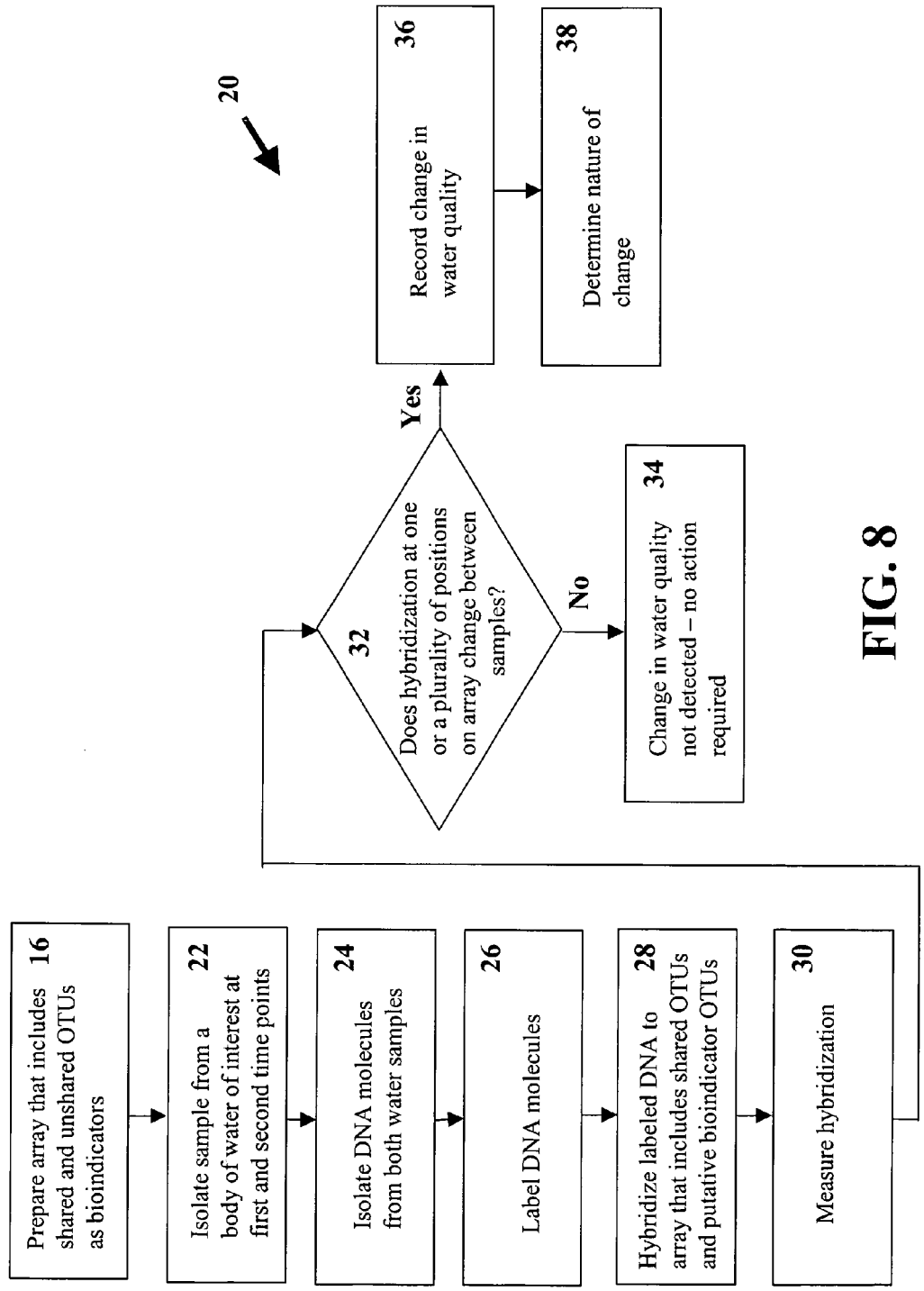
FIG. 8 shows a method for monitoring water in accordance with an example embodiment of the present invention.

FIG. 8 provides a schematic representation of a method that may be used to monitor water in accordance with an embodiment of the present invention. The method may comprise the first step 16 of generating an array comprising a plurality of oligonucleotides immobilized at known locations on a substrate, wherein each location on the array comprises an oligonucleotide having a sequence derived from a single, predetermined microbial operational taxonomic unit (OTU) as is described herein for FIG. 1.

Next, the method may comprise the step of isolating a sample from an ecosystem of interest 22. In one embodiment, the ecosystem may comprise water. Samples may be collected from one body of water at different levels, or at different locations, and/or during different times of the year. Also, samples from different bodies of water may be used. For example, samples may be collected from different lakes, pools, estuaries, or marshes. Or, bodies of water comprising different types of growth levels may be used (e.g., eutrophic, mesotrophic, or oligotrophic). Or, samples may be obtained from a body of water because there is a reason to suspect that the body of water has been contaminated in some way.

The method may next comprise the step of preparing a DNA sample from the ecosystem of interest 24. For example, the polymerase chain reaction (PCR) may be used to amplify DNA sequences from a water sample of interest. The PCR amplification may use primers designed to amplify sequences that, if present in the sample and amplified, are complementary to the sequences on the array. In that way, if a sequence on the array is present in the sample of interest, it may be detected. In one example, a multiplex (i.e., multiple primer) PCR amplification is used to amplify multiple sequences from the sample of interest that are complementary to sequences immobilized on the array. Primer pairs that may be used for multiplex PCR may include a sequence selected from the group of SEQ ID NO: 114–SEQ ID NO: 316.

The amplified DNA molecules from the sample of interest may be then labeled in some manner 26. For example, the amplified DNA molecules may be labeled by the chemical incorporation of a fluorescent dye(s) as described herein.

Next, the method may comprise the step of hybridizing the labeled DNA sample from the ecosystem of interest to the array 28. In one embodiment, a high stringency hybridization is used. For example, the hybridization conditions may comprise the conditions as described herein.

The presence of sequences in the sample of interest that are complementary to putative bioindicator sequences on the array may be determined by measuring locations on the array that exhibit hybridization to the labeled probe 30. In this way, the identity, and in some cases, the relative amounts, of sequences that are in the sample may be determined.

The method may then comprise the step of correlating hybridization of the DNA sample to the array with a parameter that comprises at least part of the ecosystem. For example, if two samples of water (e.g., sample A and sample B) are hybridized to the same array, and different hybridization patterns result, than the oligonucleotide(s) on the array that displays a change in hybridization may correspond to a DNA sequence(s) that is diagnostic of a difference, or a plurality of differences between the two samples. Thus, the method may comprise the step of determining whether the pattern of hybridization at any one position or at a plurality of positions on the array changes 32.

In one embodiment, no change in the pattern of hybridization at any one position or at a plurality of positions on the array is detected upon hybridization with two different samples. In this, case, no change in water quality is detected, and no action is required 34. Alternatively, a change in the pattern of hybridization at any one position or at a plurality of positions on the array is detected upon hybridization with two different samples. In this case the change in the water quality may be recorded 36 and the nature of the change determined 38 such that appropriate action may be taken.

Figure 9:
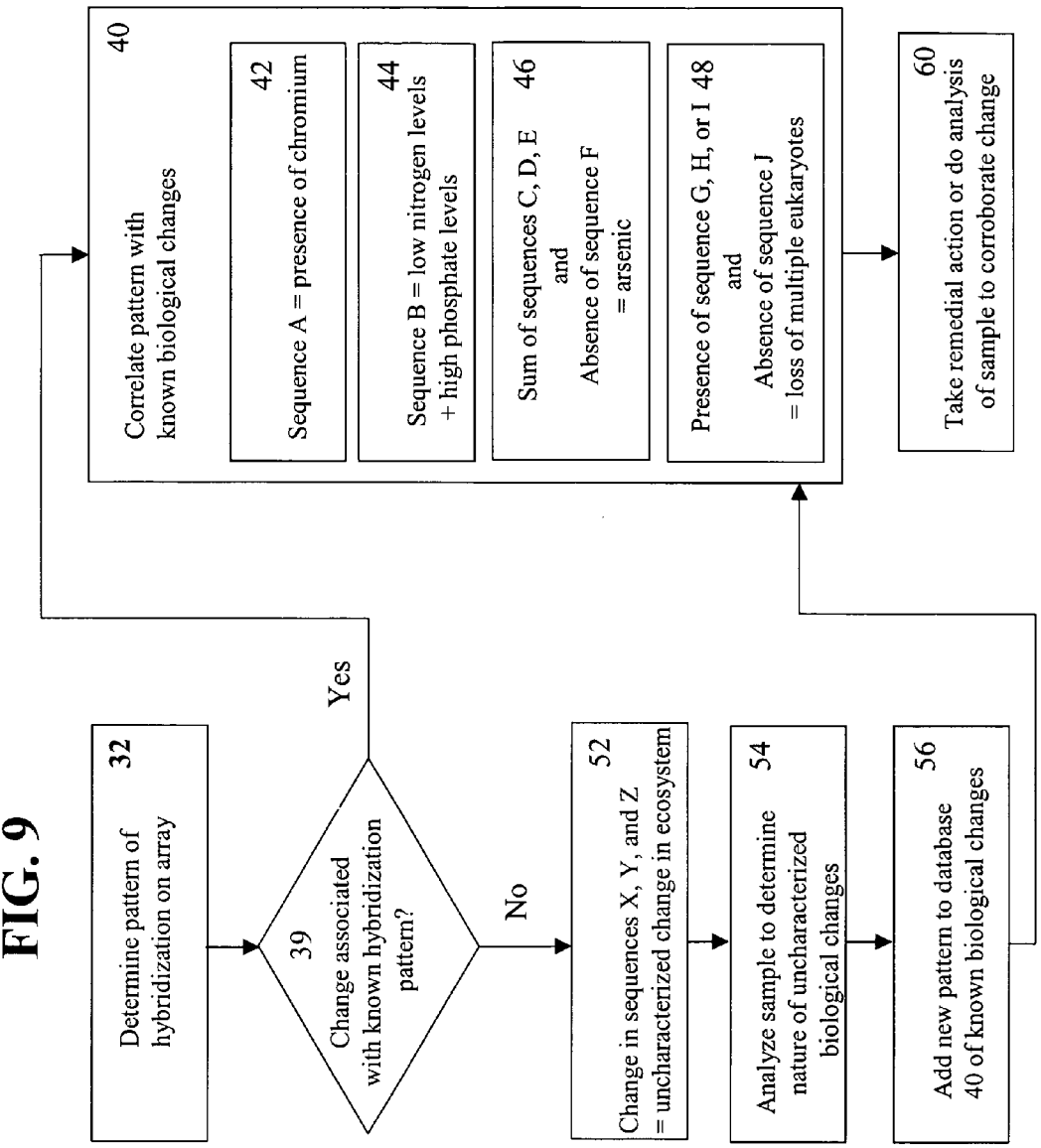
FIG. 9 illustrates the use of pattern analysis for assessing changes in an ecosystem in accordance with an embodiment of the present invention.

An example of the application of pattern analysis to the evaluation of a biosystem is shown in FIG. 9. As a first step, the method may include determining the pattern of hybridization on the array 32. Methods for measuring hybridization may include use of a radiolabeled dNTP during amplification of the sample DNA such that DNA sequences that hybridize to the array may be detected by autoradiography. Alternatively, the amplified PCR products may be labeled with a fluorescent dye and hybridization detected using a fluorometer. Once the pattern of hybridization has been measured and recorded, the pattern may be compared with the pattern of hybridization produced by a separate sample, such that any changes in hybridization may be documented. At this point, a determination may be made as to whether the new hybridization pattern has a change that is associated with a known hybridization pattern 39. If it is determined that the pattern of hybridization is not associated with a known biological change 52, the sample may be analyzed to determine the nature of the change 54. Once the nature of the change is known, the pattern may be added to a database 40 of patterns associated with known biological changes 56.

Still referring to FIG. 9, in some cases, it may be possible to correlate the pattern of hybridization with known a biological change(s) 40. This may be possible even where at least some of the sequences on the array, or the changes in the hybridization pattern, arise from novel, or previously uncharacterized, organisms. For example, there may be a single change in the pattern of hybridization to an array for two samples that is diagnostic of a single change between the two samples. Thus, as shown in FIG. 9, hybridization at the position corresponding to an oligonucleotide having the nucleic acid sequence of A may be associated with the presence of chromium 42. Again, it may not be necessary to identify or characterize the organism from which sequence A is derived as such information may be ascertained merely by prior characterization that sequence A is associated with chromium in a water sample. Alternatively, a single change in the pattern of hybridization to an array for two samples may be diagnostic of a plurality of changes between the two samples. For example, a change in hybridization at sequence B may be associated with a change in the ratio of nitrogen to phosphate in a water sample 44. Or, there may be multiple changes in the pattern of hybridization to an array for two samples that are diagnostic of a single change between the two samples. For example, the presence of hybridization at oligonucleotides having sequences C, D, and E and the absence of hybridization at oligonucleotide corresponding to sequence F may be diagnostic of the introduction of arsenic into the water system 46. In yet another embodiment, there may be multiple changes in the pattern of hybridization to an array for two samples that are diagnostic of multiple changes between the two samples. For example, the presence of hybridization at oligonucleotides corresponding to sequences G, H, and I, in combination with the lack of hybridization at oligonucleotides corresponding to sequence J, may be diagnostic of a loss of multiple eukaryotes from the system. The information provided by the array may be comprehensive and allow for any remedial steps that may be required to be taken. The analysis may be formatted as part of a computer program so as to be run on a computer. In one embodiment, the known patterns may be included as a part of the computer program. Alternatively, the information provided by the array may be considered to provide a preliminary screening which may then be verified by chemical and/or microbiological analysis of the sample 60.

As described herein, primers that may be used for amplification of bioindicator nucleic acid molecules from an ecosystem may be designed to amplify sequences from the variable regions of rDNA. Small subunit rRNA genes (SSU rDNA) are especially useful targets for the molecular identification of microbial species because these sequences contain highly conserved nucleotide regions interspersed with variable regions. The variable regions may be used as a foundation for phylogenetic classification and comparison of both prokaryotic and eukaryotic microbial species (e.g., Sogin and Gunderson, 1987, *Annals. NY Acad. Sci.*, 503: 125–139). The sequence information also permits detection and quantification of microbial species by PCR amplification using species-specific primers.

Thus, in one embodiment, ribosomal DNA that includes highly conserved and highly variable regions is used to characterize the presence of microbial community members. Species-specific or OTU-specific primers that anneal to internal variable regions can then be used to test for the presence of individual species. For both eukaryotic and prokaryotic rDNA, the variable rDNA regions show sufficient variability to develop amplification primers and probes that may be sensitive and specific to the organism to be tested.

For increased specificity and sensitivity in microarray experiments, variable sequence regions within the SSU rDNA may be utilized in a two-tiered strategy: (1) species-specific or OTU-specific PCR primers (e.g., Tables 2 and 3) can be multiplexed in individual PCR reactions to selectively amplify individual species or OTUs; (2) PCR products may then be labeled and hybridized to corresponding species-specific or OTU-specific oligonucleotide probes (e.g., Tables 2 and 3) immobilized on a microarray, where the probes immobilized on the array have sequences that are included in the amplified DNA products. The process may provide improved specificity and sensitivity because each of the species-specific or OTU-specific primer pairs and probes are designed using the same rDNA sequence.

To determine nucleic acid sequences that are specific to a single OTU, and thus can be used to detect the presence of a specific OTU in an ecosystem of interest, water samples were used to isolate DNA sequences derived from microbial ribosomal DNA. The individual ribosomal DNAs were cloned and the nucleic acid sequence for each clone was determined. Then, sequences from each rDNA clone were simultaneously aligned with either a prokaryotic rDNA sequence or a eukaryotic rDNA sequence to determine regions of variability for the cloned rDNAs. In this way, primers and probes (e.g., Tables 2 and 3) specific a particular OTU (or microbe population) were identified.

To ascertain the relative location and degree of variability among variable regions, rDNA sequences can be initially aligned using the multiple alignment computer program CLUSTAL W (Thompson et al., 1994, *Nucleic Acids Res.*, 22:4673–4680). Multiple alignment parameters including a gap initiation penalty of three, a gap extension penalty of one, a base match score of one, and a base mismatch penalty of one were used. Transitions were not weighted and terminal gaps were not penalized. By aligning the cloned sequences with either the prokaryotic or eukaryotic rDNA, the SSU rDNA was demarcated into conserved and variable sequence regions, which were further aligned by hand to optimize the multiple alignment result where necessary. For prokaryotic primer sequences and probes (Table 3), variable sequence regions were used within nucleotides 50–880 (V1, V2, V3, and V4), based on alignments with *E. coli* rDNA (SEQ ID NO: 317) (FIG. 10A) (Brosius et al., 1981, J. Mol. Biol., 148:107–127; GenBank Accession No. V00348). Specifically, nucleotides 50–150 (V1 region) (SEQ ID NO: 319) or 160–250 (V2 region) (SEQ ID NO: 320) in the forward direction and nucleotides 430–510 (V3 region) (SEQ ID NO: 321) or 820–880 (V4 region) (SEQ ID NO: 322) (FIG. 10C) in the reverse direction allow for OTU-specific amplification by PCR that includes a region that complements microarray probes, which include nucleotides 160–250 (V2) (SEQ ID NO: 320) or 430–510(V3) (SEQ ID NO: 321). Primer sequences within these regions were selected to maximize specificity for each individual organism. Based on alignments with *S. cerevisiae* (Rubstov et al., 1980, Nucl. Acids Res., 8:5779–5794; GenBank Accession No. V01335) (SEQ ID NO: 318) (FIG. 10B) using the same alignment conditions, eukaryotic primer sequences and probes (Table 2) included variable sequence regions within nucleotides 50–1100 (V1, V2, V3, and V4). Specifically, positions 50–550 (V1 plus flanking sequence region) (SEQ ID NO: 324) in the forward direction and positions 800–870 (V3) (SEQ ID NO: 326) or 1000–1100 (V4) (SEQ ID NO: 327) in the reverse direction allow for OTU-specific amplification of a region that includes a region that complements probes within nucleotides 600–800 (V2) (SEQ ID NO: 325) or 1000–1100 (V4). When the sequence regions specified for primer and probe design do not include OTU-specific sequences, such that primers designed for two microbes would be the same or substantially similar, other variable regions are used. For example, prokaryotic primer sequences have also included nucleotides 1100–1160 (V6) (SEQ ID NO: 323) in the reverse direction and eukaryotic primer sequences have also included nucleotides 1350–1450 (V5) (SEQ ID NO: 328) in the reverse direction, where necessary.

Thus, in one embodiment of the present invention, amplification of a genomic sample DNA may be performed by multiplex PCR using primers chosen to provide products that can hybridize to taxon-specific ribosomal DNAs. Using this protocol can dramatically reduce non-specific labeling, and eliminate the need for intermediate PCR reactions, which reduce sensitivity. Oligonucleotide probes that may be spotted to provide a taxon-specific array (e.g., SEQ ID NOS: 5–113), and the primers used to detect (i.e., amplify) such sequences in water samples (e.g., SEQ ID NOS. 114–316), are shown in Tables 2 and 3. For example, primers having the sequences SEQ ID NOS. 114 and 115 (1F and 1R, respectively) may be used to amplify DNA from a water sample such that the amplification product contains sequences that will hybridize with an oligonucleotide probe (1P) immobilized on an array, where probe 1P has the sequence described by SEQ ID NO: 5. In one embodiment, multiple primer pairs (e.g., SEQ ID NOS: 114–214) are used to amplify DNA sequences that include SEQ ID NOS: 5–60). In addition, as is known in the art, the reverse complementary sequence of each probe sequence in Tables 2 and 3 may also be spotted as an oligonucleotide on the array.

TABLE 2

Eukaryotic probes and primer pairs used for multiplex PCR

| Eukaryotic primer sequence (5'–3') | SEQ ID NO: | PCR No. | Template | GenBank Accession No. | Probe Sequence (5'–3') | SEQ ID NO: | Oligo No. |
|---|---|---|---|---|---|---|---|
| ATACAGGCGC TCGATAAGAG | 114 | 1F | *Acanthamoeba mauritaniensis* | AY351647 | ACTAACTCAATAGC AGGAACGGGAATC CAGAAGGAGGGGA CGGGCGGGCC | 5 | 1P |
| AGCTGCTAGG GGAGTCATTC | 115 | 1R | | | | | |
| AACTCGACTTT ATGGAAGGG | 116 | 2F | *Cryptosporidium parvum* | AF222998 | GATTTCTCATAAGG TGCTGAAGGAG-TAAGGAACAACCT CCAATCTCTAGT | 6 | 2P |
| CAAAGTCCCTC TAAGAAGAC | 117 | 2R | | | | | |
| TTGGCTTTAGC CGGCGATAG | 118 | 3F | *Cyclospora cayetanensis* | AF111183 | AGTTCCGGAACACC AACGCACGCAGCG AAGCGCGGAAGGC TACCGGAAGA | 7 | 3P |
| AAGCCAAGGT AGGCGTTTCC | 119 | 3R | | | | | |
| GACGACACAT AACTCTAGAG | 120 | 4F | *Entamoeba histolytica* | X65163 | GAAATGTCTTATTG ACATCCCCTCAGCA TTGTCCCATGCTTG AATATTCA | 8 | 4P |
| TCATCCAATCC TTGGTTGAC | 121 | 4R | | | | | |
| AACTTGCCCAA TGCGCGG | 122 | 5F | *Giardia intestinalis* isolate Dog19 | AF199449 | CCCACGCGGCGGG TCCAACGGGCCTGC CTGGAGCGCTCCCG TTTCCTCGT | 9 | 5P |
| GGGAATACGG TGGTGTCTG | 123 | 5R | | | | | |
| GATTGGAATG ATGGGAATCC | 124 | 6F | *Isospora belli* | AF106935 | GAATTTCACCACGT ACACACCCCTAAG GGCGGACTGGCTG CTTCCAGCAG | 10 | 6P |
| AGGAGAAGTC AAGTATGACG | 125 | 6R | | | | | |
| GCGGTAGTAA GGAGACGTG | 126 | 7F | *Microsporidium* sp. STF | AY140647 | CTTTATCATCGGAC TCGCCCCTGGCCAG | 11 | 7P |

TABLE 2-continued

Eukaryotic probes and primer pairs used for multiplex PCR

| Eukaryotic primer sequence (5'–3') | SEQ ID NO: | PCR No. | Template | GenBank Accession No. | Probe Sequence (5'–3') | SEQ ID NO: | Oligo No. |
|---|---|---|---|---|---|---|---|
| GCATCGGCATC GTTTACTGC | 127 | 7R | | | CGCTTTCGCCTCTG TCGCTCCT | | |
| TTCGGTGGTGA GGTATTATC | 128 | 8F | *Naegleria fowleri* | AF338423 | CCTCCAACCATCTC CTGATGGAACTAGT | 12 | 8P |
| AAGATCGCTG GGATAGTGTC | 129 | 8R | | | TACCCCGTAAACAC TCTTAGGT | | |
| ATCGAGTATCA ATTGGAGGG | 130 | 9F | OTU LT3A27, multi-copy, identified as *Asterionella formosa* | N/A | ACGGAGACAAACA AGCACCAACACAA | 13 | 9P |
| GACGGGGTCA ATACAACGAC | 131 | 9R | | | GTGAAGGGCACGT TGCTCCAACCA | | |
| GCCAATGGTCT TCTTATTGG | 132 | 10F | OTU LT1A42, multi-copy, identified as *Cryptomonas* sp., strain M420 | N/A | CAAGCAGAAAGGC ACGCGCGCACCGTC | 14 | 10P |
| GAGGTCGTAA ATTGACACTC | 133 | 10R | | | CAACCAGAGGCTG ACAGTTCACA | | |
| TTCAAACCGGC CTCGTTCTG | 134 | 11F | OTU LT1A4, multi-copy, identified as *Cryptomonas ovata*, strain CCAP 979/61 | N/A | GCACGCGCATGCC GTCCGACCAGAGG | 15 | 11P |
| CCCATAACCA ACGAAATAGC | 135 | 11R | | | CCGACAGCCCACA CGCGCCCAAAA | | |
| TTAGCGAATCG TGGCACGTC | 136 | 12F | OTU LT2A7, multi-copy, identified as *Dileptus* sp. | N/A | TAACTGTCCCTGAT GGGACTAGTAGGG | 16 | 12P |
| AATGTATTCCT GCAAACGCC | 137 | 12R | | | ATTGGTTTAAAGCC TCTCCCTAG | | |
| GGGTTCTTACG AACTTTGGG | 138 | 13F | OTU LT2A19, single-copy, identified as *Coleps* sp. | N/A | TCTCAGACGGATGA ACGCCTATACCTCG | 17 | 13P |
| CTGATCGGGCT TGAAAGACC | 139 | 13R | | | ACCGGAGCCGCTGT ACAAACGC | | |
| TATCGAGGAC CAATTGGAGG | 140 | 14F | OTU LT3A2, single-copy, unidentified | N/A | ACCTAATGCCACAC AGATTCCACCCAAG | 18 | 14P |
| GACGGAGTCA ATACAACGAC | 141 | 14R | | | GATGGACGAGCTG CCCAAGTAC | | |
| TGGACTCTTTT GAGTCCGGC | 142 | 15F | OTU LT1A3, single-copy, unidentified | N/A | CCATCTGCGCCTCA ACATGCAGGTAAA | 19 | 15P |
| ATCAATACTAA CACCCACCG | 143 | 15R | | | TCGTAAAGAAAAG GCCAAATAGC | | |
| TAACGATAGC GGGCTCGTTC | 144 | 16F | OTU LT1A10, multi-copy, unidentified | N/A | GTATCACACCAGG GAGGTTATTGAACG | 20 | 16P |
| CATAGGGTGCT GATAGAGTC | 145 | 16R | | | CAGACCACCTAGGT AACACCTAA | | |
| CCGAGATTTCT CGGAAATTG | 146 | 17F | OTU LT2A12, multi-copy, unidentified | N/A | AAGGATGCTTTCAG GCACTGATCGCGCA | 21 | 17P |
| TTTCTCACGAG GTGCTGAGG | 147 | 17R | | | CACTGAGGTGGGA AGTGCCGTT | | |
| ATGGTGGAGG TGATTCATTC | 148 | 18F | OTU TL1A16, multi-copy, unidentified | N/A | TAAGTGCAACGGG ATCCTCATGCAGAA | 22 | 18P |
| AATTGACATCC ACTGATCCC | 149 | 18R | | | AGACCCGAGCCTG CCGTCCGACC | | |
| GATACAGGAC TCATCCGAGG | 150 | 19F | OTU TL1A1, multi-copy, unidentified | N/A | AAAGTAAACCTGC CAGCACAGACGGA | 23 | 19P |
| AAACGCCTGC AGATCGCTAG | 151 | 19R | | | CACTCGGCGAAGA GCACCCGCCTG | | |
| ACAATGCCAGC GCCTTTCAAG | 152 | 20F | OTU TL1A2, multi-copy, unidentified | N/A | TTAATGCCAGATAT GCTCTCCCCGAGGA | 24 | 20P |
| TGGAGTCGTTA CAAACTTCC | 153 | 20R | | | TGGCTGCAGACAC ATAGTACAG | | |
| TCGGCGACGA TGATTCATTC | 154 | 21F | OTU TL1A9, multi-copy, unidentified | N/A | AGTCGACCAGTTCT GACCCATGAGGCC | 25 | 21P |
| TGAACAAACC ACGCCCAATC | 155 | 21R | | | GACCGGCTGAGCTC ACTCTGAAC | | |
| CGGTTTACCGG CGATAGATC | 156 | 22F | OTU TL1A12, multi-copy, unidentified | N/A | TCAAACCTGATTCA AACCCGTATGGGTC | 26 | 22P |
| TTCTCTCGAGG TGCTGAAGG | 157 | 22R | | | GATCGGTCGTCCTC AGCAGAAA | | |
| AATCGGATCG CATGGGCTAG | 158 | 23F | OTU TL1A21, multi-copy, unidentified | N/A | TGGTAGGCTACCAC TGCGCATCCACAAG | 27 | 23P |
| GAACGGGATA ATTCTCGCCC | 159 | 23R | | | GAGGCAGAAACTA GCCAACCAG | | |
| CCCACTTATGT GGGTTTGAC | 160 | 24F | OTU CL1A3, single-copy, | N/A | GCTTCATGCAGGAG CATCTCAGCATCCA | 28 | 24P |

TABLE 2-continued

Eukaryotic probes and primer pairs used for multiplex PCR

| Eukaryotic primer sequence (5'–3') | SEQ ID NO: | PCR No. | Template | GenBank Accession No. | Probe Sequence (5'–3') | SEQ ID NO: | Oligo No. |
|---|---|---|---|---|---|---|---|
| GAAGTAGAGG ATCTTGCCTC | 161 | 24R | unidentified | | GTGTTGGGACCAG GACATACTG | | |
| GACAGCTTCTT TAATGGAGG | 162 | 25F | OTU CL1A4, single-copy, | N/A | GTTATGATTCTATC TCAAGGAGGAGCG | 29 | 25P |
| ATCTGTTGGTC CTCCAAATC | 163 | 25R | unidentified | | TCCTGTGCTCTCCC ACTTCACTC | | |
| AATACAGGGC TCTTTGAGTC | 164 | 26F | OTU CL1A5, single-copy, | N/A | TCCAGAAGGTGAG GCCGACGCAAAGA | 30 | 26P |
| AAGACGTACC ACCGATCCTG | 165 | 26R | unidentified | | GTACTCACCGCTAG GTGGACCCTC | | |
| TAACAATGCG GAGCCTTCGG | 166 | 27F | OTU CL1A6, single-copy, | N/A | AGAGTAAAGGACG CAGGTCCGGACGC | 31 | 27P |
| AAGAACGTCC GCCAATCCTG | 167 | 27R | unidentified | | CGACAAGTGAATG CCGACGCCTTC | | |
| TATCTGGCGCT TTTGCGTCG | 168 | 28F | OTU CL1A8, multi-copy, | N/A | TCTCTAGAAGGATG CCCAACCCGCACCG | 32 | 28P |
| CAACGTCTACC CATCCCAAG | 169 | 28R | unidentified | | GCACTCACAGGCC AAAAAGGCC | | |
| ACTCGGGAAC CTAGTTCTAC | 170 | 29F | OTU LT2A20, single-copy, | N/A | CGAAGACGGATGA CTAACTATATACTG | 33 | 29P |
| TCTCTTACGGC GCCGAAAAG | 171 | 29R | unidentified | | ACGTAAGCCAGCA TATAAATAGC | | |
| AGGGCCAACG GTCTTGTTAT | 172 | 30F | OTU LT1A5, multi-copy, | N/A | CACAATTAAGTGCA ACGGGATCCTCATG | 34 | 30P |
| TCGGAAATTGA CATCCACTG | 173 | 30R | unidentified | | CAGAAAGACCCGA GCCTGCCGT | | |
| CTCTCTCCGAG TATCAATTG | 174 | 31F | OTU LT1A8, multi-copy, | N/A | TATTAACGCACTAC GCCCTGGAAGGAT | 35 | 31P |
| ACTTCCCTCAA TCGCTAGTC | 175 | 31R | unidentified | | GCTTTCAGGCACTG ATCGCGCAC | | |
| GCAGAGCTTC ACAGTTTTGC | 176 | 32F | OTU LT1A9, single-copy, | N/A | ACAGCTACCACCAC CCTAAGGTGGGGA | 36 | 32P |
| AGACGTCTCCT GATCGCAAG | 177 | 32R | unidentified | | GGTCATCCCGATCA GAGATTCAA | | |
| N/A | | | OTU LT1A11, single-copy, unidentified | N/A | TTCCAAGAGGATGC CTCGGTCTAACCAG ACACAAACCCGTAT GGGTCGGT | 37 | 33P |
| N/A | | | OTU LT1A13, single-copy, unidentified | N/A | AAGTGTTTTCCGGA AGATGGACGCAAA CACCCGGTACACA GACCGCAGT | 38 | 34P |
| ATACGTCCCGG GACTGCAAT | 178 | 35F | OTU LT3A5, multi-copy, | N/A | TAACAGAAGGATG GTAGGGCGGCTCA | 39 | 35P |
| CGAAGGCGGA TAATTCTCGC | 179 | 35R | unidentified | | GCGCACTCAACTTG AGGGCAAAGT | | |
| ACAATGCAGG GCCTTTACGG | 180 | 36F | OTU LT3A6, multi-copy, | N/A | ACAGTACAAGTCTT GCGACTAGACCGTC | 40 | 36P |
| GAATAACACT CACTGATCCC | 181 | 36R | unidentified | | CGGCCCAAAACCT GAAATCCAA | | |
| ATACAGGACT CATCCGAGGC | 182 | 37F | OTU LT3A7, multi-copy, | N/A | AAACAAGCCAGTA CCGAAAGCATTCG | 41 | 37P |
| AAACGCCTGC AGATCGCTAG | 183 | 37R | unidentified | | GACCGACTTCTGTC CGCCGAGATC | | |
| N/A | | | OTU LT3A11, single-copy, unidentified | N/A | GCAAGCGGATGAC TGTCAGAATCCCCG TCTAATGACTGAAG ACCTGAACA | 42 | 38P |
| CTTTACAGGTC TGGCAATTG | 184 | 39F | OTU LT3A13, single-copy, | N/A | ACCTAATGCCACAC AGATTCCACCCAAG | 43 | 39P |
| CATACAGTGCT GACAGGGTC | 185 | 39R | unidentified | | GATGGACGAGCTG CCCAAGTAC | | |
| CAGGGCCTTTT CAGGTCTTG | 186 | 40F | OTU LT1A1, multi-copy, | N/A | TTCAGAAAAGAAG TGTCGTCCCGATCG | 44 | 40P |
| CACAAGGTGC CAACAGAGTC | 187 | 40R | unidentified | | CACTACCGTAAGGC GGCAAGCGT | | |
| AACAATGTCTG GCCCTACGG | 188 | 41F | OTU LT1A38, multi-copy, | N/A | AATGCCGCTGGTCA CACGGAAGAAAGA | 45 | 41P |
| GTAAACAACG CCCACCGATC | 189 | 41R | unidentified | | AGCCGACCAAACA GTGCGACTTG | | |
| GAGGGCAAGT CTGGTGCCAG | 190 | 42F | All LT1A & LT3A OTUs | N/A | N/A | | |

TABLE 3

Prokaryotic probes and primer pairs used for multiplex PCR

| Prokaryotic primer Sequence (5'–3') | SEQ ID NO: | PCR No. | Template | GenBank Accession No. | Prokaryotic probe Sequence (5'–3') | SEQ ID NO: | Oligo No. |
|---|---|---|---|---|---|---|---|
| CGAATGGATTAAGAGCTTGC | 191 | 43F | *Bacillus anthracis* strain: S51 | AB116124 | GTGACAGCCGAAGCCGCCTTTCAATTTTCGAACCATGCGGTTCAAAATGTT | 46 | 43P |
| TGCCAGCTTATTCAACTAGC | 192 | 43R | | | | | |
| GAACGTACCATTTGCTACGG | 193 | 44F | *Brucella melitensis* | AF220149 | CCAACGCGGGCCGATCATTTGCCGATAAATCTTTCCCCCGAAGGGCACAT | 47 | 44P |
| ACCGTCATTATCTTCACCGG | 194 | 44R | | | | | |
| ACGGGCTTCGGCCTGGTG | 195 | 45F | *Burkholderia mallei* strain 2000031063 | AY305760 | AGGCCCGAAGGTCCCCCGCTTTCATCCTCAGATCGTATGCGGTATTAATC | 48 | 45P |
| TCCGGGTATTAGCCAGAATG | 196 | 45R | | | | | |
| GCTTGCTAGAAGTGGATTAG | 197 | 46F | *Campylobacter jejuni* strain B99/206 | AF550630 | TCCTACACCGAAAAACTTTCCCTACTCAACTTGTGTTAAGCAGGAGTATA | 49 | 46P |
| CGTCAGAATTCTTCCCTAAG | 198 | 46R | | | | | |
| TTTAGTGGCGGAAGGGTTAG | 199 | 47F | *Chlamydophila psittaci* clone cvCps2 | AY334530 | GGTCCGAAGATCCCCTTCTTTAATATGTTTTAGATGCCTAAACATACCAC | 50 | 47P |
| ATCTCTCTTATTCCCAAGCG | 200 | 47R | | | | | |
| AAGCTTCCTTCGGGAAGTGG | 201 | 48F | *Clostridium botulinum* strain AIP 355.02 | AY303799 | CGCCGCGGGTCCATCTCAAAGCAATAAATCTTTGATAAGAA TABLE 3-continued Prokaryotic probes and primer pairs used for multiplex PCR

| Prokaryotic primer Sequence (5'–3') | SEQ ID NO: | PCR No. | Template | GenBank Accession No. | Prokaryotic probe Sequence (5'–3') | SEQ ID NO: | Oligo No. |
|---|---|---|---|---|---|---|---|
| N/A | | | Escherichia coli O157:H7 EDL933 | NC 002655 | ACTGGCGGGAAC ACATGAAAACGT AACCACGCTACC AGTAGCCAGAAG AA | 61 | 58P |
| N/A | | | Escherichia coli O157:H7 EDL933 | NC 002655 | CCATTAAAACTA ATGCCTGTCATA ATGGAGGGGGAT TCAGCGAAGTTA TT | 62 | 59P |
| AAGACATCTTC ACCGTTC | 215 | 60F | Escherichia coli K12 | NC 000913 | AAGACATCTTCA CCGTTCACGATAT TTTGAAAGCACG AGGGGAAATCTG A | 63 | 60P |
| TCAGATTTCCC CTCGTGC | 216 | 60R | | | | | |
| N/A | | | Escherichia coli K12 | NC 000913 | CACCGTCGCTTTA AAACGCGCCCGG TGGGAGAATCGT CGTTGTACATTTA | 64 | 61P |
| N/A | | | Escherichia coli K12 | NC 000913 | TTTCTGATCGCGT TGCTGCGCTGATC AAAGAAGTAAAC AAAGCAGCTTAA | 65 | 62P |
| ATGGCATCCGT GGTATCC | 217 | 63F | Escherichia coli K12 | NC 000913 | ATGGCATCCGTG GTATCCCGACTCT GCTGCTGTTCAA AAACGGTGAAGT G | 66 | 63P |
| CACTTCACCGT TTTTGAA | 218 | 63R | | | | | |
| AACAGCTTGCT GTTTCGCTG | 219 | 64F | Shigella sonnei | X96964 | N/A | | |
| TTCCTCCCCGC TGAAAGTAC | 220 | 64R | | | | | |
| CAGGTCTTAGG ATGCTGACG | 221 | 65F | Francisella tularensis strain 3523 | AY243028 | AGGCTCATCCAT CTGCGACACGCC GAAAGCCACCTT TAATCCACAGAT AT | 67 | 65P |
| AAGGCTATTA ACCTTGAGGC | 222 | 65R | | | | | |
| AGACTATCTAC TTCTGGTGC | 223 | 66F | Legionella pneumophila serogroup 6 | AJ496383 | AATCCTTAAAAG TCGGTCGTAGTCC GGATTGGAGTCT GCAACTCGACTC C | 68 | 66P |
| ATACAGGTGCT GCATGGCTG | 224 | 66R | | | | | |
| GAGTAGCAAT ACTCAGCGGC | 225 | 67F | Leptospira interrogans | Z12817 | ATCTCCGAGCAA TAAATCTTTACCC GAAAAATCTTAT GATCTCTCGGGA C | 69 | 67P |
| TACCATCATCA CATTGCTGC | 226 | 67R | | | | | |
| GAGCTTGCTCC TGGATTCAG | 227 | 68F | Pseudomonas aeruginosa strain WatG | AB117953 | TCATCTGATAGC GTGAGGTCCGAA GATCCCCCACTTT CTCCCTCAGGAC G | 70 | 68P |
| GTAACGTCAA AACAGCAAGG | 228 | 68R | | | | | |
| AGTTAATTAGT GGCAGACGG | 229 | 69F | Rickettsia prowazekii | M21789 | ATCTGACGCGGG CCCATCCATCAG CGATAAATCTTTC CTCCGTAGAGAA T | 71 | 69P |
| ACTAAACCGC CTACGCACTC | 230 | 69R | | | | | |
| AGCTTGCTGCT TTGCTGACG | 231 | 70F | Salmonella typhimurium | Z49264 | CTTGGTGAGCCG TTACCTCACCAAC AAGCTAATCCCA TCTGGGCACATCT | 72 | 70P |
| TAACCACAAC ACCTTCCTCC | 232 | 70R | | | | | |
| GAACTTGTTCC TTGGGTGGC | 233 | 71F | Vibrio cholerae CECT 514 T | X76337 | ATCCCACCTGGG CATATCCGGTAG CGCAAGGCCCGA AGGTCCCCTGCTT T | 73 | 71P |
| TTAACCACCTT CCTCCCTAC | 234 | 71R | | | | | |
| GTAGTTTACTA CTTTGCCGG | 235 | 72F | Yersinia pestis | AF366383 | TCTGGGTTCATCC GATGGCGTGAGG CCCTAAGGTCCC CCACTTTGCTCTT | 74 | 72P |
| GAGCGTATTA AACTCAACCC | 236 | 72R | | | | | |
| GGAAAGTGGC CCTCTGATTC | 237 | 73F | Arsenite-oxidizing bacterium | AF406554 | TCAAGACCCACG GCTATTAACCGT AAGCTTTTCCTCC | 75 | 73P |
| CCATAAATGA | 238 | 73R | | | | | |

TABLE 3-continued

Prokaryotic probes and primer pairs used for multiplex PCR

| Prokaryotic primer Sequence (5'–3') | SEQ ID NO: | PCR No. | Template | GenBank Accession No. | Prokaryotic probe Sequence (5'–3') | SEQ ID NO: | Oligo No. |
|---|---|---|---|---|---|---|---|
| ACCCAACGGC | | | MLHE-1 | | CTGCTGAAAGTGC | | |
| ACCGGATACACCTTCATACC | 239 | 74F | Thiomicrospira sp. CVO | U46506 | GCCGGTGCTTATTCATATGCTACCGT | 76 | 74P |
| CCGCAATGACAAGCATCACG | 240 | 74R | | | CATTTTCTTGACATATAAAAGGAG | | |
| ACGCTCCGATTTCACAGTTC | 241 | 75F | Desulfovibrio longreachii | Z24450 | GTACCGTCAGACCATGGCTGATTA | 77 | 75P |
| AAGTCCAGCAGTATCAAGGG | 242 | 75R | | | GCACCATGGCGGTTCTTCCCTCCTGA | | |
| TGGGTTTACCTAACACTACG | 243 | 76F | Bacillus arsenicoselenatis | AF064705 | CAAGGTACCGCCCTATTTGAACGGT | 78 | 76P |
| TAGAGTCGAGTTACAGACCG | 244 | 76R | | | ACTTGTTCTTCCCTAGCAACAGAGC | | |
| ATCATGAGTTCACATGTCCG | 245 | 77F | Uncultured human fecal bacterium HF74 | AF233412 | TATTCATAAGGTACATACAAAACACCACACGTGGCGAACTTTATTCCCTT | 79 | 77P |
| CAATCGGAGTTCTTCGTG | 246 | 77R | | | | | |
| ATCATGAGTTCACATGTCCG | 247 | 78F | Uncultured human fecal bacterium HF8 | AF233408 | TATTCATAAAGTACATGCAAACGGGTATGCATACCCGACTTTATTCCTTT | 80 | 78P |
| CAATCGGAGTTCTTCGTG | 248 | 78R | | | | | |
| GCCGTCTACTCTTGGCC | 249 | 79F | Uncultured human fecal bacterium HF10 | AF233413 | TATTCATACGGTACATACAAAAGGCACACGTGCCTCACTTTATTCCCGT | 81 | 79P |
| CCTGCCTCTACTGTACTC | 250 | 79R | | | | | |
| ACGGGTGCTTGCACCTGG | 251 | 80F | Burkholderia cepacia | AB091761 | AGGCCCGAAGGTCCCCCGCTTTCATCCGTAGATCGTATGCGGTATTAATC | 82 | 80P |
| CGACTGTATTAGAGCCAAGG | 252 | 80R | | | | | |
| GTTGGCCGATGGCTGATTAG | 253 | 81F | Burkholderia cepacia genomovar III | AF148556 | CGGTACCGTCATCCCCCGACTGTATTAGAGCCAAGGATTTCTTTCCGGAC | 83 | 81P |
| TCTGCCATACTCTAGCCTGC | 254 | 81R | | | | | |
| ACATGCAAGTCGTACGAGAG | 255 | 82F | OTU LT3A11, multi-copy, identified as Unidentified cyanobacterium clone LD27 | N/A | AGCCGCAAGCTTCTCTTTAGGCGGAAATCCATTTCACTCGAAAGCATATG | 84 | 82P |
| ACACGTCATTTATTCCTCCC | 256 | 82R | | | | | |
| ACGAACCTTCGGGTTAGTGG | 257 | 83F | OTU LT1A53-3A9, multi-copy, identified as Synechococcus sp. | N/A | AGACGCGAGCTCATCCTCAGGCGAAATTCATTTCACCTCTCGGCATATGG | 85 | 83P |
| TCAAGTACCGTCAGATCTTC | 258 | 83R | | | | | |
| AAAGGCCTACCAAGGCTTCG | 259 | 84F | OTU LT1A53, multi-copy, identified as Synechococcus sp. LBG2 | N/A | CCATCGCAGTAATGGAGTTAAGGTCCACGCTTTGACGACAGACTTAAAAG | 86 | 84P |
| GGCACTCTCTGTTTCCAAG | 260 | 84R | | | | | |
| AAAGGCTTACCAAGGCATTG | 261 | 85F | OTU LT3A9, multi-copy, identified as Synechococcus sp. LBP1 | N/A | CCATCGCTGAAATGGAGTTGAGCTCCACGCTTTAACGACAGACTTGTAAA | 87 | 85P |
| CCTCCGGTTTCCCAGAG | 262 | 85R | | | | | |
| GTAACAGGTCTTTCGGGATG | 263 | 86F | OTU TL1A7, multi-copy, identified as Uncultured beta proteobacterium clone OSIL-16 | N/A | CGCTCTAGTAGCACAAGGCCCGAAGGTCCCCTGCTTTCATCCATAGATCT | 88 | 86P |
| CAAGACTTTTCGTTCCGTAC | 264 | 86R | | | | | |
| TCTTTCACCGGAGCTTGCTC | 265 | 87F | OTU TL1A9, multi-copy, identified as Enterococcus gallinarum strain LMG 13129 | N/A | TCAGTGACGCAAAAGCGCCTTTCAACTTTCTTCCATGCGGAAAATAGTGT | 89 | 87P |
| CTCTCATCCTTGTTCTTCTC | 266 | 87R | | | | | |
| ACGGTCGCGTAACACGTAAG | 267 | 88F | OTU LT1A31, multi-copy, identified as | N/A | TCCTGAAGCGATAAATCTTTAGACACAAGTCGATGC | 90 | 88P |
| CGTCAAATTTC | 268 | 88R | | | | | |

TABLE 3-continued

Prokaryotic probes and primer pairs used for multiplex PCR

| Prokaryotic primer Sequence (5'–3') | SEQ ID NO: | PCR No. | Template | GenBank Accession No. | Prokaryotic probe Sequence (5'–3') | SEQ ID NO: | Oligo No. |
|---|---|---|---|---|---|---|---|
| TTCCCACTC | | | Uncultured Crater Lake bacterium CL500-18 | | CGACTCGTGACC AC | | |
| ATGAAGCTACT TCGGTAGTG | 269 | 89F | OTU CL1A15, single-copy, identified as Uncultured Crater Lake bacterium CL0-27 | N/A | AGGTCATCTTCA ACCGAAAAACTT TCCAGCCCCGAT CATGCGATCAGA GC | 91 | 89P |
| TGTAGGTACCG TCACTTTCG | 270 | 89R | | | | | |
| ATGAAGCACC TTCGGGTGTG | 271 | 90F | OTU LT1A54, multi-copy, identified as Uncultured Crater Lake bacterium CL0-64 | N/A | TCATCTTCAACCG AAAAACTTTCCA AACCCGCGGATG CCCGCAGGTTTC A | 92 | 90P |
| TGCAGGTACC GTCACTTTCG | 272 | 90R | | | | | |
| GATCTTTGATC TTAGTGGCG | 273 | 91F | OTU LT1A55, multi-copy, identified as Uncultured freshwater bacterium LCK-26 | N/A | CAGACGCGAGCT CTTCCTAAGGTG GATAAATCCTTTT ACCTCTCGGCGT A | 93 | 91P |
| TCAAGTACCGT CAGAACTTC | 274 | 91R | | | | | |
| AACGTACCCA AGAGTGGG | 275 | 92F | OTU CL1A9, multi-copy, identified as Zoogloea ramigera | N/A | GGCCGCTCCAGG AGCACGAGGTCT TGCGATCCCCCG CTTTCATCCTTAG A | 94 | 92P |
| AAGGATATTA GCCTCTACCG | 276 | 92R | | | | | |
| TGAAGTTCCTT CGGGAATGG | 277 | 93F | OTU LT1A27, multi-copy, identified as Uncultured actinomycete clone SFD1-39 | N/A | ATCTTTCATCAAA ATTTTTTCCCGGC TCGGCGATGCCG CCAAGACGGAGT | 95 | 93P |
| TTCTTCCCTAC TGAAAGAGG | 278 | 93R | | | | | |
| CTCATCAGCAA TGGTGGGAG | 279 | 94F | OTU LT1A46, multi-copy, identified as Uncultured planctomycete clone CY0ARA-031E04 | N/A | TCATGTAAGCCG CTCCTCCGGCGG AATCACACCTTTG CTCCGCAGAGTT C | 96 | 94P |
| TCAACTCCGGA GGAGAACC | 280 | 94R | | | | | |
| GGCAGCACGG TCTAGTTTAC | 281 | 95F | OTU TL1A1, multi-copy, unidentified | N/A | TATTCTTAAAGCG CCAGGCCTTGCG GTCCCCAGCTTTT CTCCTCAGAGAT | 97 | 95P |
| TCAAATCCTCC TCCCCACTG | 282 | 95R | | | | | |
| GTCAGACTTCG GTCTGATTG | 283 | 96F | OTU TL1A2, multi-copy, unidentified | N/A | CTCCATCAGCGC CCTTGCGAGCTTT CATCCCTTCTGCG ACGAAGGGATCG | 98 | 96P |
| GGTACTTCTTC CCGAGCAAC | 284 | 96R | | | | | |
| ATGTAGCAAT ACAGGACAGC | 285 | 97F | OTU TL1A6, single-copy, unidentified | N/A | GGGGCACGGGCT CATCTTGGGGCG GAATCACACCTTT GGTCCGCAAACA T | 99 | 97P |
| CGTACATTTGA TTCCCTACG | 286 | 97R | | | | | |
| ATGAAGCTGG AGCTTGCTCC | 287 | 98F | OTU CL1A2, multi-copy, unidentified | N/A | TCCTTGACCAAA ATTCTTTCCACGC CCGTGGGATGCC CCAAGGCGTCGT A | 100 | 98P |
| GCGAGCTCATC CTTGACC | 288 | 98R | | | | | |
| ACGGGAGCAA TCCTGGTG | 289 | 99F | OTU CL1A10, multi-copy, unidentified | N/A | TGATATCGGCCG CTCCAATCGCGC GAGGTCTTGCGA TCCCCCGCTTTCA T | 101 | 99P |
| CCACTGTATTA GAGCAGACC | 290 | 99R | | | | | |
| ACGGCTTCGGC CTAGTAAAG | 291 | 100F | OTU LT2A3, multi-copy, unidentified | N/A | GCTCTTGCGAGCT CCCTTTCCCGAAA AACTCCTTACGA GTTCCGTCGCTC | 102 | 100P |
| AGGGCTGTTCA CCCTAATGG | 292 | 100R | | | | | |
| TTAACTTAAGT GGCGGACGG | 293 | 101F | OTU LT2A12, multi-copy, unidentified | N/A | AGACGCGAGCTT CTCTTTAGGCGG ATTACTCCATTTC | 103 | 101P |
| GGTACACGTC | 294 | 101R | | | | | |

TABLE 3-continued

Prokaryotic probes and primer pairs used for multiplex PCR

| Prokaryotic primer Sequence (5'–3') | SEQ ID NO: | PCR No. | Template | GenBank Accession No. | Prokaryotic probe Sequence (5'–3') | SEQ ID NO: | Oligo No. |
|---|---|---|---|---|---|---|---|
| GTTTTATTCC | | | | A | ACTCGGAAGCAT | | |
| TAACGCGGGG CAACCTGG | 295 | 102F | OTU LT2A16, multi-copy, unidentified | N/A | CGCTCCAATAGC GAGAGGTCTTGC GATCCCCCCCTTT CACCCGAAGGTC G | 104 | 102P |
| GGGTATTAGCC CAGAGCG | 296 | 102R | | | | | |
| AGAGTTTGATC CTGGCTCAG | 297 | 103F$_1$ | OTU LT1A15, single-copy, unidentified | N/A | CGGTCCCAGCGTT TCCAGTAATCTCT CTCTAGACTACTG CTTACGACGTA | 105 | 103P |
| ACGGAGGTAG CAATACCTTA | 298 | 103F$_2$ | | | | | |
| GTGCTTCTTCT TCCGGTACC | 299 | 103R | | | | | |
| TTCGGTTATGT TGATGGCGA | 300 | 104F | OTU LT1A16, multi-copy, unidentified | N/A | TAATCCTAAAGC GCCAGGCCTTGC GGTCCCCAGCTTT CCTCCTAAGAGA T | 106 | 104P |
| TCGGGTAACGT CAATAAACC | 301 | 104R | | | | | |
| AACCCCGGTG GCGAGTGG | 302 | 105F$_1$ | OTU LTIA18, multi-copy, unidentified | N/A | GTCCCCCGCTTTC ATCCATAGATCG TATGCGGTATTA GCGTAACTTTCGC | 107 | 105P |
| AACCCTGGTG GCGAGTGG | 303 | 105F$_2$ | | | | | |
| TTCTTACGGTA CCGTCATG | 304 | 105R | | | | | |
| GAGCGATGAA GTTTCTTCGG | 305 | 106F | OTU LT3A1, single-copy, unidentified | N/A | CAATATTCGGTAT TAGCACCGGTTTC CCGGTGTTATCCC AAAGTGGAGGG | 108 | 106P |
| AGCCGGTGCTT CTTTTGTAG | 306 | 106R | | | | | |
| GGTAACAGGT TAAGCTGACG | 307 | 107F | OTU LT3A2, multi-copy, unidentified | N/A | AGGTCTTGCGAT CCCCCCCTTTCAC CCGTAGGTCGTA TGCGGTATTAATC | 109 | 107P |
| CAGAGTATTA ATCCGAAGCG | 308 | 107R | | | | | |
| GGTCTAGTTTA CTAGATGGG | 309 | 108F | OTU LT3A7, multi-copy, unidentified | N/A | CAGCTTTTCTCCT CAGAGATTACGC GGTATTAGCCTG AGTTTCCCCAGGT | 110 | 108P |
| TTCTTCTGTGG GTAACGTCC | 310 | 108R | | | | | |
| CATCGGAACG TACCTTATCG | 311 | 109F | OTU LT1A35, multi-copy, unidentified | N/A | CTTTCCCCCTCAG GGCGTATGCGGT ATTAGCGCAACT TTCGCTGCGTTAT | 111 | 109P |
| CGCAGTCTGTG TTAGAGCTG | 312 | 109R | | | | | |
| CGTGAGAATCT ACCCTTAGG | 313 | 110F | OTU LT1A55, multi-copy, unidentified | N/A | CAGACGCGAGCT CTTCCTAAGGTG GATAGATCCTTTT ACCTCTCGGCAT A | 112 | 110P |
| GCTTGCATCCT CTGTATTAC | 314 | 110R | | | | | |
| TGTCGTCAGCT CGTGTCG | 315 | 111F | Control 1372 | N/A | TGACGGCGGTG TGTACAAGGCCC G | 113 | 111P |
| AAGGAGGTGA TCCAGCCG | 316 | 111R | | | | | |

The PCR products in each reaction mixture (e.g., 16S rDNA and 18S rDNA) may be generated from dNTPs which contain a mixture of dATP, dGTP, dCTP, dTTP, and amino allyl-dUTP. The labeling step may employ dye incorporation resulting from a coupling reaction between a cyanine (Cy) and the PCR product. The pools of labeled PCR products may be hybridized with the array, whose immobilized oligonucleotides specify 50-mer sequences that are complementary to at least some of the individual rDNA sequences amplified from each sample. In some cases, the experiment may be replicated by performing a second "dye swap" experiment to minimize any false signals due to differential incorporation of the dye in the amplification products.

Also, probes that target taxa at different hierarchical levels may be included in the array in order to optimize detection of desired bioindicator organisms. For example, in addition to developing PCR primers that are specific to a single species, primers that are capable of detecting several species in a particular genus may be developed (e.g., Oldach, D. W., et al., 2000, Proc. Natl Acad. Sci. U.S.A. 97:4303–4308). The more generic primers may be used both as a confirmation that a particular genus is present in any sample that tested positive with the more specific primers, and as an indicator that potentially unknown or undetected members of the genus are also present.

The array may provide a qualitative result and/or a quantitative result. For example, as shown in FIG. 11, an array of prokaryotic rDNA sequences and/or an array of eukaryotic rDNA sequences may be probed using PCR amplified rDNA sequences amplified from genomic DNA from a water sample to provide qualitatively different patterns of hybridization. For example, DNA from a water sample may be amplified using prokaryotic specific primers and then labeled with a red dye (Cy5) to provide a "red"

prokaryotic probe (FIG. 11A-1) that recognizes prokaryotic sequences immobilized at designated positions on an array (FIG. 11B). Alternatively or additionally, DNA from a water sample may be amplified using eukaryotic specific primers and then labeled with a green dye (Cy3) to provide a "green" eukaryotic probe (FIG. 11A-2) that recognizes eukaryotic sequences immobilized at designated positions on an array (FIG. 11B).

Figure 12A:
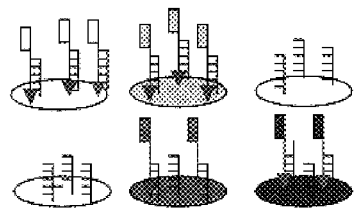
FIG. 12 shows a schematic diagram of hybridization of an array to two samples, in accordance with an embodiment of the present invention, where multiplex PCR reactions of each sample use the same primers, but the product of the amplification reaction from the first sample is labeled with Cy3 (green) and the product of the amplification reaction from the second sample is labeled with Cy5 (red). Panel A shows a schematic representation of the red (darkest arrowhead) and green (lighter arrowhead) amplified DNA hybridizing to immobilized DNA at an individual position on the array; Panel B shows a schematic representation of the color as viewed at each array position, wherein the overall color may comprise an average of the colors of the hybridizing probes; and Panel C shows an actual results of a hybridization experiment using red and green labeled probes, where the top panel shows PCR reactions using 16S primers, and the bottom panel shows the same samples amplified with 18S primers, and where prokaryotic oligonucleotides are spotted on the left side of each panel and eukaryotic oligonucleotides are spotted on the right side of each panel; green spots in lower right-hand position of each grid are for orientation.
Figure 12C:
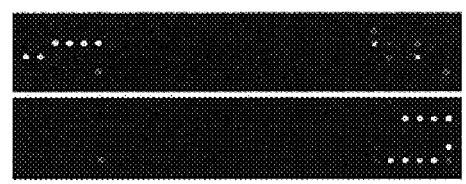
Figure 12B:
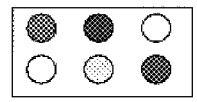

The array may also be used as a quantitative assessment tool, to monitor the change in various microbes over time, or to monitor the relative amounts of a microbe between two samples that vary in location (e.g., for two different bodies of water, or two locations in one body of water) or time of sampling (e.g., a single body of water sampled at two different seasons). Referring now to FIG. 12, an array may be probed with amplified DNA that corresponds to both 16S (prokaryotic) rDNA sequences and/or 18S (eukaryotic) rDNA sequences. To distinguish the two samples, amplification from the first sample may be labeled with a first dye (e.g., Cy3, green), whereas the amplification from the second sample may be labeled with a second dye (e.g., Cy5, red). As shown in FIG. 12A, the nucleic acids immobilized at a particular position (e.g., location or address) on the array, will bind to a complementary nucleic acid probe that is labeled either with the green dye (from the first sample), or the red dye (from the second sample). Upon hybridization, if hybridization is specific to probe from sample 1, a green spot will result; if hybridization is specific to probe from sample 2, a red spot will result; if hybridization occurs for probe molecules that are found in both samples, the color will vary dependent upon relative abundance of the amplified probe, and also the target, in each sample (FIGS. 12A and 12B). FIG. 12C shows the results for this type of experiment for two lake samples amplified by PCR to generate either 16S probes (top panel) or 18S probes (bottom panel). In an embodiment, there may be at least one position per array for a known sequence that serves as a control to allow for orientation of the array (e.g., green spots in lower right hand position of each grid in FIG. 12C).

Figure 13:
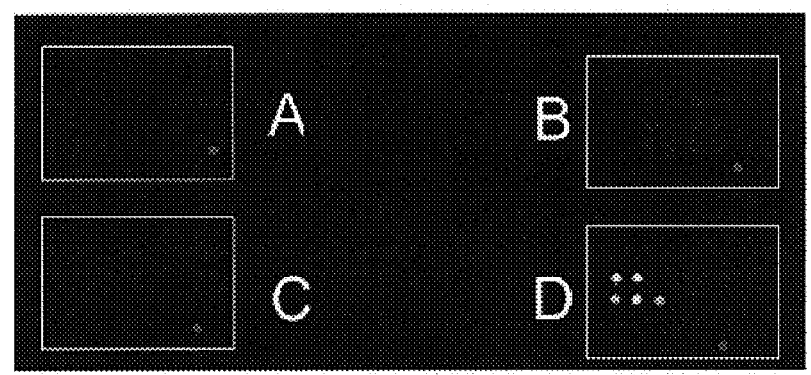
FIG. 13 shows an array that contains cyanobacteria sequences probed with amplification products generated using cyanobacteria multiplex primers from two water samples (one sample labeled in green and one sample labeled in red) that each contained cyanobacteria in accordance with an embodiment of the present invention, where oligonucleotide probes to 18S rDNA are spotted in Grid A and B, probes to 16S rDNA of *Escherichia coli* are spotted in Grid C, and twenty-one 16S rDNA probes containing cyanobacteria sequences, sequences associated with arsenic-responsive microbes, and other sequences identified in collected lake samples, are spotted in Grid D.

As described herein, the array may also be used to determine how chemical additions to water (e.g. cadmium, atrazine, perchlorate) may change the microbial community, and/or to detect known water pathogens. For example, the microarray may include 16S rDNA sequences from several known pathogens. FIG. 13 shows results for such an experiment, where multiplex PCR amplification and direct labeling of cyanobacteria present in a water sample are detected using cyanobacterial sequences on the array (Panel 13D).

Figure 14:
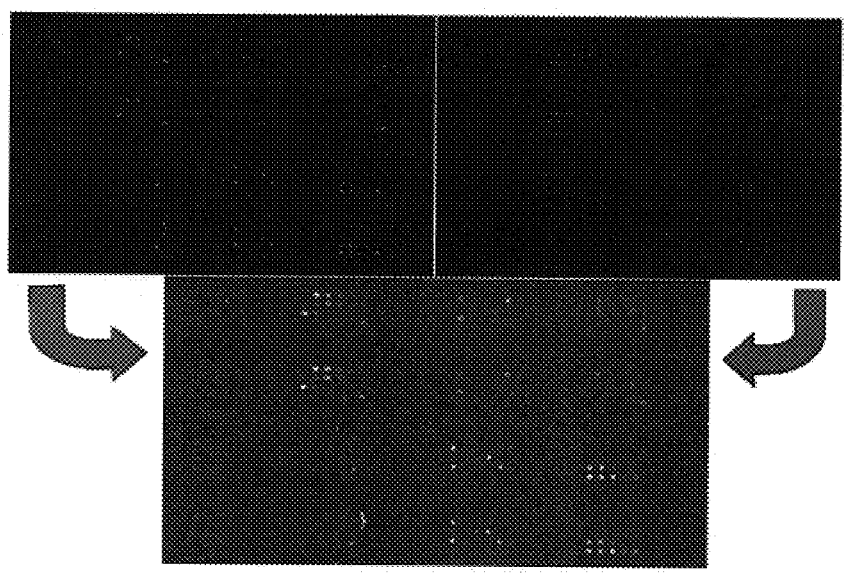
FIG. 14 shows hybridization of two samples to an array, where multiplex PCR reactions for both samples were identical and reaction products were either labeled with a red dye (Cy5) or a green dye (Cy3), allowing comparison of samples in accordance with an embodiment of the present invention. Shown are results from a test of two lake samples used to hybridize first singly (top panels) (left panel: Cy3-labeled sample; right panel: Cy5-labeled sample) and then together (bottom panel) to the same array of 105 oligonucleotide probes. The array is partitioned into duplicates of eight grids.

In one embodiment, an array of oligonucleotides that are isolated from known and unknown OTUs may be prepared. As used herein, known OTUs comprise sequences that are $\geq 97.5\%$ identical to sequences that have been reported in public databases, whereas unknown OTUs comprise sequences that do not meet this criterion and are believed to represent as yet unknown organisms. FIG. 14 shows an array comprising 105 olignonucleotides isolated from predetermined known and unknown freshwater lake OTUs probed with amplified DNAs from two different lake samples, where multiplex PCR reactions of each sample were identical and products each reaction were either labeled with a red dye (Cy5) or a green dye (Cy3), allowing comparison of samples. Shown are results from a test of two lake samples used to hybridize first singly (top panels) (left panel: green probe, sample 1; right panel: red probe, sample 2) and then together (bottom panel) to the same array of 105 oligonucleotide probes.

Such taxon-specific arrays may be used to detect microbes that are known to be characteristic of a particular type of water system. For example, in one embodiment, the array may be formulated to detect microbes common to fresh water systems. Or, the array may be formulated to detect microbes common to marshlands or small tidal pools. Or, arrays having nucleic acids derived from estuary water samples may be used to analyze water from various estuaries. The development of an array that utilizes freshwater nucleotide sequences is described in the Examples, below.

EXAMPLES

Example 1

Materials and Methods

Sample collection and DNA extraction. To develop probes for an array, three lakes were sampled: Lake Townsend (LT) (Greensboro, N.C.); City Lake (CL) (High Point, N.C.); and Toolik Lake (T L) (Alaska). Lake Townsend and City Lake are temperate mesotrophic and eutrophic municipal drinking water reservoirs, respectively. Toolik Lake is a highly oligotrophic, glacial lake located in the Arctic Long Term Ecological Research Site above the Arctic Circle in Alaska (Moon-van der Staay, S. Y., et al., 2001, *Nature*, 409: 607–610).

Five samples of surface water were collected: (1) LT-1J—at an open water location in Lake Townsend (station 1), depth=8.3 m, on Jun. 14, 2000; (2) LT-2J—at a shallow, near shore location in Lake Townsend (station 2), depth=1.3 m, on Jun. 14, 2000; (3) LT-1M—at station 1 of Lake Townsend, on Mar. 28, 2001; (4) CL—at an artificially aerated location in City Lake near a subsurface water treatment system intake on May 22, 2001; and (5) TL—at a location near the main LTER sampling station in Toolik Lake on Aug. 11, 2000. Each sample (~100 ml) was drawn through GF/C and GF/F glass fiber filters that were placed in cetyltrimethylammonium bromide (CTAB) buffer for storage at room temperature until later DNA extraction. Other lake samples, such as water samples from lakes that may be diagnostic of deformities found in members of the ecosystem may be used. For example, tests have been conducted using a group of North Dakota lakes that were paired according to geographical proximity. Each pair of lakes includes one lake that has been associated with a high level of frog deformities and one lake that has not been associated with any known deformities in frogs or any other organism. Samples from the lakes were used to isolate DNA for array analysis to ascertain microbial bioindicators associated with conditions leading to such deformities.

Genomic DNA was extracted from each water sample using a CTAB (cetyltrimethylammonium bromide) buffer DNA isolation technique (Rublee, P. A., et al., 1999, *Va. J Sci.*, 50:325–335). Briefly, the glass fiber filter was macerated in 2 ml CTAB in a 15 ml polypropylene conical tube using a sterile wooden applicator stick. After heating for 1 hr at 65° C., the mixture was extracted with 2 ml 24:1 (v/v) chloroform-isoamyl alcohol, and the DNA isolated from the aqueous portion by precipitation with 0.7 volumes 100% 2-propanol. The precipitate was pelleted, air-dried, and the DNA rehydrated in 25 µl TE buffer (pH 7.4) and stored at −20° C.

PCR amplification of genomic DNA from water samples for cloning rDNAs. SSU rDNA was amplified by PCR using prokaryotic-specific and eukaryotic-specific forward and reverse primers in 50 µl reactions (Table 1). Using the appropriate primer pairs, separate reactions were prepared for 16S rDNA and 18S rDNA. The amplification reactions consisted of: 5 µl 10× PCR Buffer; 5 µl Promega 25 mM MgCl$_2$; 5 µl 100 mM BSA; 2.5 µl 16 mM dNTP stock (4 mM each of dATP, dCTP, dGTP and dTTP); 1 µl each of 10 µM forward and reverse primers; 1 U Taq DNA Polymerase; 30.2 µl sterile deionized H$_2$O; and 1 µl genomic DNA. An MJ Research PTC-100 Programmable Thermal Controller was used to amplify samples under the following conditions: 2 min initial denaturation at 94° C.; 30 cycles of 1 min denaturation at 94° C.; 1 min annealing at 56° C. for 16S primers or 58° C. for 18S primers; and 2 min extension at 72° C.; 5 min final extension at 72° C. PCR products were verified by gel electrophoresis.

Cloning and sequencing of amplified PCR products. Purified PCR products were subcloned in plasmid vectors using the Invitrogen TOPO TA Cloning Kit according to the manufacturer's protocol. Ligation reaction mixtures were then used to transform TOP10 Chemically Competent *E. coli* cells and recombinant plasmids were identified by growth of bacterial colonies on LB agar plates containing 50 µg/ml ampicillin. Individual colonies from each plating were inoculated into LB liquid medium containing 50 µg/ml ampicillin and grown overnight with antibiotic selection. Inserts were purified from cultures using a QIAGEN QIAprep Spin Miniprep Kit according to the manufacturer's protocol. After removal of the insert, gel electrophoresis was used to verify the presence of a DNA fragment corresponding in size to 16S rDNA or 18S rDNA.

Fifty verified clones from each library were sequenced using a LI-COR Global Edition IR$^2$ System for automated DNA sequencing. Sequencing reactions were prepared using an Epicentre Technologies SequiTherm EXCEL™ II DNA Sequencing Kit-LC (for 25–41 cm gels) according to the Cycle Sequencing Protocol provided. Sequencing reactions included: 3.5× SequiTherm EXCEL™ II Sequencing Buffer; fluorescent (IR)-labeled M13–20 forward and reverse primers; purified cloned 16S rDNA or 18S rDNA; sterile deionized H$_2$O; SequiTherm EXCEL II DNA Polymerase; and SequiTherm EXCEL II-LC Termination Mixes A, C, G and T (each containing dATP, dCTP, dTTP, 7-deaza-dGTP, and one ddNTP). Using an MJ Research PTC-100 Programmable Thermal Controller, reactions were amplified by PCR using the following conditions: 4.5 min initial denaturation at 95° C., followed by 30 cycles of 30 sec denaturation at 95° C., 30 sec annealing at 51° C., and 1 min extension at 70° C. After amplification, Stop/Loading Buffer was added to reaction products, which were denatured for 5 min at 95° C. and loaded into a 41 cm polyacrylamide gel. During electrophoresis of reaction products, dual 700 and 800 nm detection channels were used for simultaneous bidirectional sequencing of each clone and sequence read lengths were at least 550 bp in each direction.

Sequence Alignments and Community Analyses. It is generally accepted in the art that 1000 nucleotides of sequence information is sufficient for even a detailed phylogenetic analysis (Oldach, D. W., et al., 2000, *Proc. Natl Acad. Sci., U.S.A.* 97:4303–4308). Thus, partial sequences were obtained for each clone and the first 500 nucleotides from both 5' and 3' ends. The use of 1000 nucleotides for phylogenetic ordering of the sequences was subsequently verified by generating complete sequences for 18S rDNA clones, with no improvement in the data (results not shown). After checking each sequence for the presence of chimeric properties using the program CHIMERA_CHECK (version 2.7; Ribosomal Database Project II, Center for Microbial Ecology, Michigan State University, available on-line), one sequence was excluded. The remaining sequences were submitted to the National Center for Biotechnology Information website for BLAST analysis (Altschul, S. F., et al., 1990, *J. Mol. Biol.*, 215:403–410).

Sequence alignments and analyses were performed using the BioEdit Sequence Alignment Editor and Analysis software (version 5.0.9; Department of Microbiology, North Carolina State University, available on-line), which includes CLUSTAL W as an accessory application for multiple alignments. Libraries were compared in pairwise fashion by combining and aligning two libraries at a time (100 sequences of 16S rDNA or 18S rDNA). Libraries were also merged into one group for alignment and comparison (249 16S rDNA sequences or 250 18S rDNA sequences).

Taxonomic classifications were based on identity matrices generated using an analysis tool incorporated into BioEdit. Sequences having identity scores of 0.975 or greater were considered to be sufficiently similar to group them into the same operational taxonomic unit (OTU). After grouping clones into OTUs, several diversity indices were calculated for each library. These included: (1) species richness, or total number of OTUs; (2) Simpson's dominance index, used to describe the distribution of clones among OTUs, or evenness; and (3) the Shannon-Wiener index, which serves as a statistical measure of the probability of correctly guessing the OTU identity of a randomly selected clone (Colinvaux, P. 1993. Ecology 2. John Wiley & Sons, Inc., New York, U.S.A). In addition, Sorensen coefficients (Lemke, M. J., et al., 1997, *Microb. Ecol.*, 34:224–231) were calculated to measure the similarity in species composition between two communities, or the proportion of OTUs shared between two libraries.

Also estimated was total species richness (S) using four methods based on the distribution of OTUs within a library. These included: Scov, an estimate based on "coverage" (Finlay, B. J., 2002, *Science*, 296:1061–1063; Giovannoni, S. J., et al., 1990, *Nature*, 345:60–63); Smax, an estimate based on rarefaction analysis (Haldeman, D. L., et al, 1994, *Appl. Environ. Microbiol.*, 60:2697–2703; Methe, B. A., and J. P. Zehr, 1999, *Hydrobiologia*, 401 :77–96), which was performed using the program Analytic Rarefaction (version 1.3; Stratigraphy Lab, University of Georgia, available on-line); and SACE and SChao 1, two estimates that were evaluated using a form processor and spreadsheet available through a web-based interface (ASLO, Limnology and Oceanography Methods, available on-line).

Phylogenetic analyses were conducted to assess molecular evolutionary relationships using MEGA software (version 2.1; Molecular Evolutionary Genetics Analysis, available on-line). All phylogenetic analyses are sensitive to alignment methods, assumptions regarding mutational rates, and the types and amount of sequence data used (Troesch, A., et al., 1999, *J. Clin. Microbiol.*, 37:49–55.). Trees were constructed using the Unweighted Pair-Group Method with Arithmetic Mean (UPGMA) and distances were estimated according to the Kimura 2-parameter model for nucleotide exchange with a transition/transversion ratio of 2.0 (Hurlbert, S. H., 1971, *Ecology* 52:577–586).

Real-time Quantitative PCR. Real-time Quantitative PCR (Q-PCR) experiments were designed to analyze the relative abundance of two 16S rDNA OTUs and one 18S rDNA OTU in three different samples using a Cepheid Smart Cycler system. The presence and accumulation of fluorescence bound to each target OTU was measured directly and compared among LT-1J, LT-1M and CL. Individual 25 µl reactions included: 2.5 µl Takara 10× Ex Taq Buffer; 1.25 µl Takara dNTP Mixture (2.5 mM each); 1.25 µl SYBR®

Green I nucleic acid gel stain (10×); 0.25 µl Takara Ex Taq™; 1 µl OTU-specific forward and reverse primers (10 µM each); 16.75 µl sterile deionized H$_2$O; and 1 µl experimental template (genomic DNA sample —0.025 µg/µl), positive control (mixed clone standard—25 pg/µl each), or negative control (sterile deionized H$_2$O). The mixed clone standard was prepared by combining three clones representing three experimental samples used in the experiment (i.e., genomic DNA samples from three different OTUs). Relative abundance estimates were calculated using a 1:10 dilution series of the mixed clone standard to determine cycle number differences between 25 pg, 2.5 pg, 0.25 pg, and 0.025 pg template concentrations.

Multiplex PCR of probes for array. To generate the target sequences used for hybridization to the array, a multiplex PCR amplification using at least 45 primer pairs developed from an analysis of individual OTUs, may be performed. The sequences of the eukaryotic primers and associated 50-mer probes are shown in Table 2. The sequences of the prokaryotic primers and associated 50-mer probes are shown in Table 3.

The conditions for multiplex PCR are as follows. Multiplexed PCR reactions containing ~250 ng genomic DNA are prepared in 0.5 ml thin-walled microcentrifuge tubes. The final reaction volume is 50 µl and contains a 200 nM final concentration of each primer, 5 µl 10× buffer, 5 µl BSA, 5 µl dNTPs, 1.25 U Taq, and sd H$_2$O (remaining volume). Reactions are placed in a programmable thermal controller and DNA amplification by PCR is carried out under the following conditions: initial denaturation at 94° C. for 2 minutes; 30 cycles of denaturation at 94° C. for 1 minute, annealing at 1 to 3 degrees below lowest primer T$_m$, extension at 72° C. for 1 minute; final extension at 72° C. for 1 minute; and storage at 4° C. of reaction product until use. The dNTP mixture is prepared by adding 16.6 µl sd H$_2$O to 2 µl 50× dNTP stock solution for an 8.33-fold dilution, where 50× dNTP stock solution is 10 µl each 100 mM dATP, dGTP, dCTP; 8 µl 100 mM amino allyl-dUTP; and 2 µl 100 mM dTTP.

The PCR products may, in some cases, be labeled using fluorescent dyes. The PCR product is transferred to a 1.5 ml microcentrifuge tube and 5 µl 3 M sodium acetate and 500 µl 100% ethanol are added. The contents are thoroughly mixed and stored overnight at −70° C. The samples are removed from −70° C. storage and spun in a microcentrifuge at 14,000 rpm for 20 minutes. After pouring off the supernatant, 500 µl 70% ethanol is added to wash the DNA pellet and this mixture is microcentrifuged at 14,000 rpm for 10 minutes. The supernatant is again poured off, the tube is allowed to air dry to remove all ethanol, and the pellet is then resuspended in 15 µl nuclease-free H$_2$O. The Cy dyes are removed from −20° C. storage and resuspended in 15 µl 0.1 M sodium bicarbonate, pH 9.0. The Cy dye and DNA resuspensions are combined, mixed well, and allowed to incubate for 1 hr at room temperature in the dark. To quench any unbound Cy dye after the dye coupling reaction, 15 µl 4 M hydroxylamine are added to each sample and these are incubated for 15 minutes at room temperature in the dark. Labeled samples are then purified using a PCR purification kit according to the manufacturer's protocol.

Spotting of oligonucleotides on the array. To immobilize nucleic acids on the array the following protocol was used. Each 50-mer oligonucleotide to be used as a probe sequence (i.e., sequences corresponding to SEQ ID NOS: 5–113 or the complement of these sequences) on the array is diluted 1:10 with 3×SSC/0.1% sarkosyl in a 96-well microplate for a final oligonucleotide concentration of ~250 ng/µl. Epoxy-coated slides are secured in slide positions of arrayer for printing. After the oligonucleotides are printed, the slides are UV cross-linked at 60 mJoules, baked at 80° C. in an oven for 2 hours, and stored at room temperature. The 3×SSC is prepared using a 20×SSC concentrate containing 3 M NaCl and 0.3 M sodium citrate, pH 7.0.

Hybridization of DNA sample to array. After purification, the Cy3 and Cy5-labeled sample eluates may be combined and lyophilized until almost dry, leaving approximately 5–10 µl behind. The sample may be resuspended using 80 µl Roche DIG Easy Hyb hybridization buffer and a clean lifterslip is placed on the microarray being used. The sample is heated at 95° C. for 2 minutes, cooled on ice for 1 minute, spun down to collect any condensation, and pipetted under the lifterslip. Next, the microarray is sealed within a hybridization cassette using the cassette lid and placed into a 45–55° C. water bath overnight. The next morning, three wash solutions are heated to 37° C., the hybridization cassette is removed from the water bath, and the microarray is removed from the cassette. The microarray with lifterslip is gently dipped into a staining dish containing wash buffer #1 (1×SSC, 0.1% SDS), to release the lifterslip. The microarray is then placed in a staining dish cassette and gently washed in wash buffer #1 for 5 minutes. Using the same technique, the microarray is next washed in wash buffer #2 (1×SSC), for 5 minutes. Finally, the microarray is washed in wash buffer #3 (0.05×SSC), by gently dipping it 5–10 times. The microarray is removed from the staining dish cassette and tapped on edge against the benchtop to remove all solution droplets. Once dry, the microarray is scanned.

Example 2

Grouping rDNAs into Operational Taxonomic Units

Analysis of Clones. Approximately 50 prokaryotic rDNA and 50 eukaryotic rDNA clones for each of the five lake samples (500 rDNA sequences) were sequenced through a 1700 bp segment of the eukaryotic 18S rDNA, or a 1540 bp segment of the prokaryotic 16S rDNA, to provide for phylogenetic classification of known and novel species (Pace et al., 1986, *Adv. Microb. Ecol.*, 9:1–55; Sogin and Gunderson, 1987, *Annals. NY Acad. Sci.*, 503:125–139). Based on the rDNA sequencing alignments, a level of 97.5% sequence identity was the criterion by which rDNAs were placed in the same operational taxonomic unit (OTU). Because multiple small subunit rDNA copies may reside within a species genome (Farrelly et al., 1995, *Appl. Environ. Microbiol.*, 61:2798–2801), a 97.5% level of sequence identity allows for the possibility that a different sequence in the same species was recovered. A software program (CHIMERA-CHECK; Kopzcysnski et al., 1994, *Appl. Environ. Microbiol.*, 60:746–748; Wang and Wang, 1995, *Appl. Environ. Microbiol.*, 63:4645–4650; Qui et al, 2001, *App. Environ. Microbiol.*, 58:2717–2722) was also employed to reduce the possibility of misidentifying a chimeric rDNA as an unique clone.

For each sample, libraries of SSU rDNA clones were produced, individual clones were sampled, sequences for each clone were generated, and standard diversity statistics were computed (Table 4). Based on a comparative analysis of all prokaryotic (16S) rDNA sequences, it was determined that 49 OTUs contained multiple sequences and that 62 OTUs were unique, each containing a single sequence. An analysis of all eukaryotic (18S) sequences resulted in 42 OTUs containing multiple sequences and 67 unique OTUs.

TABLE 4

Comparison of prokaryotic and eukaryotic diversity

|  | LT-1J | | LT-2J | | LT-1M | | CL | | TL | |
|---|---|---|---|---|---|---|---|---|---|---|
| rDNA library | 16S | 18S | 16S | 18S | 16S | 18S | 16S | 18S | 16S | 18S |
| Number of clones | 50 | 50 | 50 | 50 | 50 | 50 | 49 | 50 | 50 | 50 |
| Number of OTUs | 33 | 31 | 31 | 32 | 26 | 34 | 28 | 28 | 23 | 12 |
| Evenness | 0.039 | 0.049 | 0.050 | 0.053 | 0.089 | 0.043 | 0.079 | 0.102 | 0.078 | 0.358 |
| Shannon-Wiener index | 3.38 | 3.24 | 3.24 | 3.24 | 2.84 | 3.35 | 3.00 | 2.90 | 2.86 | 1.62 |

LT-1J: Lake Townsend, station 1, June;
LT-2J: Lake Townsend, station 2, June;
LT-1M: Lake Townsend, station 1, March;
CL: City Lake;
TL: Toolik Lake.

Species Diversity Measures. Prokaryotic and eukaryotic species richness, evenness, and the Shannon-Wiener index differed among lakes. In general, Lake Townsend, NC, contained more species and showed the most even distribution of species; consequently, its Shannon-Wiener index values were the highest. In contrast, Toolik Lake, AK, had the lowest richness estimates, especially for eukaryotes, indicating that species diversity was much lower here than in the temperate lakes and that a few successful competitors dominated the arctic community.

As a first indication of diversity, various statistical measurements of the recovered sequences were made to determine the species coverage, species evenness (Simpson's Index of Dominance; Colinvaux, 1993, *Ecology* 2, John Wiley & Sons, Inc. New York, N.Y.), species richness (the number of recovered species in a sample), species diversity (Shannon-Wiener index; Nubel et al., 1999, *Appl. Environ. Microbiol.*, 65:422–430) and the estimated proportion of shared OTUs between samples (Sorenson similarity coefficient; Lincoln et al, 1998, *A Dictionary of Ecology, Evolution, and Systematics*, Cambridge University Press, New York, N.Y.; McCaig et al., 1999, *Appl. Environ. Microbiol.*, 65:1721–1730). Coverage estimates of the percentage of OTUs recovered from a source were based on the relative abundance of the clones already obtained, and indicated that 48 to 76% of the prokaryotic rDNAs, and between 48 and 90% of the eukaryotic rDNAs, had been recovered from the samples. The highest coverage (i.e., 90%) was for Toolik Lake; apparently caused by the high level of recovery of a single rDNA. Not unexpectedly, the species evenness and richness was about the same for all the North Carolina lake samples, but the distribution of recovered species was much more skewed and lower in Toolik Lake, Alaska. To generate a nucleic acid array for monitoring water, however, the purpose of the census is not necessarily to identify all the microbial species that exist in these samples, but rather to survey water sources for relatively common microbes whose appearance and abundance can be monitored on a microarray platform.

Rank-abundance curves (FIGS. 2 and 3) for most samples showed that a few taxa were abundant and that many taxa were represented by a single clone. It is highly likely that the samples also contain several other clones at low frequencies. In Toolik Lake, fewer species were detected and these were more abundant relative to the other lakes tested, implying that Toolik Lale contained a smaller number of species. This was supported by the estimates of total taxonomic diversity using the four methods described above (Table 5).

TABLE 5

Estimates of species richness (S) for each prokaryotic and eukaryotic community

|  | LT-1J | | LT-2J | | LT-1M | | CL | | TL | |
|---|---|---|---|---|---|---|---|---|---|---|
| rDNA library | 16S | 18S | 16S | 18S | 16S | 18S | 16S | 18S | 16S | 18S |
| Number of OTUs | 33 | 31 | 31 | 32 | 26 | 34 | 28 | 28 | 23 | 12 |
| Scov | 57 | 56 | 54 | 62 | 44 | 71 | 46 | 47 | 29 | 14 |
| $S_{max}$ | 93 | 72 | 73 | 74 | 40 | 93 | 53 | 47 | 40 | 12 |
| SACE | 61 | 80 | 77 | 110 | 110 | 106 | 67 | 65 | 38 | 17 |
| SChaol | 54 | 77 | 63 | 88 | 91 | 99 | 54 | 60 | 28 | 14 |

LT-1J: Lake Townsend, station 1, June;
LT-2J: Lake Townsend, station 2, June;
LT-1M: Lake Townsend, station 1, March;
CL: City Lake;
TL: Toolik Lake.

Sequence Identifications and Library Comparisons. Clone sequences were submitted for BLAST analysis to assess phylogenetic affiliations with reported sequences in the GenBank database. Sequence alignments having $\geq 97.5\%$ identity were used to propose OTU identifications and determine the proportion of known OTUs for each library (Table 6). The Lake Townsend March sample contained the lowest average proportion of known OTUs (24.8%), while Toolik Lake had the highest (43.0%). Identifications for clones within the same OTU were consistent, suggesting that a 97.5% identity threshold grouped individuals at the species level.

TABLE 6

Summary of prokaryotic and eukaryotic OTUs

| rDNA library | LT-1J | | LT-2J | | LT-1M | | CL | | TL | |
|---|---|---|---|---|---|---|---|---|---|---|
| | 16S | 18S | 16S | 18S | 16S | 18S | 16S | 18S | 16S | 18S |
| No. known clones | 21 | 17 | 16 | 21 | 21 | 19 | 31 | 20 | 25 | 32 |
| Proportion known OTUs (%) | 12/33 (36.4) | 8/31 (25.8) | 10/31 (32.3) | 8/32 (25.0) | 6/26 (23.1) | 9/34 (26.5) | 13/28 (46.4) | 6/28 (21.4) | 14/23 (60.9) | 3/12 (25.0) |

LT-1J: Lake Townsend, station 1, June;
LT-2J: Lake Townsend, station 2, June;
LT-1M: Lake Townsend, station 1, March;
CL: City Lake;
TL: Toolik Lake.
Number of known OTUs = number of OTUs with clones having ≧97.5% sequence similarity to GenBank entries.
Known clones refer to clones whose sequences correspond to known microbial species or unidentified species in the GenBank database.

Samples having similar estimates of species diversity were distinguished by differences in community composition. For instance, 8 eukaryotic OTUs were identified in each Lake Townsend sample, but the species composition of this group varied between samples. Comparing only the OTUs with multiple sequences, the following observations were made: LT-1J species included *Chilomonas paramecium*, *Cryptomonas ovata*, and *Geminigera cryophila*; LT-2J species included *Brachionus plicatilis*, *Cryptomonas ovata*, *Didinium nasutum*, and *Dileptus* sp., and the LT-1M species included *Cryptomonas ovata* and *Tabularia tabulata*. A comparison of the unique OTUs distinguished these samples even more.

Based on sequence alignments and comparisons that included all OTUs, phylogenetic trees were generated according to the UPGMA method to show the overall distribution of OTUs among the five samples. The prokaryote tree in FIG. 4 was constructed using 111 different 16S rDNA OTUs, including 40 that are known rDNAs (about 36%). The eukaryote tree in FIG. 5 represents 109 18S rDNA OTUs and includes 22 known rDNA sequences (about 20%).

To determine which OTUs, if any, appeared in more than one library, the sequences from each library were compared to those in every other library in pairwise library comparisons and a similarity coefficient was calculated for each pairing (Table 7). Although no prokaryotic sequences were shared between LT-2J and TL, there was some overlap between every pair of samples and the degree of overlap varied considerably. In some comparisons, roughly equal proportions of prokaryotic and eukaryotic OTUs were shared, but other comparisons revealed different patterns.

TABLE 7

Sorensen coefficients for prokaryotic and eukaryotic sample comparisons

| rDNA library | LT-1J | | LT-2J | | LT-1M | | CL | | TL | |
|---|---|---|---|---|---|---|---|---|---|---|
| | 16S | 18S | 16S | 18S | 16S | 18S | 16S | 18S | 16S | 18S |
| LT-1J | 1 | 1 | 0.344 (11) | 0.159 (5) | 0.169 (5) | 0.215 (7) | 0.230 (7) | 0.068 (2) | 0.071 (2) | 0.093 (2) |
| LT-2J | | | 1 | 1 | 0.070 (2) | 0.061 (2) | 0.169 (5) | 0.133 (4) | 0 | 0.091 (2) |
| LT-1M | | | | | 1 | 1 | 0.074 (2) | 0.161 (5) | 0.122 (3) | 0.174 (4) |
| CL | | | | | | | 1 | 1 | 0.039 (1) | 0.200 (4) |
| TL | | | | | | | | | 1 | 1 |

Coefficients were calculated as follows: S = 2 × C/(A + B), where A and B represent the numbers of OTUs in libraries A and B, respectively, and C represents the number of OTUs shared by A and B (34, 40). ( ) indicate the number of OTUs that were shared by the paired libraries. LT-1J: Lake Townsend, station 1, June; LT-2J: Lake Townsend, station 2, June; LT-1M: Lake Townsend, station 1, March; CL: City Lake; TL: Toolik Lake.

Figure 6:
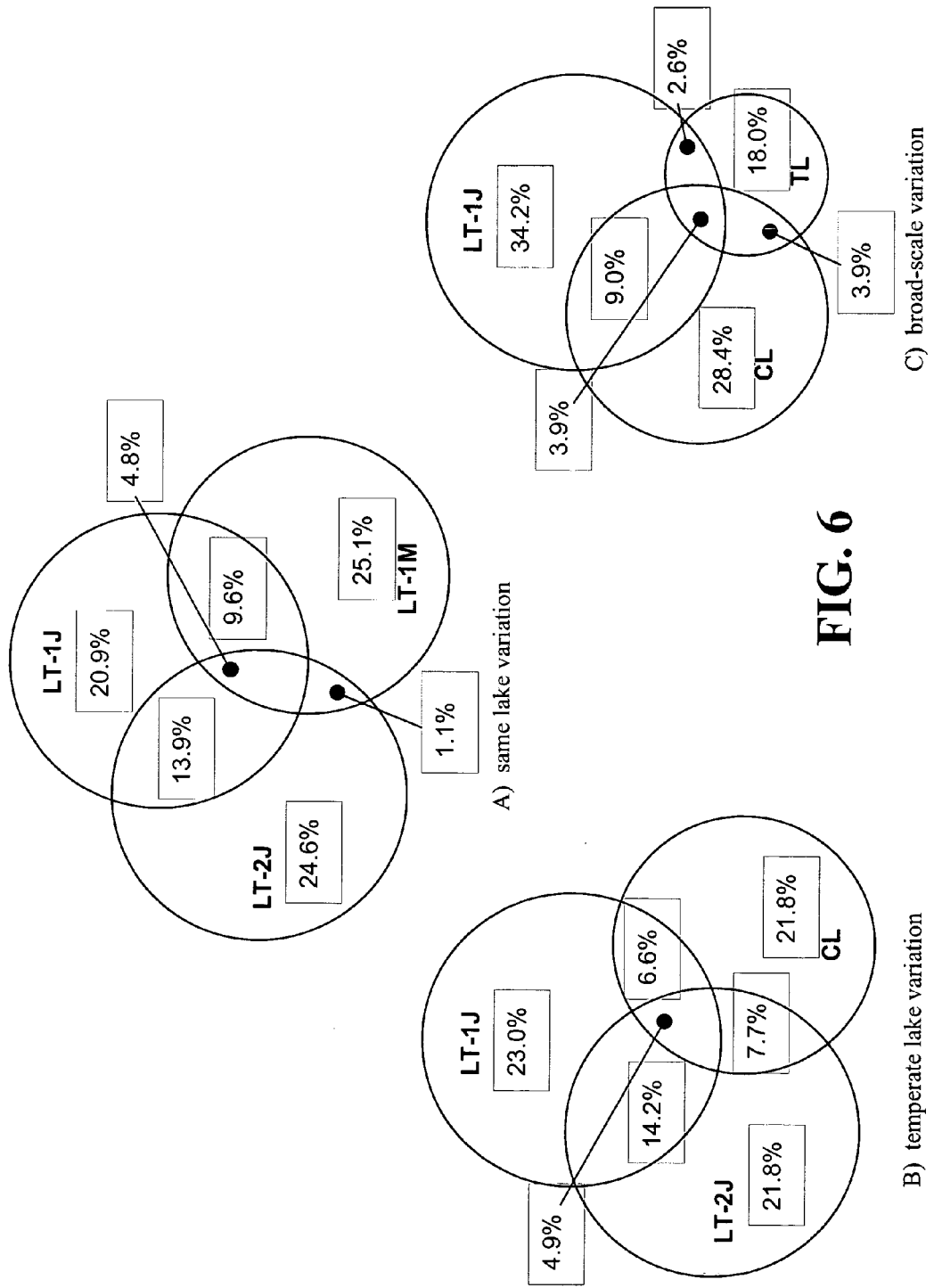
FIG. 6 shows Venn diagrams that illustrate the relative patterns of shared operational taxonomic units (OTUs) for five separate fresh water samples in accordance with an embodiment of the present invention. The size of each sample component is based on the total number of OTUs for that water sample relative to the other samples. Water samples from which the rDNA was isolated were as follows: LT-1J: Lake Townsend, station 1, June; LT-2J: Lake Townsend, station 2, June; LT-1M: Lake Townsend, station 1, March; CL: City Lake; TL: Toolik Lake.
Figure 7:
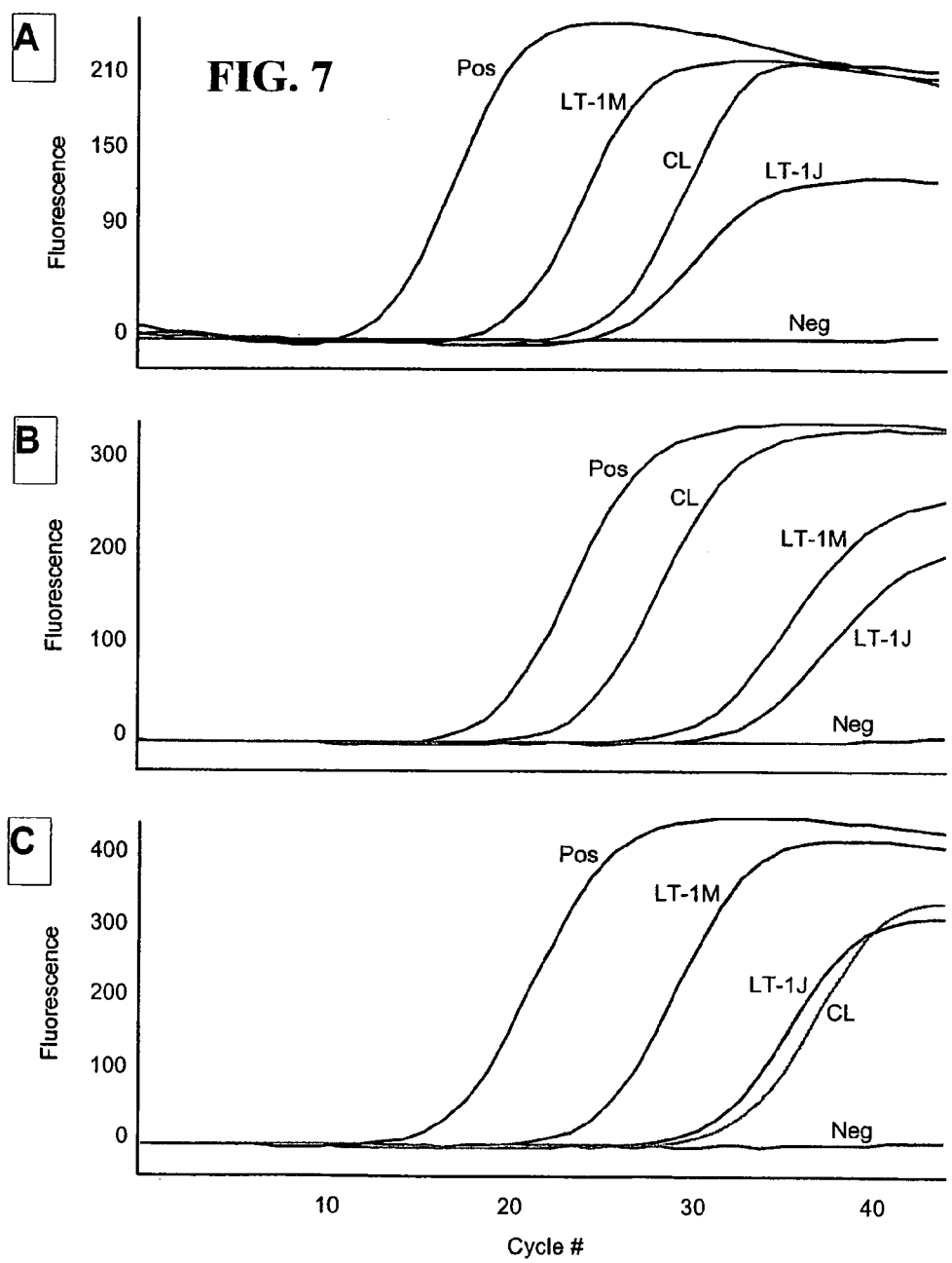
FIG. 7 shows quantitative PCR (Q-PCR) product accumulation curves generated using operational taxonomic unit (OTU)-specific primers and genomic DNA isolated from lake samples in accordance with an embodiment of the present invention where Panel (A) shows the relative abundance of the OTU for an unidentified cyanobacterium LD27 initially detected in Lake Townsend Station 1, March (LT-1M), panel (B) shows the relative abundance of OTU for *Zoogloea ramigera* initially detected in City Lake (CL), and panel (C) shows the relative abundance of OTU for *Asterionella formosa* initially detected in Lake Townsend Station 1, March (LT-1M). Pos: a positive control including a mixture of the three test DNAs; Neg: a negative control having no DNA; LT-1J: Lake Townsend, station 1, June; LT-1M: Lake Townsend, station 1, March; CL: City Lake.

Venn diagrams depict sample comparisons at different spatial and temporal scales (FIG. 6). In the fine-scale spatial comparison of LT-1J and LT-2J, each shared OTU contained nearly equal numbers of sequences from both samples, except for two sequences that occurred four times as often in LT-2J. One of these, a 16S rDNA OTU, was not identified, while the other 18S rDNA OTU aligned with *Geminigera cryophila*, and was also found in Toolik Lake (three copies). Such unequal occurrences of an OTU between samples may signify a detectable difference in the relative abundance of this particular microbial population between samples. OTUs that consistently vary in frequency among samples are potential bioindicators. For instance, one new bacterial species and the *Geminigera cryophila* OTU appear to be more abundant in temperate lakes, especially pelagic waters.

Thus, it was found that for the five lake samples analyzed, 26 different eukaryotic OTUs were represented by multiple copies, including 11 that are associated with known species. Another 79 eukaryotic OTUs were obtained as single copy clones and almost all of these represent unidentified species (Marshall, 2002, Masters Thesis, University of North Carolina at Greensboro). Similarly, 45 different prokaryotic OTUs were found in multiple copies among the collection of samples, of which 10 are associated with a known species, and another 19 resemble reported sequences for as yet unidentified species. Another 92 single copy rDNA sequences, most from unidentified prokaryotes, were recovered from the samples (Amos, 2002, Masters Thesis, University of North Carolina at Greensboro). Both known and unidentified rDNA sequences may be used as probes printed on the assay matrix of the present invention.

The ability to assess environmental parameters of water quality may require a sufficient number of potential bioindicator species, but may also require sequences having sufficient similarity across samples to allow for some general application. As noted in Table 8, a diversity of microbial species may be readily retrievable from a single body of water for even an oligotrophic source such as Toolik Lake, Alaska. While every sample produced several unique OTUs, all of the lakes produced multiply represented OTUs, and the most common OTU in each sample accounted for 10% or more of all the rDNAs analyzed in each of the samples.

refer to rDNA sequences that were recovered and characterized only in the designated sample either as a single copy, referred to as a unique OTU, or in multiple copies. It can be seen that the distribution of some OTUs is broad, while for others it is more localized (Table 9), suggesting that many microbial species exist across a range of watersheds and that a general purpose DNA microarray, that may be used for multiple watersheds, may be developed. An example analysis of specific OTUs is shown in Table 10.

A preliminary analysis of rDNA sequences from paired North Dakota lake samples (where one lake sample that exhibits substantial deformities in the frog population and one lake sample does not) acquired from the Fargo, N. Dak. USDA station indicates that some of the OTUs for unknown species are shared with sequences found in North Carolina lakes. Moreover, preliminary real-time PCR experiments

TABLE 8

Relative abundance of eukaryotic and prokaryotic OTUs

|  | Most abundant OTU | | 2X OTUs | | 1X OTUs | | Total OTUs | |
| --- | --- | --- | --- | --- | --- | --- | --- | --- |
|  | Eukary. | Prokary. | Eukary. | Prokary. | Eukary. | Prokary. | Eukary. | Prokary. |
| LT-1J | 10% | 8% | 9 | 10 | 23 | 26 | 32 | 36 |
| LT-2J | 14% | 10% | 9 | 8 | 22 | 26 | 31 | 34 |
| LT-1M | 10% | 14% | 8 | 7 | 26 | 23 | 34 | 30 |
| CL | 14% | 22% | 10 | 9 | 21 | 22 | 31 | 31 |
| TL | 58% | 20% | 7 | 12 | 5 | 12 | 12 | 24 |

LT-1J; Townsend, NC; June, Station 1;
LT-2J; Townsend, NC; June, Station 2;
LT-1M, Townsend, NC; March, Station 1;
CL, City Lake, NC May;
TL, Toolik Lake, AK;

August. 2× represents OTUs with at least 2 members; 1× represents OTUs with only one member.

Table 9 shows the pattern of shared and unshared OTUs among the five freshwater lake samples. Unshared OTUs suggest that at least some microbes exist an endemic level in almost all freshwater lakes, suggesting that that relative abundance for these endemic microbes is primarily dictated by local water conditions.

TABLE 9

Shared and unshared OTUs among the five freshwater lake samples

|  | A | | B | | C | | D | | E | |
| --- | --- | --- | --- | --- | --- | --- | --- | --- | --- | --- |
|  | Euk. | Prok. | Euk. | Prok. | Euk. | Prok. | Euk. | Prok. | Euky. | Prok. |
| Unshared OTUs | 18 | 22 | 19 | 19 | 19 | 19 | 18 | 20 | 5 | 12 |
| OTUs in 2 samples only | 2 | 5 | 1 | 4 | 3 | 8 | 2 | 4 | 2 | 19 |
| Toolik only | 0 | 0 | 0 | 0 | 0 | 0 | 0 | 0 | — | — |
| Townsend only | 5 | 6 | 3 | 6 | 5 | 2 | — | — | — | — |
| Townsend or City | 2 | 2 | 1 | 3 | 2 | 1 | 5 | 6 | — | — |
| All lakes* | 4 | 0 | 3 | 0 | 5 | 0 | 5 | 0 | 5 | 0 |

*All lakes does not necessarily mean all samples.
A: Townsend, NC, June, Station 1;
B: Townsend, NC, June, Station 2;
C: Townsend, NC, March, Station 1;
D: City Lake, NC, May;
E, Toolik Lake, AK, August
Euk = Eukaryotic;
Prok = Prokaryotic

TABLE 10

Relative abundance of five eukaryotic rDNA species found in all three sampled lakes

|  | A | B | C | D | E |
|---|---|---|---|---|---|
| *Cryptomonas ovata* | 30% | 12% | 20% | 30% | 8% |
| Unidentified 18s rDNA-1 | 0% | 0% | 10% | 6% | 58% |
| *Ochromonas tuberculata* | 12% | 6% | 6% | 8% | 4% |
| *Oxytricha longa* | 2% | 10% | 2% | 8% | 10% |
| Unidentified 18s rDNA-2 | 10% | 0% | 4% | 2% | 10% |

A: Townsend, NC, June, Station 1;
B: Townsend, NC, June, Station 2;
C: Townsend, NC, March, Station 1;
D: City Lake, NC, May,
E: Toolik Lake, AK, August Library Screening vs. Real-time Q-PCR. Several OTUs may be found at quantitatively different levels in different ecosystems. Three OTUs that appeared to be recovered differentially from one water sample were used in fluorescence detection real-time PCR experiments to determine if they were also present in other water samples (FIG. 7). It was found that each of the test OTUs was in fact present in all of the samples investigated. Panels (7A) and (7C) show the detection of two OTUs that appeared in LT-1M clone libraries at frequencies of 10 and four copies (out of 50), respectively. The OTU in panel (7B) was originally recovered from a City Lake library (11 copies of 50).

The relative abundance of each OTU was compared and estimated across the same three samples based on a dilution series of a known standard (data not shown). According to cycle threshold differences between growth curves in FIG. 7A, the amount of product in the LT-1M sample was estimated to be 34 times greater than the amount of this product in LT-1J and 13 times greater than the amount in CL. For the experiment shown in FIG. 7B, it was found that the amount of product in CL was about 219 times greater than that found in LT-1J and 41× greater than that found in LT-1M. For the experiment shown in FIG. 7C, it was found that the amount of product in LT-1M was about 29 times more abundant than in LT-1J and 55 times more abundant than in CL.

Real-time PCR assays also allowed for an estimation of the sensitivity of rDNA amplification for detecting community members. Based on four completed *E. coli* genomes from GenBank entries AE014075 (Venter, J. C., et al., 2004, *Science*, 304:66–74), U00096 (Blattner, F. R., et al., 1997, *Science*, 277:1453–1474), BA000007 (Lincoln, R., G. Boxshall, and P. Clark, 1998, A Dictionary of Ecology, Evolution and Systematics. Cambridge University Press, New York, N.Y.), and AE005174 (Pace, N. R., et al., 1986, *Adv. Microb. Ecol.*, 9:1–55), it was estimated that 16S rDNA makes up about 0.206% of the *E. coli* genome, and therefore, about 52 pg of 16S rDNA should be present in 25 ng of genomic DNA material. Experiments indicated that Q-PCR detected a specific rDNA signal from as little as $3.6 \times 10^{-3}$ pg of genomic DNA, based on a comparison with the Q-PCR signal evoked by individual rDNA clones, indicating that clones occurring at a frequency as low as $6.9 \times 10^{-5}$ should be detectable by Q-PCR, and that a sampling of $14.5 \times 10^3$ clones would be required for a mean recovery of one target clone. Assuming a Poisson distribution of clones in a library, it was estimated that to ensure the recovery of any one clone at a probability of greater than 99%, a library screening method would require $66.7 \times 10^3$ clones.

Generally, the results indicated that the Toolik Lake microbial community differs more from the North Carolina lakes than the North Carolina lake communities differ from each other. The three Lake Townsend samples also showed variation as the samples differed with respect to the location and season of sampling. While the March and June collections at the same Lake Townsend location shared several OTUs with the other Lake Townsend and City lake samples, several multiple-copy OTUs were only found in the March collection, indicating that some microbial species thrive in the relatively cold waters of early Spring. Also, the two Lake Townsend samples collected on the same day showed the highest level of overall similarity. The library sampling method was able to detect similarities between samples, indicating that the microbial community is not too heterogeneous to analyze with molecular methods. In addition, the existence of unshared OTUs and the ability to detect quantitative differences between shared OTUs indicated differences between microbial communities that may be diagnostic of specific environmental conditions.

Example 3

Qualitative and Quantitative Analysis of Water Samples Using Microarrays

Based on the sequence information provided by the clones and information available in GenBank, two microarrays for testing water samples were made. The protocol for testing the microarray was as follows: appropriate prokaryotic and eukaryotic primers were used to amplify either 16S rDNA or 18S rDNA, respectively, from DNA that was extracted from the water samples as described above. The PCR products were then labeled by chemical attachment to either Cy3 (green) or Cy5 (red) dye, and upon denaturation, the labeled PCR products were hybridized to the array.

To make the arrays, 50-mer oligonucleotide sequences were spotted onto the surface of epoxy-coated glass slides. In Table 11, sequence identifications from Tables 2 and 3 are provided for each probe that was spotted to make the array shown in FIGS. 11 and 12. As indicated, there were some locations at which no probes were spotted.

TABLE 11

| Prokaryotic (16S rDNA) probes | | | | | |
|---|---|---|---|---|---|
| 103P | | | 103P | | |
| 103P | 103P | 104P | 105P | 106P | 107P |
| 108P | 109P | 110P | 103F$_1$ | 103F$_1$* | 103F$_1$* Cy3 9mer |
| Eukaryotic (18S rDNA) probes | | | | | |
| 15P | 15P | 30P | 31P | 32P | 16P |
| 33P | 34P | 14P | 35P | 36P | 38P |
| 39P | 40P | 41P | 37P | 42F | 42F** Cy3 9mer |

*reverse complementary sequence of 103F$_1$;
**reverse complementary sequence of 42F The experimental design is illustrated in FIG. 11A, showing labeling of a subset of sequences (e.g., prokaryotic) with red dye (FIG. 11A-1) and labeling of a second subset of sequences (e.g., eukaryotic) with green dye (FIG. 11A-2). Aligned sequences were used to design taxon-specific PCR primers (20–26 mer) and oligonucleotide probes (50-mers) to complementary variable regions. As a printing control and orientation marker, a Cy3-labeled random 9-mer probe was also printed with each grouping of probes.

In the experiment shown in FIG. 11B, two aliquots drawn from a single genomic DNA sample (Lake Townsend, Station 1, June) were subjected to PCR with either a universal prokaryotic rDNA primer pair or a universal eukaryotic rDNA primer pair (Table 1) with dUTP added to the reaction mixture. The conditions for amplification were as described above for generation of the libraries. As described herein, the PCR reactions were then labeled with either Cy5 (red, prokaryotic), or Cy3 (green, eukaryotic) by chemically attaching the incorporated dUTP. The reactions were mixed and hybridized to a glass slide spotted with the oligonucleotide probes. As shown in FIG. 11B, the eukaryotic and prokaryotic PCR products are clearly detected on the prototype microarray. The scanned array image showed complete specificity of 12 of 12 prokaryotic probes and 19 of 21 eukaryotic probes. The green spot in the lower right of each sub-array was a Cy3-labeled 9-mer marker for orientation. Also, locations at which no spots appear were printed with probes for sequences that were not experimental targets, thus acting as negative controls and, indicating that there was minimal DNA carryover during the array printing process. The actual array carried three sets of each grid, and scanned images of the replicate grids produced substantially identical images.

The experiment illustrated in FIG. 12 illustrated that the microarray may be used as a semi-quantitative assessment to compare two samples (for instance, the same location within a lake at two different times), or a sample and a standard. In this approach, two multiplex PCR amplifications were run—one for each lake sample. Both 16S and 18S rDNA were amplified together in a single reaction, and the amplified products from each sample were then labeled with either the red (Sample 1) or green (Sample 2) dye. When the amplified products were hybridized to a microarray, any resulting signal varied in color from red (target found in only sample 1) to yellow (target in both samples) to green (target found only in sample 2). The continuum from red to green is indicative of the relative abundance of the target in the samples.

Example 4

Testing for Specific Pathogens

The microarray is also capable of detecting known water pathogens and contaminants which affect water quality, thus raising the possibility of an "all in one" testing system. To test the feasibility of this additional feature, a microarray including 16S rDNA sequences from several cyanobacteria species was made. This microarray was tested with primers designed to amplify the rDNA of these species specifically, and the labeled products were hybridized to the microarray. As FIG. 13 shows, the multiplex/direct labeling methodology resulted in the appearance of signals specific for the cyanobacterial sequences from water samples known to contain cyanobacteria. For the experiment shown in FIG. 13, oligonucleotide probes to 18S rDNA are spotted in Grid A (16 probes) and B (15 probes). Twelve probes to 16S rDNA of *Escherichia coli* (strains K12 and O157:H7; Prena et al, 2001, *Nature*, 409: 465–466) are spotted in Grid C, and twenty one 16S rDNA probes are spotted in Grid D, which contains cyanobacteria sequences, sequences associated with arsenic-responsive microbes (Oremland and Stolz, 2003, *Science* 300:939–943), and sequences identified in collected samples. Grids A, B, C, and D from FIG. 13 are shown in Table 12, and the identity of each probe (Tables 2 and 3) is provided at its location on the array

TABLE 12

Oligonucleotide probes on array of FIG. 13

A

| | | | | | |
|---|---|---|---|---|---|
| 15P | 30P | 31P | 32P | 16P | 33P |
| 34P | 14P | 35P | 36P | 38P | 39P |
| 40P | 41P | | | | |
| 17P | 29P | | | | Cy3 9mer |

B

| | | | | | |
|---|---|---|---|---|---|
| 10P | 11P | 12P | 13P | | |
| 19P | 20P | 21P | 22P | 18P | 23P |
| 24P | 25P | 26P | 27P | 28P | |
| | | | | | Cy3 9mer |

C

| | | | | | |
|---|---|---|---|---|---|
| 51P | 52P | 53P | 54P | 55P | 56P |
| 57P | 58P | 60P | 61P | 62P | 63P |
| | | | | | Cy3 9mer |

D

| | | | | | |
|---|---|---|---|---|---|
| 83P | 81P | 73P | 74P | 75P | 76P |
| 84P | 85P | 82P | 80P | | |
| 103P | 104P | 105P | 106P | 107P | 108P |
| 109P | 110P | 77P | 78P | 79P | Cy3 9mer |

To generate the labeled probe for this experiment, Toolik Lake, AK and City Lake, NC genomic samples were amplified using cyanobacteria specific PCR primers in a multiplex format. Toolik Lake products were labeled with Cy3 (green) and City Lake products were labeled with Cy5 (red). The primer pairs were: *Synechococcus.* sp. LBP1, *Synechococcus* sp. LBG2, an unknown cyanobacteria clone LD27, and a degenerate *Synechococcus* primer set (Table 3). The four probes to cyanobacteria hybridized with amplicons from both lake samples as evidenced by the yellow signal in grid D (FIG. 13). The additional signal in Grid D resulted from a labeled product that recognized a probe corresponding to the bacterium *Burkholderia cepacia* genomovar III. Subsequent analysis revealed that at least one of the *Synechococus* primers resembled the *B. cepacia* sequence, and that it likely amplified *B. cepacia* rDNA in the sample, indicating the importance of designing primer pairs to prevent cross-reactivity.

Example 5

Taxon-Specific Arrays

Amplification of genomic sample DNA may be performed by multiplex PCR using primers chosen to provide products that can hybridize to taxon-specific DNAs. Using this protocol can dramatically reduce non-specific labeling, and eliminates the need for intermediate PCR reactions, which reduce sensitivity.

FIG. 14 shows a taxon-specific array comprising 105 oligonucleotides generated from known and unknown OTUs isolated from freshwater lakes and from GenBank pathogen sequences. DNA samples from two different lakes were amplified in identical multiplex PCR reactions and reaction products were either labeled with a red dye (Cy5) or a green dye (Cy3), allowing for comparison of samples. Shown are results from a test of two lake samples used to hybridize first singly (top panels) (left panel: Cy3-labeled sample, sample 1; right panel: Cy5-labeled sample) and then together (bottom panel) to the same array of 105 oligonucleotide probes.

The arrays included nucleic acid sequences from variable regions of individual eukaryotic and prokaryotic rDNAs. Sequences spotted on the arrays included 32 probes derived from the literature that target known pathogens or contaminant microbes and 73 probes to sequences derived from freshwater environmental samples, including both known and novel sequences, and four cyanobacteria. The actual probe sequences spotted on the array shown in FIG. 14 are provided in Table 13, and the location of each sequence on the array is provided in Table 14.

TABLE 13

Primer/Probe combinations spotted on microarrays

| 16S rDNA sequence | GenBank accession no. | 18S rDNA sequence | GenBank accession no. |
|---|---|---|---|
| *Enterococcus gallinarum,* strain LMG 13129 | AJ301833 | *Cryptosporidium parvum* | AF222998 |
| *Burkholderia cepacia* | AB091761 | *Acanthamoeba mauritaniensis* | AY351647 |
| *Burkholderia cepacia* genomovar III | AF148556 | *Cyclospora cayetanensis* | AF111183 |
| Uncultured human fecal bacterium HF74 | AF233412 | *Entamoeba histolytica* | X65163 |
| Uncultured human fecal bacterium HF8 | AF233408 | *Giardia intestinalis* isolate | AF199449 |
| Uncultured human fecal bacterium HF10 | AF233413 | *Isospora belli* | AF106935 |
| *Bacillus anthracis* strain S51 | AB116124 | *Microsporidium* sp. STF | AY140647 |
| *Clostridium botulinum* strain AIP 355.02 | AY303799 | *Naegleria fowleri* | AF338423 |
| *Francisella tularensis* strain 3523 | AY243028 | OTU TL1A1, multi-copy, unidentified | |
| *Yersinia pestis* | AF366383 | OTU TL1A2, multi-copy, unidentified | |
| *Brucella melitensis* | AF220149 | OTU TL1A9, multi-copy, unidentified | |
| *Burkholderia mallei* strain 2000031063 | AY305760 | OTU TL1A12, multi-copy, unidentified | |
| *Chlamydophila psittaci* clone cvCps2 | AY334530 | OTU TL1A16, multi-copy, unidentified | |
| *Coxiella burnetii,* strain Nine Mile | Y11502 | OTU TL1A21, multi-copy, unidentified | |
| *Escherichia coli* O157:H7 | AB035920 | OTU CL1A3, single-copy, unidentified | |
| *Escherichia coli* O157:H7 EDL933 | NC 002655 | OTU CL1A4, single-copy, unidentified | |
| *Escherichia coli* O157:H7 EDL933 | NC 002655 | OTU CL1A5, single-copy, unidentified | |
| *Escherichia coli* O157:H7 EDL933 | NC 002655 | OTU CL1A6, single-copy, unidentified | |
| *Escherichia coli* O157:H7 EDL933 | NC 002655 | OTU CL1A8, multi-copy, unidentified | |
| *Escherichia coli* O157:H7 EDL933 | NC 002655 | OTU LT2A12, multi-copy, unidentified | |
| *Escherichia coli* O157:H7 EDL933 | NC 002655 | OTU LT2A20, single-copy, unidentified | |
| *Escherichia coli* O157:H7 EDL933 | NC 002655 | OTU LT1A3, single-copy, unidentified | |
| *Escherichia coli* O157:H7 EDL933 | NC 002655 | OTU LT1A42, multi-copy, identified as *Cryptomonas* sp., strain M420 | |
| *Escherichia coli* K12 | NC 000913 | OTU LT1A5, multi-copy, unidentified | |
| *Escherichia coli* K12 | NC 000913 | OTU LT1A4, multi-copy, identified as *Cryptomonas ovata,* strain CCAP 979/61 | |
| *Escherichia coli* K12 | NC 000913 | OTU LT1A8, multi-copy, unidentified | |
| *Escherichia coli* K12 | NC 000913 | OTU LT2A7, multi-copy, identified as *Dileptus* sp. | |
| *Rickettsia prowazekii* | M21789 | OTU LT1A9, single-copy, unidentified | |
| *Salmonella typhimurium* | Z49264 | OTU LT2A19, single-copy, identified as *Coleps* sp. | |
| *Vibrio cholerae* (CECT 514 T) | X76337 | OTU LT1A10, multi-copy, unidentified | |
| *Campylobacter jejuni* strain B99/206 | AF550630 | OTU LT1A11, single-copy, unidentified | |
| *Legionella pneumophila* serogroup 6 | AJ496383 | OTU LT1A13, single-copy, unidentified | |
| *Leptospira interrogans* | Z12817 | OTU LT3A2, single-copy, unidentified | |
| *Pseudomonas aeruginosa,* strain WatG | AB117953 | OTU LT3A5, multi-copy, unidentified | |
| OTU TL1A1, multi-copy, unidentified | | OTU LT3A6, multi-copy, unidentified | |
| OTU TL1A2, multi-copy, unidentified | | OTU LT3A11, single-copy, unidentified | |
| OTU TL1A6, single-copy, unidentified | | OTU LT3A13, single-copy, unidentified | |
| OTU TL1A7, multi-copy, identified as Uncultured beta proteobacterium clone OS1L-16 | | OTU LT1A1, multi-copy, unidentified | |
| OTU LT1A31, multi-copy, identified as Uncultured Crater Lake bacterium CL500-18 | | OTU LT1A38, multi-copy, unidentified | |
| OTU LT1A55, multi-copy, identified as Uncultured freshwater bacterium LCK-26 | | | |
| OTU CL1A2, multi-copy, unidentified | | | |
| OTU CL1A9, multi-copy, identified as *Zoogloea ramigera* | | | |
| OTU CL1A10, multi-copy, unidentified | | | |
| OTU CL1A15, single-copy, identified as Uncultured Crater Lake bacterium CL0-27 | | | |
| OTU LT1A54, multi-copy, identified as Uncultured Crater Lake bacterium CL0-64 | | | |
| OTU LT1A27, multi-copy, identified as Uncultured actinomycete clone SFD1-39 | | | |
| OTU LT2A3, multi-copy, unidentified | | | |
| OTU LT1A46, multi-copy, identified as Uncultured planctomycete clone CY0ARA031E04 | | | |

TABLE 13-continued

Primer/Probe combinations spotted on microarrays

| 16S rDNA sequence | GenBank accession no. | 18S rDNA sequence | GenBank accession no. |
|---|---|---|---|
| OTU LT2A12, multi-copy, unidentified | | | |
| OTU LT2A16, multi-copy, unidentified | | | |
| OTU LT1A53-3A9, multi-copy, identified as *Synechococcus* sp. | | | |
| OTU LT1A53, multi-copy, identified as *Synechococcus* sp. LBG2 | | | |
| OTU LT3A9, multi-copy, identified as *Synechococcus* sp. LBP1 | | | |
| OTU LT3A11, multi-copy, identified as Unidentified cyanobacterium clone LD27 | | | |
| Arsenite-oxidizing bacterium MLHE-1 | | | |
| *Thiomicrospira* sp. CVO | | | |
| *Desulfovibrio longreachii* | | | |
| *Bacillus arsenicoselenatis* | | | |
| OTU LT3A1, single-copy, unidentified | | | |
| OTU LT3A2, multi-copy, unidentified | | | |
| OTU LT3A7, multi-copy, unidentified | | | |
| OTU LT1A15, single-copy, unidentified | | | |
| OTU LT1A16, multi-copy, unidentified | | | |
| OTU LT1A18, multi-copy, unidentified | | | |
| OTU LT1A35, multi-copy, unidentified | | | |
| OTU LT1A55, multi-copy, unidentified | | | |

TABLE 14

Oligonucleotide probes on array of FIG. 14

| A | | | | | | B | | | | | |
|---|---|---|---|---|---|---|---|---|---|---|---|
| | | | | | | 19P | 20P | 21P | 22P | 18P | 23P |
| | | | | | | 24P | 25P | 26P | 27P | 28P | |
| | | | | | | 17P | 29P | | | | |
| | | | | | | | | | | | Cy3 9mer |

| C | | | | | | D | | | | | |
|---|---|---|---|---|---|---|---|---|---|---|---|
| 43P | 44P | 45P | 46P | 47P | 48P | 95P | 96P | 97P | 86P | 87P | 88P |
| 49P | 50P | 65P | 66P | 67P | 68P | 91P | 98P | 92P | 99P | 89P | 90P |
| 69P | 70P | 71P | 72P | | | 93P | 100P | 94P | 101P | 102P | |
| | | | | | | | | | | | Cy3 9mer |

| E | | | | | | F | | | | | |
|---|---|---|---|---|---|---|---|---|---|---|---|
| 15P | 30P | 31P | 32P | 16P | 33P | 10P | 11P | 12P | 13P | 1P | 2P |
| 34P | 14P | 35P | 36P | 38P | 39P | 3P | 4P | 5P | 6P | 7P | 8P |
| 40P | 41P | | | | | | | | | | |
| | | | | | | | | | | | Cy3 9mer |

| G | | | | | | H | | | | | |
|---|---|---|---|---|---|---|---|---|---|---|---|
| 51P | 52P | 53P | 54P | 55P | 56P | 83P | 81P | 73P | 74P | 75P | 76P |
| 57P | 58P | 60P | 61P | 62P | 63P | 84P | 85P | 82P | 80P | 77P | 78P |
| | | | | | | 79P | 106P | 107P | 108P | | |
| | | | | | | 103P | 104P | 105P | 109P | 110P | Cy3 9mer |

Such taxon-specific arrays may be developed for specific bodies of water. For example, arrays may be developed for lakes, marshes, tidal pools, or estuaries. Such arrays may include probes developed for freshwater systems, as these may be diagnostic for known pathogens (e.g., coliform bacteria) or environmental conditions (e.g., eutrophication). Also, sequences specific to microbes known to be common in the body of water of interest may be used. For example, for estuaries, phytoplankton populations have been described (Williams, R. B. and M. B. Murdoch 1966, *Limnology and Oceanography* 11:73–82., Thayer, G. W., 1971 *Estuaries* 12:240–253; Mallin 1994, Mallin, et al. 2000). A review of the literature indicates that many of the sequences that may be used are known (Table 15). Using this information, primers and probes to these common organisms, may be designed. Finally, probes for the array may be derived by sequencing clonal libraries derived from field samples as described herein for the lake samples to develop additional OTUs. For example, to develop an estuary array, water samples may be collected every few months in estuarine tidal creeks at various sites representing a range of estuarine conditions. Specific sampling locations may be water quality monitoring stations, and samples may be taken late on the flooding tide and six hours later on the ebbing tide, to provide a representative sample of both the community that enters the estuarine site as well as the community that leaves the estuarine site with the falling tide.

It should be understood that various changes and modifications to the embodiments described herein will be apparent to those skilled in the art. Such changes and modifications can be made without departing from the spirit and scope of the present invention and without diminishing its attendant scope and/or advantages.

TABLE 15

Examples of organisms of interest for North Carolina estuarine microarray targets based on literature reports[4]

Phytoplankton

| | |
|---|---|
| Cyclotella spp. | Melosira spp. |
| Nitzschia spp. | Navicula spp. |
| Psuedo-nitzschia australis[3] | Skeletonema costatum[1] |
| Thalassiosira spp. | |
| Amphidinium spp. | Ceratium spp. |
| Chattonella spp.[3] (C. antiqua, C. verruculosa) | Gymnodinium sanguineum |
| Heterocapsa triquetra[1] | Heterosgima akashiwo[3] |
| Hematodinium perezi[3] | Karenia brevis[3] |
| Karlodinium micrum[1] | Katodinium rotundatum[1] |
| Pfiesteria piscicida[3], P. shumwayae[3] | Prorocentrum minimum[1] |
| Calicomonas ovalis | Chlamydomonas spp. |
| Chroomonas spp. (C. minuta, C. amphioxiae) | Cyrptomonas testaceae |
| Hemiselmis virescens | Phaeocystis globosa |
| Pyramimonas | Eutreptia[1] |

Bacteria

| | |
|---|---|
| Acinetobcter spp. | Alcaligenes spp. |
| Bacteroides spp.[2] | Enterococcus spp.[2] (E. faecalis, E. faecium) |
| Escherichia spp.[2,3] (E. coli, E. coli O157H7) | Flavobacterium spp. |
| Oceanospirillum spp. | Salmonella spp.[2,3] (S. typhi, S. non-typhi) |
| Psuedomonas aeruginosa | Shigella sp.[2,3] |
| Clostridium sp.[2,3] (C. perfringens, C. botulinum Type E) | |
| Vibrio sp.[3] (V. anguillarum, | |

TABLE 15-continued

Examples of organisms of interest for North Carolina estuarine microarray targets based on literature reports[4]

V. cholerae 01, V. cholerae non 01,
V. parahaemolyticus V. vulnificus

Virus

| | |
|---|---|
| Hepatitis A[3] | Norwalk virus[3] |
| Adenovirus[3] | rotavirus[3] |
| Protozoa | |
| Kudoa spp.[3] (K. clupeidae, K. fundulae) | Cryptosporidium spp.[2,3] |
| Giardia[2,3] | Perkinsus marinus[3] |
| Haplosporidium[3] | |
| Fungi | |

Aphanomyces invadens[3]

[1]Genera or species referenced in the literature as commonly found in southeastern estuarine systems, and likely to be indicators of good ecosystem health (e.g. Campbell, 1973, Univ. of N.C. Sea Grant Publication, UNC-SG-73-07; Mallin, et al. 2000, American Scientist, 88:26–37; Shubert, 1984, In Algae as Ecological Markers, Academic Press, NY, p. 434; Stoermer and Smol, 1999, In The Diatoms: Applications For the Environmental and Earth Sciences, Cambridge Univ. Press, Cambridge, UK, page 469; Thayer, 1971, Estuaries, 12:240–253, Williams and Murdoch, 1966, Limnology and Oceanography, 11:73–82;).
[2]Microbes linked to specific contamination sources (e.g. human sewage) which indicate point or non-point source pollution (e.g. Bernhard and Field, 2000, Applied and Environmental Microbiology, 66:4641–4648; Lipp, et al. 2001, Marine Pollution Bull., 42:286–293; Mallin, et al., 2000b, Ecological Applications, 10:1047–1056' USEPA, 1985, Test methods for Escherichia coli and Enterococci in water by the membrane filter procedure, EPA600/4-85/076)
[3]Known human, fish, or shellfish pathogens or parasites (e.g. DeLeon, et al. 1990, In Proceeding of the Water Quality Conference, San Diego, CA, American Water Works Association, 18:833–853; Grimes 1991, Estuaries, 14:345–360; Kane, et al., 1998, Maryland Medical Journal, 37:106–112; Lipp, 1999, , Reed and Francis-Floyd, 1996, Vibrio Infections of Fish, Florida Cooperative Extension Service, Institute of Food and Agricultural Sciences, University of Florida web-site; Shields, 1997, An investigation into the epidemiology of Hematodinium perezi, a parasitic dinoflagellate in the blue crab, Callinectes sapidus, available on-line)
[4]Many of the taxa listed have GenBank sequence entries for one or more species.

What is claimed is:

1. A method for monitoring an ecosystem of interest comprising:
    (a) generating an array comprising a plurality of oligonucleotides immobilized at known locations on a substrate, wherein each location on the substrate comprises an oligonucleotide having a sequence derived from a single, predetermined microbial operational taxonomic unit (OTU), and wherein the array comprises at least one oligonucleotide having the sequence as set forth in SEQ ID NO: 25, SEQ ID NO: 26, SEQ ID NO: 32, SEQ ID NO: 40, SEQ ID NO: 98, or SEQ ID NO: 100, or SEQ ID NO: 106, the complement of the sequence as set forth in SEQ ID NO: 25, SEQ ID NO: 26, SEQ ID NO: 32, SEQ ID NO: 40, SEQ ID NO: 98, SEQ ID NO: 100 or SEQ ID NO: 106;
    (b) preparing a nucleic acid sample from the ecosystem of interest;
    (c) hybridizing the nucleic acid sample to the array;
    (d) measuring hybridization of the nucleic acid sample to the array; and
    (e) correlating hybridization of the nucleic acid sample to the array with at least one parameter that comprises at least part of the ecosystem of interest.

2. The method of claim 1, wherein the ecosystem of interest comprises water.

3. The method of claim 2, wherein the at least one parameter comprises water quality.

4. The method of claim 1, wherein at least one of the immobilized oligonucleotides comprises a eukaryotic ribosomal DNA sequence and at least one of the immobilized oligonucleotides comprises a prokaryotic ribosomal DNA sequence.

5. The method of claim 1, wherein at least one immobilized oligonucleotide comprises the sequence as set forth in any one of SEQ ID NO: 5–SEQ ID NO: 113, or the complement of any one of SEQ ID NO: 5–SEQ ID NO: 113.

6. The method of claim 1, wherein there are at least 10 different immobilized oligonucleotides and each of the at least 10 immobilized oligonucleotides individually comprises the sequence as set forth in any one of SEQ ID NO: 5–SEQ ID NO: 113, or the complement of any one of SEQ ID NO: 5–SEQ ID NO: 113.

7. The method of claim 1, wherein there are at least 50 different immobilized oligonucleotides and each of the at least 50 immobilized oligonucleotides individually comprises the sequence as set forth in any one of SEQ ID NO: 5–SEQ ID NO: 113, or the complement of any one of SEQ ID NO: 5–SEQ ID NO: 113.

8. The method of claim 1, wherein the nucleic acid sample hybridized to the array comprises a plurality of rDNA sequences.

9. The method of claim 1, wherein the nucleic acid sample hybridized to the array is generated using polymerase chain reaction (PCR) primers derived at least in part from a small subunit (SSU) ribosomal DNA variable region.

10. The method of claim 9, wherein at least one of the PCR primers comprises the sequence identical to any one of SEQ ID NO: 114–SEQ ID NO: 316.

11. The method of claim 1, wherein a single change in a pattern of hybridization to the array for a second DNA sample isolated from the ecosystem of interest as compared to a first DNA sample isolated from the ecosystem of interest is associated with a change in one or more parameters specific to at least part of the ecosystem of interest.

12. The method of claim 1, wherein a plurality of changes in a pattern of hybridization to the array for a second DNA sample isolated from the ecosystem of interest as compared to a first DNA sample isolated from the ecosystem of interest is associated with a change in one or more parameters specific to at least part of the ecosystem of interest.

13. A method for analyzing a pattern to evaluate the status of an ecosystem of interest comprising:
    measuring hybridization of a nucleic acid sample isolated from the ecosystem of interest to an array of oligonucleotides immobilized at known locations on a substrate, wherein each location on the array comprises an oligonucleotide having a sequence that is derived from a single, predetermined microbial operational taxonomic unit (OTU), and wherein the array comprises at least one oligonucleotide having the sequence as set forth in SEQ ID NO: 25, SEQ ID NO: 26, SEQ ID NO: 32, SEQ ID NO: 40, SEQ ID NO: 98, SEQ ID NO: 100, or SEQ ID NO: 106, or the complement of the sequence as set forth in SEQ ID NO: 25, SEQ ID NO: 26, SEQ ID NO: 32, SEQ ID NO: 40, SEQ ID NO: 98, SEQ ID NO: 100, or SEQ ID NO: 106; and
    correlating a pattern of hybridization of the nucleic acid sample to the array with at least one parameter that comprises at least part of the ecosystem of interest.

14. The method of claim 13, wherein a single change in the pattern of hybridization to the array for a second DNA sample isolated from the ecosystem of interest as compared to a first DNA sample isolated from the ecosystem of interest is associated with a change in one parameter that comprises at least part of the ecosystem of interest.

15. The method of claim 13, wherein a single change in the pattern of hybridization to the array for a second DNA sample isolated from the ecosystem of interest as compared to a first DNA sample isolated from the ecosystem of interest is associated with a change in a plurality of parameters that comprise at least part of the ecosystem of interest.

16. The method of claim 13, wherein a plurality of changes in the pattern of hybridization to the array for a second DNA sample isolated from the ecosystem of interest as compared to a first DNA sample isolated from the ecosystem of interest is associated with a change in one parameter that comprises at least part of the ecosystem of interest.

17. The method of claim 13, wherein a plurality of changes in the pattern of hybridization to the array for a second DNA sample isolated from the ecosystem of interest as compared to a first DNA sample isolated from the ecosystem of interest is associated with a change in a plurality of parameters that comprise at least part of the ecosystem of interest.

18. The method of claim 1, wherein the plurality of immobilized oligonucleotides further comprises at least one oligonucleotide having the sequence as set forth in SEQ ID NO: 20, SEQ ID NO: 107, or SEQ ID NO: 109, or the complement of the sequence as set forth in SEQ ID NO: 20, SEQ ID NO: 107, or SEQ ID NO: 109.

19. The method of claim 1, wherein the plurality of immobilized oligonucleotides further comprises at least one oligonucleotide having the sequence as set forth in SEQ ID NO: 13, SEQ ID NO: 18, SEQ ID NO: 19, SEQ ID NO: 21, SEQ ID NO: 22, SEQ ID NO: 23, SEQ ID NO: 24, SEQ ID NO: 27, SEQ ID NO: 28, SEQ ID NO: 29, SEQ ID NO: 30, SEQ ID NO: 31, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 41, SEQ ID NO: 42, SEQ ID NO: 43, SEQ ID NO: 44, SEQ ID NO: 45, SEQ ID NO: 84, SEQ ID NO: 88, SEQ ID NO: 89, SEQ ID NO: 91, SEQ ID NO: 94, SEQ ID NO: 97, SEQ ID NO: 99, SEQ ID NO: 101, SEQ ID NO: 102, SEQ ID NO: 103, SEQ ID NO: 104, SEQ ID NO: 105, SEQ ID NO: 108, SEQ ID NO: 110, SEQ ID NO: 111, or SEQ ID NO: 112, or the complement of the sequence as set forth in SEQ ID NO: 13, SEQ ID NO: 18, SEQ ID NO: 19, SEQ ID NO: 21, SEQ ID NO: 22, SEQ ID NO: 23, SEQ ID NO: 24, SEQ ID NO: 27, SEQ ID NO: 28, SEQ ID NO: 29, SEQ ID NO: 30, SEQ ID NO: 31, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 41, SEQ ID NO: 42, SEQ ID NO: 43, SEQ ID NO: 44, SEQ ID NO: 45, SEQ ID NO: 84, SEQ ID NO: 88, SEQ ID NO: 89, SEQ ID NO: 91, SEQ ID NO: 94, SEQ ID NO: 97, SEQ ID NO: 99, SEQ ID NO: 101, SEQ ID NO: 102, SEQ ID NO: 103, SEQ ID NO: 104, SEQ ID NO: 105, SEQ ID NO: 108, SEQ ID NO: 110, SEQ ID NO: 111, or SEQ ID NO: 112.

20. The method of claim 13, wherein at least one immobilized oligonucleotide comprises the sequence identical to any one of SEQ ID NO: 5–SEQ ID NO: 113, or the complement of SEQ ID NO: 5- SEQ ID NO: 113.

21. The method of claim 13, wherein are at least 10 different immobilized oligonucleotides and each of the at least 10 immobilized oligonucleotides individually comprises the sequence as set forth in any one of SEQ ID NO: 5–SEQ. ID NO: 113, or the complement of SEQ ID NO: 5–SEQ ID NO: 113.

22. The method of claim 13, wherein there are at least 50 different immobilized oligonucleotides and each of the at least 50 immobilized oligonucleotides individually comprises the sequence as set forth in any one of SEQ ID NO: 5–SEQ ID NO: 113, or the complement of SEQ ID NO: 5-SEQ ID NO: 113.

23. The method of claim 13, wherein the plurality of immobilized oligonucleotides further comprise at least one oligonucleotide having the sequence as set forth in SEQ ID NO: 20, SEQ ID NO: 107, SEQ ID NO: 109, or the complement of the sequence as set forth in SEQ ID NO: 20, SEQ ID NO: 107, or SEQ ID NO: 109.

24. The method of claim 13, wherein the plurality of immobilized oligonucleotides further comprise at least one oligonucleotide having the sequence as set forth in SEQ ID NO: 13, SEQ ID NO: 18, SEQ ID NO: 19, SEQ ID NO: 21, SEQ ID NO: 22, SEQ ID NO: 23, SEQ ID NO: 24, SEQ ID NO: 27, SEQ ID NO: 28, SEQ ID NO: 29, SEQ ID NO: 30, SEQ ID NO: 31, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 41, SEQ ID NO: 42, SEQ ID NO: 43, SEQ ID NO: 44, SEQ ID NO: 45, SEQ ID NO: 84, SEQ ID NO: 88, SEQ ID NO: 89, SEQ ID NO: 91, SEQ ID NO: 94, SEQ ID NO: 97, SEQ ID NO: 99, SEQ ID NO: 101, SEQ ID NO: 102, SEQ ID NO: 103, SEQ ID NO: 104, SEQ ID NO: 105, SEQ ID NO: 108, SEQ ID NO: 110, SEQ ID NO: 111, or SEQ ID NO: 112, or the complement of the sequence as set forth in SEQ ID NO: 13, SEQ ID NO: 18, SEQ ID NO: 19, SEQ ID NO: 21, SEQ ID NO: 22, SEQ ID NO: 23, SEQ ID NO: 24, SEQ ID NO: 27, SEQ ID NO: 28, SEQ ID NO: 29, SEQ ID NO: 30, SEQ ID NO: 31, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 41, SEQ ID NO: 42, SEQ ID NO: 43, SEQ ID NO: 44, SEQ ID NO: 45, SEQ ID NO: 84, SEQ ID NO: 88, SEQ ID NO: 89, SEQ ID NO: 91, SEQ ID NO: 94, SEQ ID NO: 97, SEQ ID NO: 99, SEQ ID NO: 101, SEQ ID NO: 102, SEQ ID NO: 103, SEQ ID NO: 104, SEQ ID NO: 105, SEQ ID NO: 108, SEQ ID NO: 110, SEQ ID NO: 11, or SEQ ID NO: 112.

\* \* \* \* \*

UNITED STATES PATENT AND TRADEMARK OFFICE
CERTIFICATE OF CORRECTION

PATENT NO.         : 7,214,492 B1
APPLICATION NO. : 11/071849
DATED              : May 8, 2007
INVENTOR(S)        : Parke A. Rublee and Vincent C. Henrich, III It is certified that error appears in the above-identified patent and that said Letters Patent is hereby corrected as shown below:

Column 22, line 65, that portion reading "Venn diagrams may be used depict" should read --Venn diagrams may be used to depict--

Column 26, line 66, that portion reading "specific a particular" should read --specific to a particular--

Column 43, line 61, that portion reading "and products each reaction." should read --and products of each reaction--

Column 169, claim 21, that portion reading "The method of claim 13, wherein are at least 10," should read --The method of claim 13, wherein there are at least 10--

Signed and Sealed this

Second Day of September, 2008

JON W. DUDAS
*Director of the United States Patent and Trademark Office*